(12) United States Patent
Chang

(10) Patent No.: US 8,802,695 B2
(45) Date of Patent: Aug. 12, 2014

(54) APOPTOSIS SIGNAL-REGULATING KINASE 1 INHIBITORS

(75) Inventor: Edcon Chang, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/577,182

(22) PCT Filed: Jan. 21, 2011

(86) PCT No.: PCT/US2011/022137
§ 371 (c)(1),
(2), (4) Date: Aug. 3, 2012

(87) PCT Pub. No.: WO2011/097079
PCT Pub. Date: Aug. 11, 2011

(65) Prior Publication Data
US 2012/0316194 A1  Dec. 13, 2012

Related U.S. Application Data

(60) Provisional application No. 61/300,869, filed on Feb. 3, 2010.

(51) Int. Cl.
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl.
USPC .......................................... 514/300; 546/113

(58) Field of Classification Search
None
See application file for complete search history.

(56) References Cited

FOREIGN PATENT DOCUMENTS

| EP | 2058309 | | 5/2009 |
|---|---|---|---|
| EP | 2058309 A1 | * | 5/2009 |
| WO | 2009027283 | | 3/2009 |

OTHER PUBLICATIONS

Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Yanker, BA. Apoptosis in the nervous system. Nature. 2000, vol. 407, p. 802.*
Thompson, CB. Apoptosis in the Pathogenesis and Treatment of Disease. Science. 1995, vol. 267, p. 1456.*
Jove, R. Constitutive Activation of Stat3 Signaling Confers Resistance to Apoptosis in Human U266 Myeloma Cells. Immunity. vol. 10, p. 105.*
Database Registry [online] Chemical Abstract Service, Columbus Ohio, US; Aug. 1, 2000 XP002628377 Database accession No. 282108-86-5.
PCT/US2011/022137 International Search Report, Mar. 31, 2011.

* cited by examiner

*Primary Examiner* — Rita Desai
*Assistant Examiner* — Ben S Michelson
(74) *Attorney, Agent, or Firm* — Matthew J. Russo; C. Amy Smith

(57) ABSTRACT

The present invention relates to apoptosis signal-regulating kinase 1 ("ASK1") inhibiting compounds of the formula

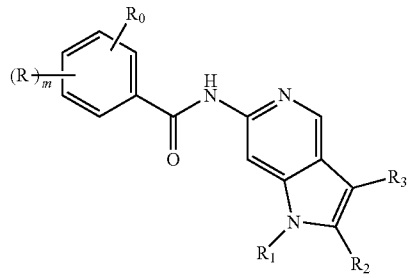

wherein the variables are as defined herein. The invention also relates to pharmaceutical compositions, kits and articles of manufacture comprising such compounds; methods and intermediates useful for making the compounds; and methods of using said compounds.

26 Claims, 1 Drawing Sheet

DNA Sequence Encoding First PCR Primer [SEQ ID NO: 1]

```
aaaagtcgac atggactaca aggacgacga tgacaaggtg aacaccatta ccgaagagaa    60
gggga                                                                65
```

DNA Sequence Encoding Second PCR Primer [SEQ ID NO: 2]

```
aaagcggccg ctcaagtctg tttgtttcga aagtcaatg                           39
```

APOPTOSIS SIGNAL-REGULATING KINASE 1 INHIBITORS

CROSS-REFERENCE TO RELATED APPLICATION

This application is the U.S. National Stage entry under 35 U.S.C. 371(c) of International Application PCT/US11/022137, filed Jan. 21, 2011, which claims the benefit of U.S. Provisional Application No. 61/300,869, filed Feb. 3, 2010, which is herein incorporated by reference.

FIELD OF THE INVENTION

The present invention relates to compounds that may be used to inhibit apoptosis signal-regulating kinase 1 (ASK1) as well as compositions of matter, kits and articles of manufacture comprising these compounds. The invention also relates to methods for inhibiting ASK1 and treatment methods using compounds according to the present invention. In addition, the invention relates to methods of making the compounds of the present invention, as well as intermediates useful in such methods. In particular, the present invention relates to ASK1 inhibitors, compositions of matter, kits and articles of manufacture comprising these compounds, methods for inhibiting ASK1, and methods and intermediates useful for making the inhibitors.

BACKGROUND OF THE INVENTION

Apoptosis signal-regulating kinase 1 (ASK1), is a member of the mitogen-activated protein kinases (MAPKs) family, which are members of the serine/threonine kinase family. Wang et al. *J. Biol. Chem.* 1996, 271, 31607-31611, Ichijo et al. *Science* 1997, 275, 90-94. ASK1 is also known as mitogen-activated protein kinase kinase kinase 5 (MAPKKK5, MAP3K5), MAP/ERK kinase kinase 5 (MEKK5), MEK kinase 5, MEKK5, MAP/ERK kinase kinase 5. The protein kinase composes of 1375 amino acids encompassing 11 kinase subdomains; particularly a serine/threonine kinase domain in the middle part of the molecule with long NH- and COOH-terminal flanking regions. Wang et al. *J. Biol. Chem.* 1996, 271, 31607-31611, Ichijo et al. *Science* 1997, 275, 90-94; Tobiume et al. *Biochem. Biophys. Res. Commun.* 1997, 239, 905-910; U.S. Pat. Nos. 6,080,546 and 6,194,187. The nucleotide sequence of ASK1 is accessible in the protein databases by the accession number NM_005923. ASK1 is ubiquitously expressed with the highest expression in the heart, pancreas, testis, and ovaries.

The MAP kinases mediate signal transduction from the cell surface to the nucleus via phosphorylation cascades. Egan and Weinbery *Nature* 1993, 365, 781-783.

The MAPK cascades are multifunctional intracellular signaling pathways that are evolutionarily conserved in all eukaryotic cells. Widmann et al. *Physiol Rev* 1999, 79, 143-180; Kyriakis and Avruch, J. *Physiol Rev* 2001, 81, 807-869; Ichijo *Oncogene* 1999, 18:6087-6093. All eukaryotic cells possess multiple MAPK pathways. In mammalian cells, three MAPK cascades that converge on ERKs, c-Jun N-terminal kinases (JNKs), and p38 MAP kinases have been extensively characterized. Egan and Weinbery *Nature* 1993, 365, 781-783; Boulton et al. *Cell* 1994, 65, 663-675; and Zhou et al. *J. Biol. Chem.* 1995, 270, 12665-12669 (the MAPK/ERK pathway); Derujard et al. *Cell* 1994, 76, 1025-1037; Galcheva-Gargova et al. *Science* 1994, 265, 806-808; Minden et al. *Mol. Cell. Biol.* 1994, 14, 6683-6688 (the c-Jun N-terminal kinase (JNK) pathway; and Lee et al. *Science* 1994, 265, 808-811, (the p38 MAPK pathways). ERK pathway is activated by various growth factors and closely linked to the regulation of cell cycle. The JNK and p38 pathways are preferentially activated by various cytotoxic stress such as UV radiation, X-ray, heat shock, osmotic shock, oxidative stress and pro-inflammatory cytokines such as tumor necrosis factor (TNF) and interleukin-1 Tibbles and Woodgett, *Cell Mol, Life Sci.* 1999, 55:1230-1254. JNK and p38 are thus also called stress-activated protein kinases (SAPKs).

Each MAPK cascade involves three classes of serine/threonine kinases, MAPK, MAPK kinanse (MAP2K) and MAP2K kinase (MAP3K). In the MAPK signaling cascades, MAP3K phosphorylates and thereby activates MAP2K in turn phosphorylates and activates MAPK. Activated MAPK may translocate to the cell nucleus and regulate the activities of transcription factors and thereby control gene expression. Sturgill and Wu, *Biochim. Biophys. Acta* 1993, 1092, 350; Nishida and Gotoh, *Trends Biochem. Sci.* 1993, 18, 128; Errede and Levin *Curr. Opin. Cell Biol.* 1993, 5, 254; Marshall *Curr. Opin. Genet. Dev.* 1994, 82.

MAP3Ks play pivotal roles in sensing and signaling of cellular and environmental stress. The MAP3Ks in the JNK and p38 pathways are highly divergent in number and structure. At least eleven MAP3Ks have been identified upstream of JNK, each of which activates single or multiple downstream MAPK cascades. This diversity and complexity are consistent with the variety of stimuli that activate MAPK pathways. Kyriakis and Avruch *Physiol. Rev.* 2001, 81, 807-869.

One of the important biological responses mediated through these stress-activated MAP kinase pathways appears to be the decision of cell fate by regulating apoptosis. The possible roles of the JNK pathway in pro-apoptosis signaling have been demonstrated by knockout mouse studies. Yang et al. *Nature* 1997, 389:865-870; Sabapathy et al. *Curr. Biol.* 1999, 9:116-125; Kuan et al. *Neuron* 1999, 22:667-676. Several lines of evidence have also suggested the pro-apoptotic roles of the p38 pathway. Xia et al. *Science* 1995, 270:1326-1331; Kawaski et al. *J. Biol. Chem.* 1997, 272:18518-18521; Harper and LoGrasso et al. *Cell Signal.* 2001, 13:299-310.

ASK1 was originally identified as an apoptosis-inducing MAP3K. ASK1 regulates the p38 and JNK pathways by directly phosphorylating and thereby activating their respective MAPKKs, MKK4(SEK1)/MKK7 and MKK3/MKK6. Wang et al. *J. Biol. Chem.* 1996, 271, 31607-31611; Ichijo et al. *Science* 1997, 275, 90-94. The activity of ASK1 is tightly regulated; a ubiquitously expressed reduction/oxidation protein thioredoxin (Trx) binds to the N-terminal and inhibits its activity. ASK1 is activated by various cytotoxic stresses including oxidative stress, endoplasmic reticulum (ER) stress, and calcium overload, and by receptor-mediated inflammatory signals such as tumor necrosis factor (TNF) and endotoxic lipopolysaccharide (LPS). Hayakaw et al. *Microbes and Infection* 2006, 8, 1098-1107; Saitoh et al *EMBO J.* 1998, 17:2596-2606; Nishitoh et al. *Genes Dev.* 2002, 16:1345-1355; Takeda et al. *EMBO Rep.* 2004, 5, 161-166; Nishitoh et al. *Mol Cell* 1998, 2,389-395; Matsukawa et al. *Nat Immunol* 2005, 6, 587-592. It has been shown that ASK1 is required for apoptosis induced by oxidative stress, TNF and ER stresses. Nishitoh et al. *Genes Dev.* 2002, 16:1345-1355; Matsukawa et al. *Nat Immunol* 2005, 6, 587-592; Tobiume et al. *EMBO Rep.* 2001, 2:222-228. Overexpression of wild-type or constitutively active ASK1 induces apoptosis in various cells through mitochondria-dependent caspase activation. Saitoh et al *EMBO J.* 1998, 17:2596-2606; Kanamoto et al. *Mol. Cell. Biol.* 2000, 20, 196-204; Hatai et al. *J. Biol. Chem.* 2000, 275, 26576-26588.

Recent studies revealed that ASK1 contributes not only to regulation of cell death but also has diverse functions in the decision of cell fate such as cytokine responses, cell differentiation, and innate immune responses. Matsukawa et al. *J Biochem.* (*Toyko*) 2004, 136, 261-265. Sayama et al. *J. Biol. Chem.* 2000, 276:999-1004; Takeda et al. *J. Biol. Chem.* 2000, 275:9805-9813; Sagasti et al. *Cell* 2001, 105:221-232; Kim et al. *Science* 2002, 297:623-626; Nishitoh et al. *Genes Dev.* 2002, 16:1345-1355; Matsukawa et al. *Nat Immunol* 2005, 6, 587-592; Tobiume et al. *EMBO Rep.* 2001, 2:222-228; Imoto, et al. *Diabetes* 2006, 55:1197-1204. Constitutively active ASK1 induces neurite outgrowth in PC12 cells. ASK1 is activated by CaMKII, which activates ASK1-p38 pathway in neurons, suggesting that ASK1 might play critical roles in synaptic plasticity. Moreover, TRAF6-ASK1-p38 pathway plays an essential role in inflammatory and innate immune responses. Hayakawa et al. *Microbes and Infection* 2006, 8, 1098-1107. It has also been demonstrated that ASK1 has a role in the pathogenesis of TNF-α-induced insulin resistance. Overexpression of wild-type ASK1 increases serine phosphorylation of insulin receptor substrate (IRS)-1, and decreases insulin-stimulated tyrosine phosphorylation of IIRS-1, leading to impair insulin signaling. Imoto, et al. *Diabetes* 2006, 55:1197-1204.

ASK1 is thus a pivotal component not only in stress-induced cell death but also in a broad range of biological activities in order for cells to adapt to or oppose various stresses. Modulating the activity of ASK1 potentially have beneficial effect in treating or preventing a wide range of diseases and conditions including, but not limited to, cardiovascular diseases, inflammatory diseases, autoimmune diseases, destructive bone disorders, neurodegenerative disorders, and metabolic diseases such as diabetes. Thompson, *Science* 1995, 267, 1456-1462; Yuan and Yanker *Nature* 2000, 407, 802-809; Los et al. *Immunity* 1999, 10, 629-639.

Currently, there are no known therapeutical agents that effectively inhibit the expression and/or activation of ASK1, and to date, strategies aimed at modulating ASK1 function have involved the use of antibodies, dominant negative and dominant active mutants of the protein.

U.S. Pat. No. 5,981,265 and No. 6,074,861 claim methods for regulating MAP3K protein activity in a cell by transforming or transfecting the cell with a nucleic acid that is capable of hybridizing under stringent conditions to a nucleic acid molecule encoding MAP3K1, MAP3K2, MAP3K3, MAP3K4, MAP3K5, and MAP3K6. Oligonucleotides for use in antisense, and triplex formation, as ribozymes, probes or primers and in other applications are generally disclosed. WO 01/07461 discloses antisense compositions and methods for using the antisense compositions to modulate the expression of MAP3K5 and treat diseases associated with expression of MAP3K5.

Consequently, there remains a long felt need for agents capable of effectively modulating the activity of ASK1. A small molecule inhibitor may be proof to be an effective means for regulating ASK1 activities.

SUMMARY OF THE INVENTION

The present invention relates to compounds that have activity for inhibiting ASK1. The present invention also provides compositions, articles of manufacture and kits comprising these compounds. In addition, the invention relates to methods of making the compounds of the present invention, as well as intermediates useful in such methods.

In one aspect, the invention is directed to compounds having the formula:

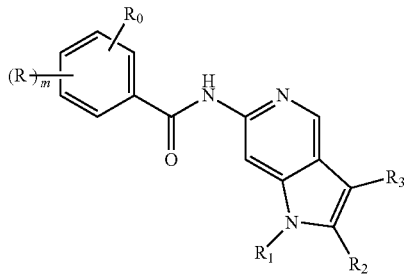

or stereoisomers, or pharmaceutically acceptable salts, thereof, wherein m is 0, 1, or 2;

$R_0$ is a substituted or unsubstituted hydroxy($C_{1-6}$)alkyl or a substituted or unsubstituted $R_4$-carbonyl($C_{1-6}$)alkyl;

each R is independently selected from the group consisting of hydroxy, nitro, halo, cyano, ($C_{1-6}$)alkoxy, ($C_{4-6}$)aryloxy, hetero($C_{1-5}$)aryloxy, ($C_{1-6}$)alkyl, amino($C_{1-6}$)alkyl, halo($C_{1-6}$)alkyl, ($C_{4-6}$)aryl($C_{1-3}$)alkyl, hetero($C_{1-5}$)aryl($C_{1-3}$) alkyl, ($C_{3-6}$)cycloalkyl, hetero($C_{1-5}$)cycloalkyl, ($C_{4-6}$)aryl, and hetero($C_{1-5}$)aryl, each unsubstituted or substituted with 1-3 substituents each of which is independently selected from the group consisting of hydroxy, halo, ($C_{1-6}$)alkoxy, halo($C_{1-6}$)alkoxy, amino, ($C_{1-6}$)alkyl, hydroxy($C_{1-6}$)alkyl, halo($C_{1-6}$)alkyl, perhalo($C_{1-6}$)alkyl, amino($C_{1-6}$)alkyl, hydroxy($C_{1-6}$)alkoxy, halo($C_{1-6}$)alkoxy, perhalo($C_{1-6}$) alkoxy, ($C_{3-6}$)cycloalkyl, $R_9$-carbonyl($C_{1-6}$)alkyl, $R_9$-sulfonyl($C_{1-6}$)alkyl, $R_9$-carbonyl, and $R_9$-sulfonyl;

$R_1$ is selected from the group consisting of cyano, ($C_{1-6}$) alkyl, ($C_{2-6}$)alkenyl, ($C_{3-6}$)cycloalkyl, hetero($C_{1-5}$)cycloalkyl, ($C_{4-6}$)cycloalkenyl, ($C_{4-6}$)cycloalkenyl, sulfonyl, hetero($C_{3-5}$)cycloalkenyl, ($C_{4-6}$)aryl, and hetero($C_{1-5}$)aryl, each unsubstituted or substituted with 1-3 substituents each of which is independently selected from the group consisting of hydroxy, halo, cyano, amino, carbonylamino, sulfonylamino, ($C_{3-6}$)cycloalkyl, ($C_{4-6}$)aryl, oxycarbonyl, hydroxycarbonyl, aminocarbonyl, sulfonyl, aminosulfonyl, wherein the amino, carbonylamino, sulfonylamino, oxycarbonyl, aminocarbonyl, sulfonyl, and aminosulfonyl are each unsubstituted or further substituted with 1-2 substituents independently selected from the group consisting of ($C_{1-6}$)alkyl, halo ($C_{1-6}$)alkyl, perhalo($C_{1-6}$)alkyl, and ($C_{3-6}$)cycloalkyl;

$R_2$ is selected from the group consisting of hydrogen, halo, nitro, cyano, thio, oxy, hydroxy, carbonyloxy, ($C_{1-6}$)alkoxy, ($C_{4-6}$)aryloxy, hetero($C_{1-5}$)aryloxy, carbonyl, oxycarbonyl, aminocarbonyl, sulfonyl, sulfinyl, ($C_{1-6}$)alkyl, halo($C_{1-6}$) alkyl, hydroxy($C_{1-6}$)alkyl, carbonyl($C_{1-6}$)alkyl, thiocarbonyl ($C_{1-6}$)alkyl, sulfonyl($C_{1-6}$)alkyl, sulfinyl($C_{1-6}$)alkyl, ($C_{3-6}$) cycloalkyl($C_{1-3}$)alkyl, hetero($C_{1-5}$)cycloalkyl($C_{1-3}$)alkyl, ($C_{4-6}$)aryl($C_{1-3}$)alkyl, hetero($C_{1-5}$)aryl($C_{1-3}$)alkyl, hetero($C_{1-5}$)alkyl, ($C_{3-6}$)cycloalkyl, hetero($C_{1-5}$)cycloalkyl, ($C_{4-6}$)aryl, and hetero($C_{1-5}$)aryl, each unsubstituted or substituted with 1-3 substituents each of which is independently selected from the group consisting of hydroxy, unsubstituted amino, mono-substituted amino, di-substituted amino, ($C_{1-6}$) alkyl, halo($C_{1-6}$)alkyl, ($C_{3-6}$)cycloalkyl and ($C_{4-6}$)aryl, provided when $R_3$ is hydrogen and $R_1$ is alkyl, $R_2$ is not aryl, heteroaryl, or heterocyclic;

$R_3$ is selected from the group consisting of hydrogen, halo, nitro, cyano, thio, oxy, hydroxy, carbonyloxy, ($C_{1-6}$)alkoxy, ($C_{4-6}$)aryloxy, hetero($C_{1-5}$)aryloxy, carbonyl, oxycarbonyl, aminocarbonyl, sulfonyl, sulfinyl, $(C_{1-6})$alkyl, halo$(C_{1-6})$alkyl, hydroxy$(C_{1-6})$alkyl, carbonyl$(C_{1-6})$alkyl, thiocarbonyl$(C_{1-6})$alkyl, sulfonyl$(C_{1-6})$alkyl, sulfinyl$(C_{1-6})$alkyl, $(C_{3-6})$cycloalkyl$(C_{1-3})$alkyl, hetero$(C_{1-5})$cycloalkyl$(C_{1-3})$alkyl, $(C_{4-6})$aryl$(C_{1-3})$alkyl, hetero$(C_{1-5})$aryl$(C_{1-3})$alkyl, hetero$(C_{1-5})$alkyl, $(C_{3-6})$cycloalkyl, hetero$(C_{1-5})$cycloalkyl, $(C_{4-6})$aryl, and hetero$(C_{1-5})$aryl, each unsubstituted or substituted with 1-3 substituents each of which is independently selected from the group consisting of hydroxy, halo, $(C_{1-6})$alkyl, halo$(C_{1-6})$alkyl, perhalo$(C_{1-6})$alkyl, $(C_{3-6})$cycloalkyl, hetero$(C_{1-5})$cycloalkyl, $(C_{4-6})$aryl, and hetero$(C_{1-5})$aryl;

$R_4$ is selected from the group consisting of hydroxy, unsubstituted amino, $(C_{1-6})$alkylamino, (di-$(C_{1-6})$alkyl)amino, $(C_{1-6})$alkoxy, and $(C_{1-6})$alkyl; and $R_9$ is selected from the group consisting of hydroxy, unsubstituted amino, $(C_{1-6})$alkylamino, (di-$(C_{1-6})$alkyl)amino, $(C_{1-6})$alkoxy, and $(C_{1-6})$alkyl.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

In another aspect, the invention is directed to pharmaceutical compositions that comprise an ASK1 inhibitor according to the present invention as an active ingredient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

In another aspect, the invention is directed to kits and articles of manufacture for treating disease states associated with ASK1.

In one embodiment, the kit comprises a composition comprising at least one ASK1 inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another aspect, the invention is directed to articles of manufacture that comprise a composition comprising at least one ASK1 inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The article of manufacture may also optionally comprise additional components, such as syringes for administration of the composition. The article of manufacture may comprise the composition in single or multiple dose forms.

In yet another aspect, the invention is directed to methods for preparing compounds, compositions, kits, and articles of manufacture according to the present invention. For example, several synthetic schemes are provided herein for synthesizing compounds according to the present invention. In still a further aspect, the invention is directed to intermediates useful or preparing compounds, compositions, kits, and articles of manufacture according to the present invention.

In yet another aspect, the invention is directed to methods of using compounds, compositions, kits and articles of manufacture according to the present invention.

In one embodiment, the compounds, compositions, kits and articles of manufacture are used to inhibit ASK1.

In another embodiment, the compounds, compositions, kits and articles of manufacture are used to treat a disease state for which ASK1 possess activity that contributes to the pathology and/or symptomology of the disease state.

In another embodiment, a compound is administered to a subject wherein ASK1 activity within the subject is altered, preferably reduced.

In another embodiment, a prodrug of a compound is administered to a subject that is converted to the compound in vivo where it inhibits ASK1.

In another embodiment, a method of inhibiting ASK1 is provided that comprises contacting an ASK1 with a compound according to the present invention.

In another embodiment, a method of inhibiting ASK1 is provided that comprises causing a compound according to the present invention to be present in a subject in order to inhibit ASK1 in vivo.

In another embodiment, a method is provided for using a compound according to the present invention in order to manufacture a medicament for use in the treatment of a disease state that is known to be mediated by ASK1, or that is known to be treated by ASK1 inhibitors.

It is noted that in the various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting ASK1 and thus may themselves be prodrugs for another compound. Such prodrugs of another compound may or may not themselves independently have ASK1 inhibitory activity.

BRIEF DESCRIPTION OF THE FIGURES

FIG. 1 illustrates SEQ ID NO:1 and SEQ ID NO: 2 referred to in this application.

DEFINITION

Unless otherwise stated, the following terms used in the specification and claims shall have the following meanings for the purposes of this application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY 5$^{TH}$ ED." Vols. A (2007) and B (2007), Springer Science and Business Media, New York. Also, unless otherwise indicated, conventional methods of mass spectroscopy, NMR, HPLC, protein chemistry, biochemistry, recombinant DNA techniques and pharmacology, within the skill of the art are employed.

"Acetyl" means the radical —C(O)CH$_3$.

"Acetylamino" means the radical —NR—C(O)CH3 where R is hydrogen or a further substituent.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with (C$_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a (C$_{2-20}$)alkenyl, a (C$_{2-15}$)alkenyl, a (C$_{2-10}$)alkenyl, a (C$_{2-5}$)alkenyl or a (C$_{2-3}$)alkenyl. Alternatively, "alkenyl," either alone or represented along with another radical, can be a (C$_2$)alkenyl, a (C$_3$)alkenyl or a (C$_4$)alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another." radical, can be a (C$_{2-20}$) alkenylene, a (C$_{2-15}$)alkenylene, a (C$_{2-10}$)alkenylene, a (C$_{2-5}$)alkenylene or a (C$_{2-3}$) alkenylene. Alternatively, "alkenylene," either alone or represented along with another radical, can be a (C$_2$)alkenylene, a (C$_3$)alkenylene or a (C$_4$)alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). (C$_X$)alkyl and (C$_{X-Y}$)alkyl are typically used where X and Y indicate the number of carbon atoms in the chain. For example, (C$_{1-6}$)alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., (C$_{6-10}$)aryl(C$_{1-3}$)alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a (C$_{1-20}$)alkyl, a (C$_{1-15}$)alkyl, a (C$_{1-10}$)alkyl, a (C$_{1-5}$)alkyl or a (C$_{1-3}$)alkyl. Alternatively, "alkyl," either alone or represented along with another radical, can be a (C$_1$)alkyl, a (C$_2$)alkyl or a (C$_3$)alkyl.

"Alkylene", unless indicated otherwise, means a straight or branched, saturated or unsaturated, aliphatic, divalent radical. (C$_X$)alkylene and (C$_{X-Y}$)alkylene are typically used where X and Y indicate the number of carbon atoms in the chain. For example, (C$_{1-6}$)alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—), and the like. In particular embodiments, "alkylene," either alone or represented along with another radical, can be a (C$_{1-20}$)alkylene, a (C$_{1-15}$)alkylene, a (C$_{1-10}$)alkylene, a (C$_{1-5}$)alkylene or a (C$_{1-3}$)alkylene. Alternatively, "alkylene," either alone or represented along with another radical, can be a (C$_1$)alkylene, a (C$_2$)alkylene or a (C$_3$)alkylene.

"Alkylidene" means a straight or branched, saturated or unsaturated, aliphatic radical connected to the parent molecule by a double bond. (C$_X$)alkylidene and (C$_{X-Y}$)alkylidene are typically used where X and Y indicate the number of carbon atoms in the chain. For example, (C$_{1-6}$)alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like. In particular embodiments, "alkylidene," either alone or represented along with another radical, can be a (C$_{1-20}$)alkylidene, a (C$_{1-15}$)alkylidene, a (C$_{1-10}$)alkylidene, a (C$_{1-5}$)alkylidene or a (C$_{1-3}$)alkylidene. Alternatively, "alkylidene," either alone or represented along with another radical, can be a (C$_1$)alkylidene, a (C$_2$)alkylidene or a (C$_3$)alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a (C$_{2-20}$)alkynyl, a (C$_{2-15}$)alkynyl, a (C$_{2-10}$)alkynyl, a (C$_{2-5}$)alkynyl or a (C$_{2-3}$)alkynyl. Alternatively, "alkynyl," either alone or represented along with another radical, can be a (C$_2$)alkynyl, a (C$_3$)alkynyl or a (C$_4$)alkynyl.

"Alkynylene" means a straight or branched, divalent carbon chain having one or more carbon-carbon triple bonds (—C≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a (C$_{2-20}$)alkynylene, a (C$_{2-15}$)alkynylene, a (C$_{2-10}$)alkynylene, a (C$_{2-5}$)alkynylene or a $(C_{2-3})$alkynylene. Alternatively, "alkynylene," either alone or represented along with another radical, can be a $(C_2)$alkynylene, a $(C_3)$ alkynylene or a $(C_4)$alkynylene.

"Amido" means the radical —NR—C(=O)— and/or —NR—C(=O)R', wherein each R and R' are independently hydrogen or a further substituent.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH(($C_{1-10}$)alkyl), —N(($C_{1-10}$)alkyl)$_2$, —NH(aryl), —NH(heteroaryl), —N(aryl)$_2$, —N(heteroaryl)$_2$, and the like. It is further understood that the two substituents may not be taken together with the nitrogen to which the substituents are attached to form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl., a $(C_9)$aryl or a $(C_{10})$aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a $(C_{1-10})$azaalkyl refers to a chain comprising between 1 and 10 carbons and one or more nitrogen atoms.

"Aza-cyclyl" means a heterocyclyl moiety containing at least one nitrogen atom and the point of attachment of the cyclyl is through the nitrogen atom.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" or "aminocarbonyloxy" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxamido" means the radical —C(=O)—NR— and/or —C(=O)—NRR', wherein each R and R' are independently hydrogen or a further substituent.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene., a $(C_9)$cycloalkylene or a $(C_{10})$cycloalkylene.

"Cyclyl" means a monocyclic, bicyclic or polycyclic monovalent ring radical where the ring may be aromatic, saturated or partially unsaturated, and polycyclic, wherein the ring atoms are all carbon atoms or optionally one or more of the ring atoms are heteroatoms.

"Disease" specifically includes any unhealthy condition of an animal or part thereof and includes an unhealthy condition that may be caused by, or incident to, medical or veterinary therapy applied to that animal, i.e., the "side effects" of such therapy.

"$EC_{50}$" means the molar concentration of an agonist that produces 50% of the maximal possible effect of that agonist. The action of the agonist may be stimulatory or inhibitory.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this application, provided that one or more of the atoms within the alkyl chain is a heteroatom. In particular embodiments, "heteroalkyl," either alone or represented along with another radical, can be a hetero($C_{1-20}$)alkyl, a hetero($C_{1-15}$)alkyl, a hetero($C_{1-10}$)alkyl, a hetero($C_{1-5}$)alkyl, a hetero($C_{1-3}$)alkyl or a hetero($C_{1-2}$)alkyl. Alternatively, "heteroalkyl," either alone or represented along with another radical, can be a hetero($C_1$)alkyl, a hetero($C_2$)alkyl or a hetero($C_3$)alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-c]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2 (1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(=O$^-$)—, —O—, —S— or —S(O)$_2$—, wherein R is hydrogen or a further substituent.

"Heterobicycloalkyl" means bicycloalkyl, as defined in this application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this application, provided that one or more of the atoms within the ring is a heteroatom. For example, hetero($C_{4-12}$)bicycloaryl as used in this application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$) bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$) bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this application, provided that one or more of the atoms forming the ring is a heteroatom selected, independently from N, O, or S, Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this application, provided that one or more of the ring member carbon atoms is replaced by a heteroatom. In particular embodiments, "heterocycloalkylene," either alone or represented along with another radical, can be a hetero($C_{1-13}$) cycloalkylene, a hetero($C_{1-9}$)cycloalkylene, a hetero($C_{1-6}$) cycloalkylene, a hetero($C_{5-9}$)cycloalkylene or a hetero($C_{2-6}$) cycloalkylene. Alternatively, "heterocycloalkylene," either alone or represented along with another radical, can be a hetero($C_2$)cycloalkylene, a hetero($C_3$)cycloalkylene, a hetero ($C_4$)cycloalkylene, a hetero($C_5$)cycloalkylene, a hetero($C_6$)cycloalkylene, hetero($C_7$)cycloalkylene, hetero($C_8$)cycloalkylene or a hetero($C_9$)cycloalkylene.

"Heterocyclyl" means a monocyclic, bicyclic or polycyclic monovalent ring radical where the ring may be aromatic, saturated or partially unsaturated, and polycyclic, wherein at least one of the ring atoms is a heteroatom.

"Hydroxy" means the radical —OH.

"$IC_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Iminoketone derivative" means a derivative comprising the moiety —C(NR)—, wherein R is hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 5th edition, March, Jerry, John Wiley & Sons, New York, 2001).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Nitro" means the radical —$NO_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid, or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Phosphonyl" means "the radical —P(O)(OR)(OR'), wherein R and R' are hydrogen or a further substituent. It is noted that the phosphonyl radical may be further substituted with a variety of substituents to form different phosphonyl groups including phosphonice acids and phosphate esters, and sulfones.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in P. G. M. Wuts and T. W. Greene, "*Greene's Protecting Groups in Organic Synthesis,* 4th edition, John Wiley & Sons, Inc. 2007.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, ($C_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, phosphonyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, phosphonyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicyclo aryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl.

"Sulfamoyl," means the radical —$OS(O)_2NRR'$, wherein R and R' are each independently hydrogen or further substituents.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonamido" means the radical —$S(O)_2$—NR— and/or —$S(O)_2$—NRR', —NR—$S(O)_2$— and/or —NR—$S(O)_2R'$, wherein each R and R' are independently hydrogen or a further substituent.

"Sulfonyl" means the radical —$SO_2$— and/or —$SO_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio($C_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Ureido" means the radicals —NR—C(O)—NR'— and/or —N—C(O)—N—R", wherein R, R' and R' are independently hydrogen or a further substituent. It is noted that the ureido radical may be further substituted with a variety of substituents to form different uredio groups.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a ($C_1$)alkyl comprises methyl (i.e., —$CH_3$) as well as —CRR'R" where R, R', and R" may each independently be hydrogen or a further substituent where the atom attached to the carbon is a heteroatom or cyano. Hence, CF$_3$, CH$_2$OH and CH$_2$CN, for example, are all (C$_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

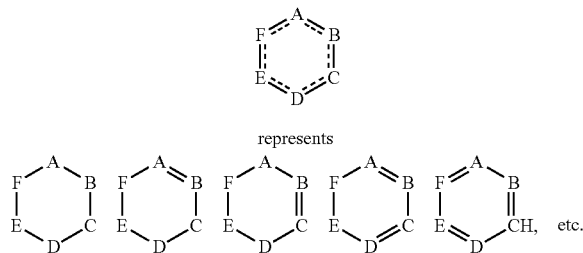

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

DETAILED DESCRIPTION OF THE INVENTION

The present invention relates to compounds that may be used to inhibit ASK1. The present invention also relates to pharmaceutical compositions, kits and articles of manufacture comprising such compounds. In addition, the present invention relates to methods and intermediates useful for making the compounds. Further, the present invention relates to methods of using said compounds.

It is noted that the compounds of the present invention may also possess activity for other members of the same protein family and thus may be used to address disease states associated with these other family members.

Compounds of the Invention

In one of its aspects, the present invention relates to compounds that are useful as ASK1 inhibitors.

In one embodiment, ASK1 inhibitors of the present invention have the formula:

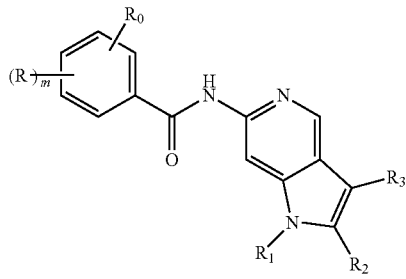

or stereoisomers, or pharmaceutically acceptable salts, thereof, wherein m is 0, 1, or 2;

R$_0$ is a substituted or unsubstituted hydroxy(C$_{1-6}$)alkyl or a substituted or unsubstituted R$_4$-carbonyl(C$_{1-6}$)alkyl;

each R is independently selected from the group consisting of hydroxy, nitro, halo, cyano, (C$_{1-6}$)alkoxy, (C$_{4-6}$)aryloxy, hetero(C$_{1-5}$)aryloxy, (C$_{1-6}$)alkyl, amino(C$_{1-6}$)alkyl, halo(C$_{1-6}$)alkyl, (C$_{4-6}$)aryl(C$_{1-3}$)alkyl, hetero(C$_{1-5}$)aryl(C$_{1-3}$)alkyl, (C$_{3-6}$)cycloalkyl, hetero(C$_{1-5}$)cycloalkyl, (C$_{4-6}$)aryl, and hetero(C$_{1-5}$)aryl, each unsubstituted or substituted with 1-3 substituents each of which is independently selected from the group consisting of hydroxy, halo, (C$_{1-6}$)alkoxy, halo(C$_{1-6}$)alkoxy, amino, (C$_{1-6}$)alkyl, hydroxy(C$_{1-6}$)alkyl, halo(C$_{1-6}$)alkyl, perhalo(C$_{1-6}$)alkyl, amino(C$_{1-6}$)alkyl, hydroxy(C$_{1-6}$)alkoxy, halo(C$_{1-6}$)alkoxy, perhalo(C$_{1-6}$)alkoxy, (C$_{3-6}$)cycloalkyl, R$_9$-carbonyl(C$_{1-6}$)alkyl, R$_9$-sulfonyl(C$_{1-6}$)alkyl, R$_9$-carbonyl, and R$_9$-sulfonyl;

R$_1$ is selected from the group consisting of cyano, (C$_{1-6}$)alkyl, (C$_{2-6}$)alkenyl, (C$_{3-6}$)cycloalkyl, hetero(C$_{1-5}$)cycloalkyl, (C$_{4-6}$)cycloalkenyl, (C$_{4-6}$)cycloalkenyl, sulfonyl, hetero(C$_{3-5}$)cycloalkenyl, (C$_{4-6}$)aryl, and hetero(C$_{1-5}$)aryl, each unsubstituted or substituted with 1-3 substituents each of which is independently selected from the group consisting of hydroxy, halo, cyano, amino, carbonylamino, sulfonylamino, (C$_{3-6}$)cycloalkyl, (C$_{4-6}$)aryl, oxycarbonyl, hydroxycarbonyl, aminocarbonyl, sulfonyl, aminosulfonyl, wherein the amino, carbonylamino, sulfonylamino, oxycarbonyl, aminocarbonyl, sulfonyl, and aminosulfonyl are each unsubstituted or further substituted with 1-2 substituents independently selected from the group consisting of (C$_{1-6}$)alkyl, halo (C$_{1-6}$)alkyl, perhalo(C$_{1-6}$)alkyl, and (C$_{3-6}$)cycloalkyl;

R$_2$ is selected from the group consisting of hydrogen, halo, nitro, cyano, thio, oxy, hydroxy, carbonyloxy, (C$_{1-6}$)alkoxy, (C$_{4-6}$)aryloxy, hetero(C$_{1-5}$)aryloxy, carbonyl, oxycarbonyl, aminocarbonyl, sulfonyl, sulfinyl, (C$_{1-6}$)alkyl, halo(C$_{1-6}$)alkyl, hydroxy(C$_{1-6}$)alkyl, carbonyl(C$_{1-6}$)alkyl, thiocarbonyl (C$_{1-6}$)alkyl, sulfonyl(C$_{1-6}$)alkyl, sulfinyl(C$_{1-6}$)alkyl, (C$_{3-6}$)cycloalkyl(C$_{1-3}$)alkyl, hetero(C$_{1-5}$)cycloalkyl(C$_{1-3}$)alkyl, (C$_{4-6}$)aryl(C$_{1-3}$)alkyl, hetero(C$_{1-5}$)aryl(C$_{1-3}$)alkyl, hetero(C$_{1-5}$)alkyl, (C$_{3-6}$)cycloalkyl, hetero(C$_{1-5}$)cycloalkyl, (C$_{4-6}$)aryl, and hetero(C$_{1-5}$)aryl, each unsubstituted or substituted with 1-3 substituents each of which is independently selected from the group consisting of hydroxy, unsubstituted amino, mono-substituted amino, di-substituted amino, (C$_{1-6}$)alkyl, halo(C$_{1-6}$)alkyl, (C$_{3-6}$)cycloalkyl and (C$_{4-6}$)aryl, provided when R$_3$ is hydrogen and R$_1$ is alkyl, R$_2$ is not aryl, heteroaryl, or heterocyclic;

R$_3$ is selected from the group consisting of hydrogen, halo, nitro, cyano, thio, oxy, hydroxy, carbonyloxy, (C$_{1-6}$)alkoxy, (C$_{4-6}$)aryloxy, hetero(C$_{1-5}$)aryloxy, carbonyl, oxycarbonyl, aminocarbonyl, sulfonyl, sulfinyl, (C$_{1-6}$)alkyl, halo(C$_{1-6}$)alkyl, hydroxy(C$_{1-6}$)alkyl, carbonyl(C$_{1-6}$)alkyl, thiocarbonyl (C$_{1-6}$)alkyl, sulfonyl(C$_{1-6}$)alkyl, sulfinyl(C$_{1-6}$)alkyl, (C$_{3-6}$)cycloalkyl(C$_{1-3}$)alkyl, hetero(C$_{1-5}$)cycloalkyl(C$_{1-3}$)alkyl, (C$_{4-6}$)aryl(C$_{1-3}$)alkyl, hetero(C$_{1-5}$)aryl(C$_{1-3}$)alkyl, hetero(C$_{1-5}$)alkyl, (C$_{3-6}$)cycloalkyl, hetero(C$_{1-5}$)cycloalkyl, (C$_{4-6}$)aryl, and hetero(C$_{1-5}$)aryl, each unsubstituted or substituted with 1-3 substituents each of which is independently selected from the group consisting of hydroxy, halo, (C$_{1-6}$)alkyl, halo(C$_{1-6}$)alkyl, perhalo(C$_{1-6}$)alkyl, (C$_{3-6}$)cycloalkyl, hetero(C$_{1-5}$)cycloalkyl, (C$_{4-6}$)aryl, and hetero(C$_{1-5}$)aryl;

R$_4$ is selected from the group consisting of hydroxy, unsubstituted amino, (C$_{1-6}$)alkylamino, (di-(C$_{1-6}$)alkyl)amino, (C$_{1-6}$)alkoxy, and (C$_{1-6}$)alkyl; and R$_9$ is selected from the group consisting of hydroxy, unsubstituted amino, (C$_{1-6}$)alkylamino, (di-(C$_{1-6}$)alkyl)amino, (C$_{1-6}$)alkoxy, and (C$_{1-6}$)alkyl.

In one variation of the above embodiment, the ASK1 inhibitors of the present invention have the formula:

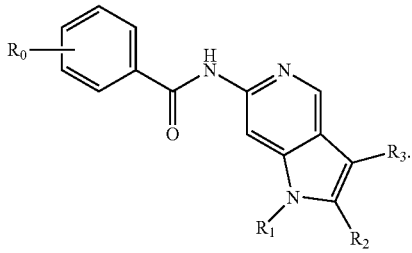

In another variation of the above embodiment, the ASK1 inhibitors of the present invention have the formula:

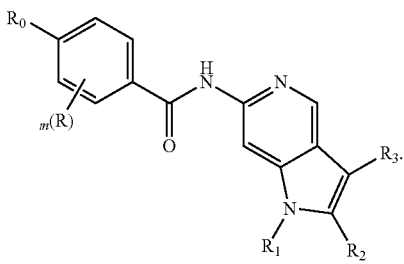

In still another variation of the above embodiment, the ASK1 inhibitors of the present invention have the formula:

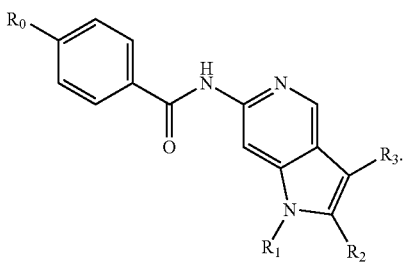

In yet another variation of the above embodiment, the ASK1 inhibitors of the present invention have the formula:

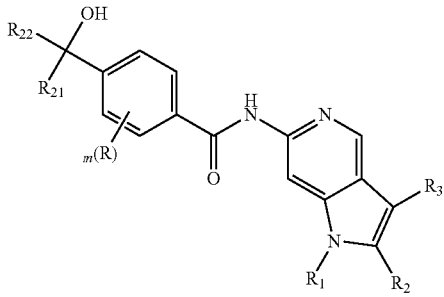

wherein $R_{21}$ is selected from the group consisting of $—C(R_{23})_3$, $—(CR_{23}R_{23'})_p—C(R_{23})_3$, $—(CR_{23}R_{23'})_pOH$, $—(CR_{23}R_{23'})_pC(O)R_{10}$, $—(CR_{23}R_{23'})_pS(O)_2R_{10}$, and $—O(CR_{23}R_{23'})_pOH$, $R_{10}$ is selected from the group consisting of hydroxy, unsubstituted amino, $(C_{1-6})$alkylamino, (di-$(C_{1-6})$alkyl) amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In a further variation of the above embodiment, the ASK1 inhibitors of the present invention have the formula:

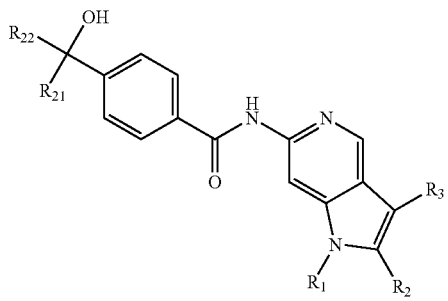

wherein $R_{21}$ is selected from the group consisting of $—C(R_{23})_3$, $—(CR_{23}R_{23'})_p—C(R_{23})_3$, $—(CR_{23}R_{23'})_pOH$, $—(CR_{23}R_{23'})_pC(O)R_{10}$, $—(CR_{23}R_{23'})_pS(O)_2R_{10}$, and $—O(CR_{23}R_{23'})_pOH$, $R_{10}$ is selected from the group consisting of hydroxy, unsubstituted amino, $(C_{1-6})$alkylamino, (di-$(C_{1-6})$alkyl) amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In still a further variation of the above embodiment, the ASK1 inhibitors of the present invention have the formula:

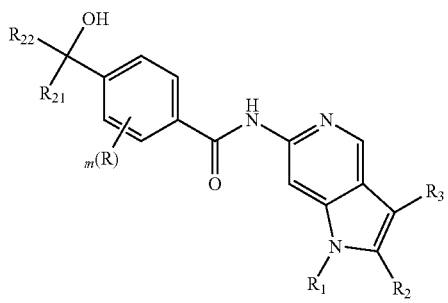

wherein $R_{21}$ is selected from the group consisting of $—C(R_{23})_3$, $—(CR_{23}R_{23'})_p—C(R_{23})_3$, $—(CR_{23}R_{23'})_pOH$, $—(CR_{23}R_{23'})_pC(O)R_{10}$, $—(CR_{23}R_{23'})_pS(O)_2R_{10}$, and $—O(CR_{23}R_{23'})_pOH$, $R_{10}$ is selected from the group consisting of hydroxy, unsubstituted amino, $(C_{1-6})$alkylamino, (di-$(C_{1-6})$alkyl) amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In yet a further variation of the above embodiment, the ASK1 inhibitors of the present invention have the formula:

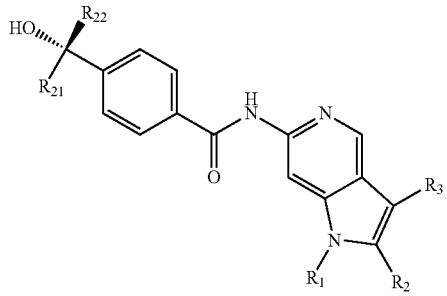

wherein $R_{21}$ is selected from the group consisting of —$C(R_{23})_3$, —$(CR_{23}R_{23'})_p$—$C(R_{23})_3$, —$(CR_{23}R_{23'})_p$OH, —$(CR_{23}R_{23'})_pC(O)R_{10}$, —$(CR_{23}R_{23'})_pS(O)_2R_{10}$, and —$O(CR_{23}R_{23'})_p$OH, $R_{10}$ is selected from the group consisting of hydroxy, unsubstituted amino, $(C_{1-6})$alkylamino, (di-$(C_{1-6})$alkyl) amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$ alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In another variation of the above embodiment, the ASK1 inhibitors of the present invention have the formula:

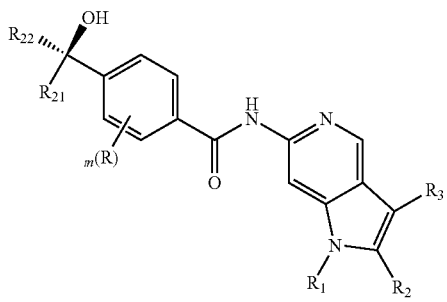

wherein $R_{21}$ is selected from the group consisting of —$C(R_{23})_3$, —$(CR_{23}R_{23'})_p$—$C(R_{23})_3$, —$(CR_{23}R_{23'})_p$OH, —$(CR_{23}R_{23'})_pC(O)R_{10}$, —$(CR_{23}R_{23'})_pS(O)_2R_{10}$, and —$O(CR_{23}R_{23'})_p$OH, $R_{10}$ is selected from the group consisting of hydroxy, unsubstituted amino, $(C_{1-6})$alkylamino, (di-$(C_{1-6})$alkyl) amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$ alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In still another variation of the above embodiment, the ASK1 inhibitors of the present invention have the formula:

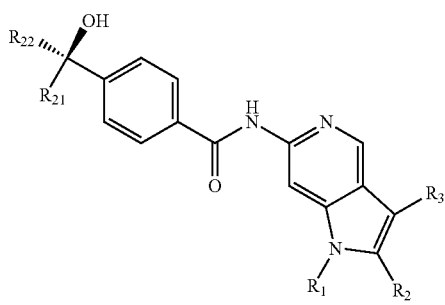

wherein $R_{21}$ is selected from the group consisting of —$C(R_{23})_3$, —$(CR_{23}R_{23'})_p$—$C(R_{23})_3$, —$(CR_{23}R_{23'})_p$OH, —$(CR_{23}R_{23'})_pC(O)R_{10}$, —$(CR_{23}R_{23'})_pS(O)_2R_{10}$, and —$O(CR_{23}R_{23'})_p$OH, $R_{10}$ is selected from the group consisting of hydroxy, unsubstituted amino, $(C_{1-6})$alkylamino, (di-$(C_{1-6})$alkyl) amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$ alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In yet another variation of the above embodiment, the ASK1 inhibitors of the present invention have the formula:

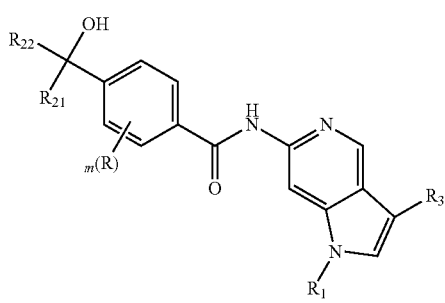

wherein $R_{21}$ is selected from the group consisting of —$C(R_{23})_3$, —$(CR_{23}R_{23'})_p$—$C(R_{23})_3$, —$(CR_{23}R_{23'})_p$OH, —$(CR_{23}R_{23'})_pC(O)R_{10}$, —$(CR_{23}R_{23'})_pS(O)_2R_{10}$, and —$O(CR_{23}R_{23'})_p$OH, $R_{10}$ is selected from the group consisting of hydroxy, unsubstituted amino, $(C_{1-6})$alkylamino, (di-$(C_{1-6})$alkyl) amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$ alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In a further variation of the above embodiment, the ASK1 inhibitors of the present invention have the formula:

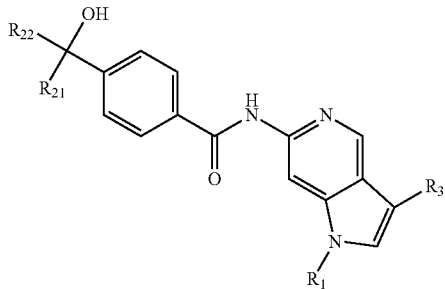

wherein $R_{21}$ is selected from the group consisting of —C($R_{23}$)$_3$, —(C$R_{23}R_{23'}$)$_p$—C($R_{23}$)$_3$, —(C$R_{23}R_{23'}$)$_p$OH, —(C$R_{23}R_{23'}$)$_p$C(O)$R_{10}$, —(C$R_{23}R_{23'}$)$_p$S(O)$_2R_{10}$, and —O(C$R_{23}R_{23'}$)$_p$OH, $R_{10}$ is selected from the group consisting of hydroxy, unsubstituted amino, (C$_{1-6}$)alkylamino, (di-(C$_{1-6}$)alkyl) amino, (C$_{1-6}$)alkoxy, and (C$_{1-6}$)alkyl;

$R_{22}$ is selected from the group consisting of hydrogen, hydroxy, (C$_{1-6}$)alkyl, hydroxy(C$_{1-6}$)alkyl and halo(C$_{1-6}$)alkyl, each substituted or unsubstituted;

$R_{23}$ and $R_{23'}$ are each independently selected from the group consisting of hydrogen, halo, hydroxy, (C$_{1-6}$)alkyl, and (C$_{1-6}$)cycloalkyl, each substituted or unsubstituted; and p is 0, 1, 2, 3, or 4.

In still a further variation of the above embodiment, the ASK1 inhibitors of the present invention have the formula:

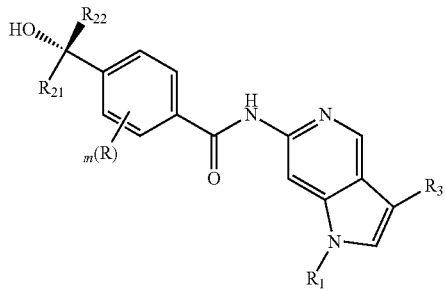

wherein $R_{21}$ is selected from the group consisting of —C($R_{23}$)$_3$, —(C$R_{23}R_{23'}$)$_p$—C($R_{23}$)$_3$, —(C$R_{23}R_{23'}$)$_p$OH, —(C$R_{23}R_{23'}$)$_p$C(O)$R_{10}$, —(C$R_{23}R_{23'}$)$_p$S(O)$_2R_{10}$, and —O(C$R_{23}R_{23'}$)$_p$OH, $R_{10}$ is selected from the group consisting of hydroxy, unsubstituted amino, (C$_{1-6}$)alkylamino, (di-(C$_{1-6}$)alkyl) amino, (C$_{1-6}$)alkoxy, and (C$_{1-6}$)alkyl;

$R_{22}$ is selected from the group consisting of hydrogen, hydroxy, (C$_{1-6}$)alkyl, hydroxy(C$_{1-6}$)alkyl and halo(C$_{1-6}$)alkyl, each substituted or unsubstituted;

$R_{23}$ and $R_{23'}$ are each independently selected from the group consisting of hydrogen, halo, hydroxy, (C$_{1-6}$)alkyl, and (C$_{1-6}$)cycloalkyl, each substituted or unsubstituted; and p is 0, 1, 2, 3, or 4.

In yet a further variation of the above embodiment, the ASK1 inhibitors of the present invention have the formula:

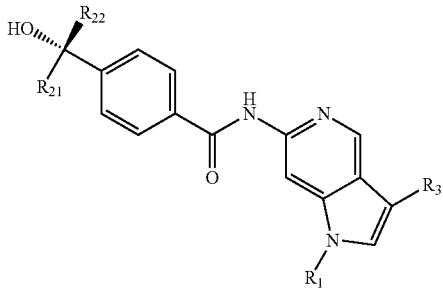

wherein $R_{21}$ is selected from the group consisting of —C($R_{23}$)$_3$, —(C$R_{23}R_{23'}$)$_p$—C($R_{23}$)$_3$, —(C$R_{23}R_{23'}$)$_p$OH, —(C$R_{23}R_{23'}$)$_p$C(O)$R_{10}$, —(C$R_{23}R_{23'}$)$_p$S(O)$_2R_{10}$, and —O(C$R_{23}R_{23'}$)$_p$OH, $R_{10}$ is selected from the group consisting of hydroxy, unsubstituted amino, (C$_{1-6}$)alkylamino, (di-(C$_{1-6}$)alkyl) amino, (C$_{1-6}$)alkoxy, and (C$_{1-6}$)alkyl;

$R_{22}$ is selected from the group consisting of hydrogen, hydroxy, (C$_{1-6}$)alkyl, hydroxy(C$_{1-6}$)alkyl and halo(C$_{1-6}$)alkyl, each substituted or unsubstituted;

$R_{23}$ and $R_{23'}$ are each independently selected from the group consisting of hydrogen, halo, hydroxy, (C$_{1-6}$)alkyl, and (C$_{1-6}$)cycloalkyl, each substituted or unsubstituted; and p is 0, 1, 2, 3, or 4.

In another variation of the above embodiment, the ASK1 inhibitors of the present invention have the formula:

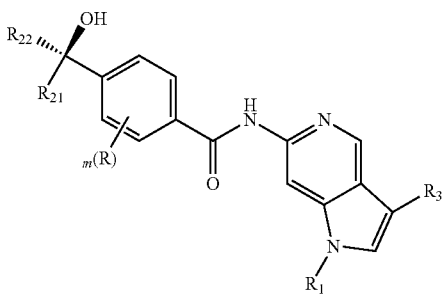

wherein $R_{21}$ is selected from the group consisting of —C($R_{23}$)$_3$, —(C$R_{23}R_{23'}$)$_p$—C($R_{23}$)$_3$, —(C$R_{23}R_{23'}$)$_p$OH, —(C$R_{23}R_{23'}$)$_p$C(O)$R_{10}$, —(C$R_{23}R_{23'}$)$_p$S(O)$_2R_{10}$, and —O(C$R_{23}R_{23'}$)$_p$OH, $R_{10}$ is selected from the group consisting of hydroxy, unsubstituted amino, (C$_{1-6}$)alkylamino, (di-(C$_{1-6}$)alkyl) amino, (C$_{1-6}$)alkoxy, and (C$_{1-6}$)alkyl;

$R_{22}$ is selected from the group consisting of hydrogen, hydroxy, (C$_{1-6}$)alkyl, hydroxy(C$_{1-6}$)alkyl and halo(C$_{1-6}$)alkyl, each substituted or unsubstituted;

$R_{23}$ and $R_{23'}$ are each independently selected from the group consisting of hydrogen, halo, hydroxy, (C$_{1-6}$)alkyl, and (C$_{1-6}$)cycloalkyl, each substituted or unsubstituted; and p is 0, 1, 2, 3, or 4.

In still another variation of the above embodiment, the ASK1 inhibitors of the present invention have the formula:

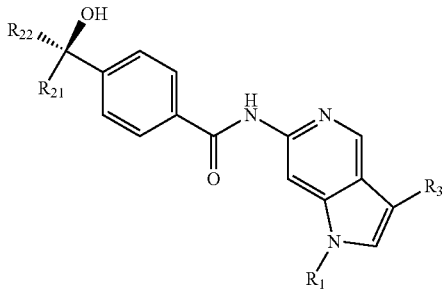

wherein $R_{21}$ is selected from the group consisting of —$C(R_{23})_3$, —$(CR_{23}R_{23'})_p$—$C(R_{23})_3$, —$(CR_{23}R_{23'})_p OH$, —$(CR_{23}R_{23'})_p C(O)R_{10}$, —$(CR_{23}R_{23'})_p S(O)_2 R_{10}$, and —$O(CR_{23}R_{23'})_p OH$, $R_{10}$ is selected from the group consisting of hydroxy, unsubstituted amino, $(C_{1-6})$alkylamino, (di-$(C_{1-6})$alkyl)amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In a further variation of each of the above embodiments and variations, each R is independently selected from the group consisting of hydroxy, nitro, halo, cyano, $(C_{1-6})$alkoxy, $(C_{1-6})$alkyl, amino$(C_{1-6})$alkyl, halo$(C_{1-6})$alkyl, and $(C_{3-6})$cycloalkyl, each unsubstituted or substituted with 1-3 substituents each of which is independently selected from the group consisting of hydroxy, halo, $(C_{1-6})$alkoxy, halo$(C_{1-6})$alkoxy, amino, $(C_{1-6})$alkyl, hydroxy$(C_{1-6})$alkyl, halo$(C_{1-6})$alkyl, perhalo$(C_{1-6})$alkyl, amino$(C_{1-6})$alkyl, hydroxy$(C_{1-6})$alkoxy, halo$(C_{1-6})$alkoxy, perhalo$(C_{1-6})$alkoxy, $(C_{3-6})$cycloalkyl, $R_9$-carbonyl$(C_{1-6})$alkyl, $R_9$-sulfonyl$(C_{1-6})$alkyl, $R_9$-carbonyl, and $R_9$-sulfonyl; and $R_9$ is selected from the group consisting of hydroxy, unsubstituted amino, $C_{1-6}$alkylamino, (di-$C_{1-6}$alkyl)amino, $(C_{1-6})$alkoxy, and $(C_{1-6})$alkyl.

In still a further variation of each of the above embodiments and variations, each R is independently selected from the group consisting of hydroxy, nitro, halo, cyano, $(C_{1-6})$alkoxy, halo$(C_{1-6})$alkoxy, $(C_{1-6})$alkyl, hydroxy$(C_{1-6})$alkyl, amino$(C_{1-6})$alkyl, halo$(C_{1-6})$alkyl, hydroxyhalo$(C_{1-6})$alkyl, and halo$(C_{1-6})$alkoxy$(C_{1-6})$alkyl.

In yet a further variation of each of the above embodiments and variations, each R is independently selected from the group consisting of hydroxy, nitro, halo, cyano, $(C_{1-6})$alkoxy, —$OCHF_2$, —$OCF_3$, $(C_{1-6})$alkyl, hydroxy$(C_{1-6})$alkyl, —$CHF_2$, —$CF_3$, —$C(CH_3)(OH)CF_3$, —$CH_2OCH_2CF_3$, —$C(O)OCH_3$, —$OCH(CH_3)_2$, amino$(C_{1-6})$alkyl, hydroxycarbonylamino$(C_{1-6})$alkyl, $(C_{1-6})$alkoxycarbonylamino$(C_{1-6})$alkyl, and $(C_{1-6})$alkylcarbonylamino$(C_{1-6})$alkyl.

In another variation of each of the above embodiments and variations, $R_0$ is

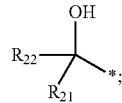

$R_{21}$ is selected from the group consisting of —$C(R_{23})_3$, —$(CR_{23}R_{23'})_p$—$C(R_{23})_3$, —$(CR_{23}R_{23'})_p OH$, —$(CR_{23}R_{23'})_p C(O)R_{10}$, —$(CR_{23}R_{23'})_p S(O)_2 R_{10}$, and —$O(CR_{23}R_{23'})_p OH$, $R_{10}$ is selected from the group consisting of hydroxy, unsubstituted amino, $(C_{1-6})$alkylamino, (di-$(C_{1-6})$alkyl)amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In still another variation of each of the above embodiments and variations, $R_0$ is

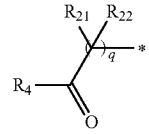

q is 1, 2, 3 or 4;

$R_{21}$ is selected from the group consisting of —$C(R_{23})_3$, —$(CR_{23}R_{23'})_p$—$C(R_{23})_3$, —$(CR_{23}R_{23'})_p OH$, —$(CR_{23}R_{23'})_p C(O)R_{10}$, —$(CR_{23}R_{23'})_p S(O)_2 R_{10}$, and —$O(CR_{23}R_{23'})_p OH$, $R_{10}$ is selected from the group consisting of hydroxy, unsubstituted amino, $(C_{1-6})$alkylamino, (di-$(C_{1-6})$alkyl)amino, $(C_{1-6})$alkoxy, and $(C_{1-6})$alkyl;

$R_{22}$ is selected from the group consisting of hydrogen, hydroxy, $(C_{1-6})$alkyl, hydroxy$(C_{1-6})$alkyl and halo$(C_{1-6})$alkyl, each substituted or unsubstituted;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In yet another variation of each of the above embodiments and variations, $R_0$ is

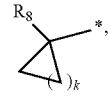

k is 1, 2, 3, or 4;

$R_8$ is —$(CR_{23}R_{23'})_p OH$;

$R_{10}$ is selected from the group consisting of hydroxy, unsubstituted amino, $(C_{1-6})$alkylamino, (di-$(C_{1-6})$alkyl)amino, $(C_{1-6})$alkoxy, and $(C_{1-6})$alkyl;

$R_{23}$ and $R_{23'}$ are each independently selected from the group consisting of hydrogen, halo, hydroxy, $(C_{1-6})$alkyl, and $(C_{1-6})$cycloalkyl, each substituted or unsubstituted; and p is 0, 1, 2, 3, or 4.

In a further variation of each of the above embodiments and variations, $R_0$ is selected from the group consisting of —C(CH$_3$)(CH$_2$OH)OH, —C(CH$_3$)(CH$_2$CH$_2$OH)OH, —C(CH$_3$)(CH(CH$_3$)OH)OH, —C(CH$_3$)(CH(CH$_2$CH$_3$)OH)OH, —C(CH$_3$)(CH(cyclopropyl)OH)OH, —C(CF$_3$)(CH$_2$OH)OH, —C(CF$_3$)(CH$_2$CH$_2$OH)OH, —C(CF$_3$)(CH(CH$_3$)OH)OH, —C(CF$_3$)(CH(CH$_2$CH$_3$)OH)OH, —C(CF$_3$)(CH(cyclopropyl)OH)OH, —CH(CH$_2$OH)OH, —CH(CH$_2$CH$_2$OH)OH, —C(CH$_3$)(C(O)OH)(OH), —C(CH$_3$)(C(O)NH$_2$)(OH), —C(CH$_3$)(S(O)$_2$NH$_2$)(OH), and —C(CH$_3$)(S(O)$_2$NH$_2$)(OH). In still a further variation of each of the above embodiments and variations, Ro is —C(CH$_3$)(CH$_2$OH)OH. In yet a further variation of each of the above embodiments and variations, Ro is —C(CH$_3$)$_2$OH.

In another variation of each of the above embodiments and variations, R$_1$ is selected from the group consisting of cyano, (C$_{1-6}$)alkyl, (C$_{2-6}$)alkenyl, (C$_{3-6}$)cycloalkyl, hydroxy(C$_{1-6}$)alkyl, hydroxy(C$_{2-6}$)alkenyl, dihydroxy(C$_{1-6}$)alkyl, (C$_{3-6}$)cycloalkyl(C$_{1-6}$)alkyl, (C$_{1-6}$)alkylsulfonyl, hydroxycarbonyl(C$_{1-6}$)alkyl, aminocarbonyl(C$_{1-6}$)alkyl, hydroxysulfonyl(C$_{1-6}$)alkyl, and aminosulfonyl(C$_{1-6}$)alkyl, (C$_{1-6}$)alkylcarbonylamino(C$_{1-6}$)alkyl, (C$_{1-6}$)alkylsulfonylamino(C$_{1-6}$)alkyl, wherein the amino of aminocarbonyl(C$_{1-6}$)alkyl, aminosulfonyl(C$_{1-6}$)alkyl, (C$_{1-6}$)alkylcarbonylamino(C$_{1-6}$)alkyl, and (C$_{1-6}$)alkylsulfonylamino(C$_{1-6}$)alkyl are each unsubstituted, or mono- or di-(C$_{1-6}$)alkyl substituted.

In still another variation of each of the above embodiments and variations, R$_1$ is selected from the group consisting of (C$_{1-6}$)alkyl, (C$_{3-6}$)cycloalkyl, (C$_{3-6}$)cycloalkyl(C$_{1-6}$)alkyl and (C$_{1-6}$)alkylsulfonyl(C$_{1-6}$)alkyl, each unsubstituted, or mono- or di-(C$_{1-6}$)alkyl substituted. In yet another variation of each of the above embodiments and variations, R$_1$ is selected from the group consisting of cyano, methyl, ethyl, propyl, isopropyl, butyl, sec-butyl, isobutyl, vinyl, propenyl, butenyl, cyclopropyl, cyclopropylmethyl, phenylmethyl, methylsulfonylmethyl, 2-hydroxypropan-2-yl, and 1,2-dihydroxyethyl. In a further variation of each of the above embodiments and variations, R$_1$ is selected from the group consisting of methyl, ethyl, cyclopropyl, cyclopropylmethyl, and methylsulfonylmethyl, each unsubstituted or substituted with said 1-3 substituents. In still a further variation of each of the above embodiments and variations, R$_1$ is selected from the group consisting of methyl, ethyl, cyclopropyl, cyclopropylmethyl, and methylsulfonylmethyl. In yet a further variation of each of the above embodiments and variations, R$_1$ is selected from the group consisting of methyl and ethyl. In another variation of each of the above embodiments and variations, R$_1$ is cyclopropyl. In still another variation of each of the above embodiments and variations, R$_1$ is selected from the group consisting of methyl, ethyl and cyclopropyl.

In yet another variation of each of the above embodiments and variations, R$_2$ is selected from the group consisting of hydrogen, hydroxy, halo, nitro, cyano, thio, oxy, carbonyloxy, (C$_{1-6}$)alkoxy, (C$_{4-6}$)aryloxy, hetero(C$_{1-5}$)aryloxy, sulfonyl, sulfinyl, (C$_{1-6}$)alkyl, halo(C$_{1-6}$)alkyl, hydroxy(C$_{1-6}$)alkyl, carbonyl(C$_{1-6}$)alkyl, thiocarbonyl(C$_{1-6}$)alkyl, sulfonyl(C$_{1-6}$)alkyl, sulfinyl(C$_{1-6}$)alkyl, (C$_{3-6}$)cycloalkyl(C$_{1-3}$)alkyl, hetero(C$_{1-5}$)cycloalkyl(C$_{1-3}$)alkyl, (C$_{4-6}$)aryl(C$_{1-3}$)alkyl, hetero(C$_{1-5}$)aryl(C$_{1-3}$)alkyl, (C$_{3-6}$)cycloalkyl, and hetero(C$_{1-5}$)cycloalkyl, each unsubstituted or substituted with 1-3 substituents each of which is independently selected from the group consisting of hydroxy, halo, unsubstituted amino, (C$_{1-6}$)alkylamino, (di-(C$_{1-6}$)alkyl)amino, (C$_{1-6}$)alkyl, halo(C$_{1-6}$)alkyl, (C$_{3-6}$)cycloalkyl, and (C$_{4-6}$)aryl.

In a further variation of each of the above embodiments and variations, R$_2$ is selected from the group consisting of hydrogen, halo, (C$_{1-6}$)alkyl, and (C$_{3-6}$)cycloalkyl, where the (C$_{1-6}$)alkyl and (C$_{3-6}$)cycloalkyl are each independently unsubstituted or substituted with 1-3 substituents each of which is independently selected from the group consisting of hydroxy, halo, unsubstituted amino, (C$_{1-6}$)alkylamino, (di-(C$_{1-6}$)alkyl)amino, (C$_{3-6}$)cycloalkyl, and (C$_{4-6}$)aryl. In still a further variation of each of the above embodiments and variations, R$_2$ is selected from the group consisting of hydrogen, hydroxy, halo, cyano, (C$_{1-6}$)alkyl, (C$_{2-6}$)alkenyl, (C$_{3-6}$)cycloalkyl, hydroxy(C$_{1-6}$)alkyl, hydroxy(C$_{2-6}$)alkenyl, dihydroxy(C$_{1-6}$)alkyl, (C$_{3-6}$)cycloalkyl(C$_{1-3}$)alkyl, (C$_{1-6}$)alkylsulfonyl, hydroxycarbonyl(C$_{1-6}$)alkyl, aminocarbonyl(C$_{1-6}$)alkyl, hydroxysulfonyl(C$_{1-6}$)alkyl, and aminosulfonyl(C$_{1-6}$)alkyl, wherein the amino of aminocarbonyl(C$_{1-6}$)alkyl and aminosulfonyl(C$_{1-6}$)alkyl are each unsubstituted, or mono- or di-(C$_{1-6}$)alkyl substituted.

In yet a further variation of each of the above embodiments and variations, R$_2$ is selected from the group consisting of cyano, methyl, ethyl, propyl, isopropyl, butyl, sec-butyl, isobutyl, vinyl, propenyl, butenyl, cyclopropyl, cyclopropylmethyl, phenylmethyl, methylsulfonylmethyl, 2-hydroxypropan-2-yl, and 1,2-dihydroxyethyl. In another variation of each of the above embodiments and variations, R$_2$ is selected from the group consisting of hydrogen, halo, cyano, (C$_{1-6}$)alkyl, hydroxy(C$_{1-6}$)alkyl, halo(C$_{1-6}$)alkyl, amino(C$_{1-6}$)alkyl, (C$_{3-6}$)cycloalkyl, and (C$_{3-6}$)cycloalkyl(C$_{1-3}$)alkyl. In still another variation of each of the above embodiments and variations, R$_2$ is halo. In yet another variation of each of the above embodiments and variations, R$_2$ is hydrogen. In a further variation of each of the above embodiments and variations, R$_2$ is cyano. In still a further variation of each of the above embodiments and variations, R$_2$ is (C$_{1-6}$)alkyl, (C$_{3-6}$)cycloalkyl, and (C$_{3-6}$)cycloalkyl(C$_{1-3}$)alkyl.

In yet a further variation of each of the above embodiments and variations, R$_3$ is selected from the group consisting of hydrogen, halo, (C$_{1-6}$)alkyl, (C$_{2-6}$)alkenyl, and (C$_{3-6}$)cycloalkyl, each unsubstituted or substituted with 1-3 substituents each of which is independently selected from the group consisting of hydroxy, halo, (C$_{1-6}$)alkyl, halo(C$_{1-6}$)alkyl, perhalo(C$_{1-6}$)alkyl, (C$_{3-6}$)cycloalkyl, hetero(C$_{1-5}$)cycloalkyl, (C$_{4-6}$)aryl, and hetero(C$_{1-5}$)aryl. In another variation of each of the above embodiments and variations, R$_3$ is selected from the group consisting of hydrogen, halo, (C$_{1-6}$)alkyl, (C$_{3-6}$)cycloalkyl, and (C$_{3-6}$)cycloalkyl(C$_{1-3}$)alkyl. In still a further variation of each of the above embodiments and variations, R$_3$ is selected from the group consisting of hydrogen, chloro, bromo, methyl, ethyl, cyclopropyl, cyclopropylmethyl, and phenylmethyl. In yet a further variation of each of the above embodiments and variations, wherein R$_3$ is (C$_{1-6}$)alkyl. In another variation of each of the above embodiments and variations, R$_3$ is hydrogen. In still another variation of each of the above embodiments and variations, R$_3$ is halo. In yet another variation of each of the above embodiments and variations, R$_3$ is chloro. In a further variation of each of the above embodiments and variations, R$_3$ is bromo. In still a further variation of each of the above embodiments and variations, R$_3$ is methyl.

In yet a further variation of each of the above embodiments and variations:

R$_1$ is selected from the group consisting of (C$_{1-6}$)alkyl, (C$_{3-6}$)cycloalkyl, (C$_{3-6}$)cycloalkyl(C$_{1-3}$)alkyl, and (C$_{1-3}$)alkylsulfonyl(C$_{1-3}$)alkyl;

R$_2$ is selected from the group consisting of hydrogen, hydroxy, halo, cyano, (C$_{1-6}$)alkyl, (C$_{2-6}$)alkenyl, (C$_{3-6}$)cycloalkyl, hydroxy(C$_{1-6}$)alkyl, hydroxy(C$_{2-6}$)alkenyl, dihydroxy(C$_{1-6}$)alkyl, (C$_{3-6}$)cycloalkyl(C$_{1-3}$)alkyl, (C$_{1-6}$)alkylsulfonyl, hydroxycarbonyl(C$_{1-6}$)alkyl, aminocarbonyl(C$_{1-6}$)alkyl, hydroxysulfonyl(C$_{1-6}$)alkyl, and aminosulfonyl(C$_{1-6}$)alkyl; and $R_3$ is selected from the group consisting of hydrogen, halo, and $(C_{1-6})$alkyl.

In another variation of each of the above embodiments and variations, $R_4$ is selected from the group consisting of hydroxy, $(C_{1-6})$alkyl, unsubstituted amino, $(C_{1-6})$alkylamino, and (di-$(C_{1-6})$alkyl)amino.

In still another variation of each of the above embodiments and variations, $R_8$ is —$CH_2OH$.

In yet another variation of each of the above embodiments and variations, wherein $R_9$ is selected from the group consisting of hydroxy, $(C_{1-6})$alkyl, unsubstituted amino, $(C_{1-6})$alkylamino, and (di-$(C_{1-6})$alkyl)amino.

In a further variation of each of the above embodiments and variations, $R_{10}$ is selected from the group consisting of hydroxy, $(C_{1-6})$alkyl, unsubstituted amino, $(C_{1-6})$alkylamino, and (di-$(C_{1-6})$alkyl)amino.

In still a further variation of each of the above embodiments and variations, $R_{21}$ is selected from the group consisting of hydroxyl, $(C_{1-6})$alkyl and hydroxy$(C_{1-6})$alkyl, each substituted or unsubstituted. In another variation of each of the above embodiments and variations, $R_{21}$ is selected from the group consisting of $(C_{1-6})$alkyl and hydroxy$(C_{1-6})$alkyl, each substituted or unsubstituted. In yet a further variation of each of the above embodiments and variations, $R_{21}$ is methyl. In another variation of each of the above embodiments and variations, $R_{21}$ is —$CH_2OH$. In still another variation of each of the above embodiments and variations, $R_{21}$ is —$CH_2CH_2OH$. In yet another variation of each of the above embodiments and variations, $R_{21}$ is hydroxy. In a further variation of each of the above embodiments and variations, $R_{21}$ is selected from the group consisting of —$CH_2OH$, —$CH_2CH_2OH$, —$CH(cyclopropyl)OH$, —$CH(CH_3)OH$, —$CH(CH_2CH_3)OH$, —$O(CH_2)CH(OH)CH_2OH$, —$C(O)OH$, —$C(O)NH_2$, and —$S(O)_2NH_2$. In still another variation of each of the above embodiments and variations, $R_{21}$ is hydroxymethyl.

In yet another variation of each of the above embodiments and variations, $R_{22}$ is selected from the group consisting of hydroxy, $(C_{1-3})$alkyl and hydroxy$(C_{1-3})$alkyl, each substituted or unsubstituted. In a further variation of each of the above embodiments and variations, $R_{22}$ is selected from the group consisting of hydrogen, $(C_{1-6})$alkyl, hydroxy$(C_{1-6})$alkyl and halo$(C_{1-6})$alkyl, each substituted or unsubstituted. In another variation of each of the above embodiments and variations, $R_{22}$ is selected from the group consisting of $(C_{1-3})$alkyl and hydroxy$(C_{1-3})$alkyl, each substituted or unsubstituted. In a further variation of each of the above embodiments and variations, $R_{22}$ is hydrogen. In still a further variation of each of the above embodiments and variations, $R_{22}$ is methyl. In yet a further variation of each of the above embodiments and variations, $R_{22}$ is $CF_3$.

In another variation of each of the above embodiments and variations, $R_{23}$ is hydrogen. In still another variation of each of the above embodiments and variations, $R_{23}$ is halo. In still another variation of each of the above embodiments and variations, $R_{23}$ is a substituted or unsubstituted $(C_{1-3})$alkyl. In yet another variation of each of the above embodiments and variations, $R_{23}$ is methyl.

In a further variation of each of the above embodiments and variations, m is 0. In a still further variation of each of the above embodiments and variations, m is 1. In another variation of each of the above embodiments and variations, p is 1, 2, 3 or 4. In yet a further variation of each of the above embodiments and variations, p is 1. In another variation of each of the above embodiments and variations, k is 1. In still another variation of each of the above embodiments and variations, k is 2. In yet another variation of each of the above embodiments and variations, q is 1.

Particular examples of compounds according to the present invention include, but are not limited to:
N-(1-(cyclopropylmethyl)-1H-pyrrolo[3,2-c]pyridin-6-yl)-4-(2-hydroxypropan-2-yl)benzamide;
N-(3-bromo-1-(cyclopropylmethyl)-1H-pyrrolo[3,2-c]pyridin-6-yl)-4-(2-hydroxypropan-2-yl)benzamide;
N-(3-bromo-1-ethyl-1H-pyrrolo[3,2-c]pyridin-6-yl)-4-(2-hydroxypropan-2-yl)benzamide;
N-(1-ethyl-3-methyl-1H-pyrrolo[3,2-c]pyridin-6-yl)-4-(2-hydroxypropan-2-yl)benzamide;
4-(1,2-dihydroxypropan-2-yl)-N-(1-ethyl-1H-pyrrolo[3,2-c]pyridin-6-yl)benzamide;
N-(3-chloro-1-ethyl-1H-pyrrolo[3,2-c]pyridin-6-yl)-4-(1,2-dihydroxypropan-2-yl)benzamide;
N-(3-bromo-1-methyl-1H-pyrrolo[3,2-c]pyridin-6-yl)-4-(2-hydroxypropan-2-yl)benzamide;
N-(3-bromo-1-methyl-1H-pyrrolo[3,2-c]pyridin-6-yl)-4-(1,2-dihydroxypropan-2-yl)benzamide;
N-(1-cyclopropyl-1H-pyrrolo[3,2-c]pyridin-6-yl)-4-(1,2-dihydroxypropan-2-yl)benzamide;
4-(1,2-dihydroxypropan-2-yl)-N-(1-ethyl-3-methyl-1H-pyrrolo[3,2-c]pyridin-6-yl)benzamide;
N-(1,3-dimethyl-1H-pyrrolo[3,2-c]pyridin-6-yl)-4-(2-hydroxypropan-2-yl)benzamide;
N-(3-bromo-1-ethyl-1H-pyrrolo[3,2-c]pyridin-6-yl)-4-(1,2-dihydroxypropan-2-yl)benzamide;
4-(2-hydroxypropan-2-yl)-N-(1-(methylsulfonylmethyl)-1H-pyrrolo[3,2-c]pyridin-6-yl)benzamide;
N-(3-bromo-1-cyclopropyl-1H-pyrrolo[3,2-c]pyridin-6-yl)-4-(1,2-dihydroxypropan-2-yl)benzamide;
N-(3-chloro-1-cyclopropyl-1H-pyrrolo[3,2-c]pyridin-6-yl)-4-(1,2-dihydroxypropan-2-yl)benzamide;
N-(3-chloro-1-methyl-1H-pyrrolo[3,2-c]pyridin-6-yl)-4-(2-hydroxypropan-2-yl)benzamide;
N-(2,3-dichloro-1-methyl-1H-pyrrolo[3,2-c]pyridin-6-yl)-4-(2-hydroxypropan-2-yl)benzamide;
4-(1,2-dihydroxypropan-2-yl)-N-(1-ethyl-1H-pyrrolo[3,2-c]pyridin-6-yl)-3-methylbenzamide;
N-(3-chloro-1-cyclopropyl-1H-pyrrolo[3,2-c]pyridin-6-yl)-4-(1-hydroxy-2-methylpropan-2-yl)benzamide;
N-(3-chloro-1-methyl-1H-pyrrolo[3,2-c]pyridin-6-yl)-4-(1,2-dihydroxypropan-2-yl)benzamide;
N-(2,3-dichloro-1-methyl-1H-pyrrolo[3,2-c]pyridin-6-yl)-4-(1,2-dihydroxypropan-2-yl)benzamide; and
N-(3-chloro-1-ethyl-1H-pyrrolo[3,2-c]pyridin-6-yl)-4-(1,2-dihydroxypropan-2-yl)-3-methylbenzamide.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as hydrogen.

It is further noted that the compound may be present as a mixture of stereoisomers, or the compound may present as a single stereoisomer.

In another of its aspects, there is provided a pharmaceutical composition comprising as an active ingredient a compound according to any one of the above embodiments and variations and a pharmaceutical excipient. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

The present invention also provides a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In still another of its aspects, the present invention relates to medicaments for treating disease state. Particularly, a medicament for treating diseases and conditions which ASK1 possesses activity that contributes to the pathology and/or symptomology of the disease state. More particularly, medicaments for treating the disease states that are described in the methods of using the compounds of the invention.

In a further of its aspects, there is provided a therapeutic method comprising administering a compound of any one of the above embodiments and variations to a subject.

In another of its aspects, there is provided a method of inhibiting ASK1 comprising contacting ASK1 with a compound of any one of the above embodiments and variations.

In yet another of its aspects, there is provided a method of inhibiting ASK1 comprising causing a compound of any one of the above embodiments and variations to be present in a subject in order to inhibit ASK1 in vivo.

In a further of its aspects, there is provided a method of inhibiting ASK1 comprising administering a first compound to a subject that is converted in vivo to a second compound wherein the second compound inhibits ASK1 in vivo, the second compound being a compound according to any one of the above embodiments and variations.

In another of its aspects, there is provided a method of treating a disease state for which ASK1 possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which ASK1 possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which ASK1 possesses activity that contributes to the pathology and/or symptomology of the disease state, the method comprising administering a first compound to a subject that is converted in vivo to a second compound wherein the second compound inhibits ASK1 in vivo, the second compound being a compound according to any one of the above embodiments and variations.

In some variations of each of the above treatment methods, the disease state is selected from the group consisting of metabolic diseases, inflammatory diseases, neurodegenerative diseases, autoimmune diseases, destructive bone disorders, infectious diseases, diseases and conditions that are mediated by inducible pro-inflammatory proteins, reperfusion/ischemia in stroke, cardiac hypertrophy, respiratory diseases, heart attacks, myocardial ischemia, organ hypoxia, vascular hyperplasia, cardiac hypertrophy, hepatic ischemia, liver disease, congestive heart failure, pathologic immune responses, thrombin-induced platelet aggregation, gastroenterological diseases, hematological diseases, and urological diseases.

In some other variations of each of the above treatment methods, the disease state is selected from the group consisting of the disease state is selected from the group consisting of diabetes, type 2 diabetes mellitus, diabetic dyslipidemia, impaired glucose tolerance (IGT), impaired fasting plasma glucose (IFG), metabolic acidosis, ketosis, appetite regulation, obesity and complications associated with diabetes including diabetic neuropathy, diabetic retinopathy, inflammatory bowel disease, Crohn's disease, chemotherapy-induced enteritis, oral mucositis, Shortened Bowel Syndrome, kidney disease, hyperlipidemia, arteriosclerosis; hypertension; myocardial infarction, angina pectoris, cerebral infarction, cerebral apoplexy and metabolic syndrome.

In some other variations of each of the above treatment methods, the disease state is selected from the group consisting of acute pancreatitis, chronic pancreatitis, asthma, allergies, chronic obstructive pulmonary disease, and adult respiratory distress syndrome.

In still some other variations of each of the above treatment methods, the disease state is selected from the group consisting of Alzheimer's disease, Parkinson's disease, amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

In still other variations of each of the above treatment methods, the disease state is selected from the group consisting of glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome.

In still other variations of each of the above treatment methods, the disease state is selected from the group consisting of osteoporosis, osteoarthritis and multiple myeloma-related bone disorder.

In yet still other variations of each of the above treatment methods, the disease state is selected from the group consisting of sepsis, septic shock, and Shigellosis.

In yet still other variations of each of the above treatment methods, the disease state is selected from the group consisting of edema, analgesia, fever and pain, such as neuromuscular pain, headache, cancer pain, dental pain and arthritis pain.

In yet still other variations of each of the above treatment methods, the disease state is selected from the group consisting of ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

Salts, Hydrates, and Prodrugs of ASK1 Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfate, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen containing groups may be quaternized with such agents as $(C_{1-4})$alkyl halides, e.g., methyl, ethyl, iso-propyl and tert-butyl chlorides, bromides and iodides; di $(C_{1-4})$alkyl sulfates, e.g., dimethyl, diethyl and diamyl sulfates; $(C_{10-18})$ alkyl halides, e.g., decyl, dodecyl, lauryl, myristyl and stearyl chlorides, bromides and iodides; and aryl $(C_{1-4})$alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in P. G. M. Wuts and T. W. Greene in "*Greene's Protective Groups in Organic Synthesis*" 4th edition, John Wiley and Sons, 2007.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Uses for the Compounds of the Invention

ASK1 activates the p38 and JNK pro-apoptotic pathways in response to environmental stresses. Wang et al. *J. Biol. Chem.* 1996, 271, 31607-31611; Ichijo et al. *Science* 1997, 275, 90-94. ASK1 induces apoptosis through ASK1-p38/JNK cascades in response to pro-apoptotic stresses (e.g. oxidative stress and TNF) and pathogenic stresses (e.g. ER stress, GPCR- and Aβ-induced ROS production). Overexpression of wild-type or constitutively active ASK1 induces apoptosis in various cells through mitochondria-dependent caspase activation. Saitoh et al *EMBO J.* 1998, 17:2596-2606; Kanamoto et al. *Mol. Cell. Biol.* 2000, 20, 196-204; Hatai et al. *J. Biol. Chem.* 2000, 275, 26576-2658.

Apoptosis plays an essential role in normal development and tissue homeostasis; such that when dysregulated, it contributes to multiple diseases including, but are not limited to, amyloidosis, hypercholesterolemia, diabetes mellitus, cancers, inflammatory diseases, autoimmune diseases, destructive bone disorders, infectious diseases, neurodegenerative diseases, reperfusion/ischemia in stroke, cardiac hypertrophy respiratory diseases, metabolic diseases, gastroenterological diseases, hematological diseases, and urological diseases. Thompson, *Science* 1995, 267, 1456-1462; Yuan and Yanker *Nature* 2000, 407, 802-809; Los et al. *Immunity* 1999, 10, 629-639; Aridor and Balch, *Nat. Med.* 1999, 5, 745-751; Kopito and Ron, *Nat. Cell Biol.* 2000, 2, E207-E209; Nakagawa et al. *Nature* 2000, 403, 98-103; Imai et al. *Cell* 2001, 105, 891-902; Harding et al. *Mol Cell* 2001, 7, 1153-1163; and Nishitoh et al. *Genes Dev.* 2002, 16, 1345-1355.

Recent studies revealed that ASK1 contributes not only to regulation of cell death but also has diverse functions in the decision of cell fate such as cytokine responses, cell differentiation, and innate immune responses. Matsukawa et al. *J Biochem. (Toyko)* 2004, 136, 261-265. Sayama et al. *J. Biol. Chem.* 2000, 276:999-1004; Takeda et al. *J. Biol. Chem.* 2000, 275:9805-9813; Sagasti et al. *Cell* 2001, 105:221-232; Kim at al. *Science* 2002, 297:623-626; Nishitoh et al. *Genes Dev.* 2002, 16:1345-1355; Matsukawa et al. *Nat Immunol* 2005, 6, 587-592; Tobiume et al. *EMBO Rep.* 2001, 2:222-228; Imoto, et al. *Diabetes* 2006, 55:1197-1204. Constitutively active ASK1 induces neurite outgrowth in PC12 cells. ASK1 is activated by CaMKII, which activates ASK1-p38 pathway in neurons, suggesting that ASK1 might play critical roles in synaptic plasticity. Moreover, TRAF6-ASK1-p38 pathway plays an essential role in inflammatory and innate immune responses. Hayakaw et al. *Microbes and Infection* 2006, 8, 1098-1107. It has also been demonstrated that ASK1 has a role in the pathogenesis of TNF-α-induced insulin resistance. Overexpression of wild-type ASK1 increases serine phosphorylation of insulin receptor substrate (IRS)-1, and decreases insulin-stimulated tyrosine phosphorylation of IRS-1, leading to impair insulin signaling. Imoto, et al. *Diabetes* 2006, 55:1197-1204.

Accordingly, modulating the activity of ASK1 by the compounds of the invention would have impact of a multiple of diseases and condition; in particularly, metabolic diseases, inflammatory diseases, neurodegenerative diseases, autoimmune diseases, destructive bone disorders, infectious diseases, diseases and conditions that are mediated by inducible pro-inflammatory proteins, reperfusion/ischemia in stroke, cardiac hypertrophy, respiratory diseases, heart attacks, myocardial ischemia, organ hypoxia, vascular hyperplasia, cardiac hypertrophy, hepatic ischemia, liver disease, congestive heart failure, pathologic immune responses, thrombin-induced platelet aggregation, gastroenterological diseases, hematological diseases, and urological diseases.

Metabolic diseases which may be treated or prevented by the compounds of this invention include, but are not limited to, diabetes, particularly, type 2 diabetes mellitus, diabetic dislipidemia, impaired glucose tolerance (IGT), impaired fasting plasma glucose (IFG), metabolic acidosis, ketosis, appetite regulation, obesity and complications associated with diabetes including diabetic neuropathy, diabetic retinopathy, inflammatory bowel disease, Crohn's disease, chemotherapy-induced enteritis, oral mucositis, Shortened Bowel Syndrome and kidney disease. The conditions mediated by ASK1 inhibitors of the invention further include hyperlipidemia such as hypertriglyceridemia, hypercholesteremia, hypoHDLemia and postprandial hyperlipidemia; arteriosclerosis; hypertension; myocardial infarction, angina pectoris, cerebral infarction, cerebral apoplexy and metabolic syndrome.

Inflammatory diseases which may be treated or prevented by the compounds of this invention include, but are not limited to, acute pancreatitis, chronic pancreatitis, asthma, allergies, chronic obstructive pulmonary disease, adult respiratory distress syndrome.

Neurodegenerative diseases which may be treated or prevented by the compounds of this invention include, but are not limited to, Alzheimer's disease (Nakagawa et al. *Nature* 2000, 403, 98-103), Parkinson's disease (Imai et al. *Cell* 2001, 105, 891-902), amyotrophic lateral sclerosis (ALS), epilepsy, seizures, Huntington's disease, polyglutamine diseases (Nishitoh et al. *Genes Dev.* 2002, 16, 1345-1355), traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome.

Destructive bone disorders which may be treated or prevented by the compounds of this invention include, but are not limited to, osteoporosis, osteoarthritis and multiple myeloma-related bone disorder.

Infectious diseases which may be treated or prevented by the compounds of this invention include, but are not limited to, sepsis, septic shock, and Shigellosis.

Diseases and conditions that are mediated by inducible pro-inflammatory proteins which may be treated or prevented by the compounds of this invention include, but are not limited to, edema, analgesia, fever and pain, such as neuromuscular pain, headache, cancer pain, dental pain and arthritis pain.

Other conditions that are mediated by ASK1 and may be treated or prevented by the compounds of this invention include, but are not limited to, ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation, and thrombin-induced platelet aggregation.

Combination Therapy

A wide variety of therapeutic agents may have a therapeutic additive or synergistic effect with ASK1 inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. It is noted that combination therapy is intended to cover when agents are administered before or after each other (sequential therapy) as well as when the agents are administered at the same time.

The present invention particularly relates to the use of the compounds of the invention in combination with one or more other antidiabetic agents. Examples of such other antidiabetic agents include, but are not limited to insulin signaling pathway modulators, like protein tyrosine phosphatase (PTPase) inhibitors, and glutamine-fructose-6-phosphate amidotransferase (GFAT) inhibitors; compounds influencing a dysregulated hepatic glucose production, like glucose-6-phosphatase (G6Pase) inhibitors, fructose-1,6-bisphosphatase (F-1,6-BPase) inhibitors, glycogen phosphorylase (GP) inhibitors, glucagon receptor antagonists and phosphoenolpyruvate carboxykinase (PEPCK) inhibitors; pyruvate dehydrogenase kinase (PDHK) inhibitors; insulin sensitivity enhancers (insulin sensitizers); insulin secretion enhancers (insulin secretagogues); alpha-glucosidase inhibitors; inhibitors of gastric emptying; glucokinase activators, GLP-1 receptor agonists, GLP-2 receptor agonists, UCP modulators, RXR modulators, GSK-3 inhibitors, PPAR modulators, metformin, insulin; and $\alpha_2$-adrenergic antagonists. ASK1 inhibitors may be administered with such at least one other antidiabetic compound either simultaneously as a single dose, at the same time as separate doses, or sequentially (i.e., where one is administered before or after the other is administered).

Examples of PTPase inhibitors that may be used in combination with ASK1 inhibitors of the invention include, but are not limited to those disclosed in U.S. Pat. Nos. 6,057,316, 6,001,867, and PCT Publication Nos. WO 99/58518, WO 99/58522, WO 99/46268, WO 99/46267, WO 99/46244, WO 99/46237, WO 99/46236, and WO 99/15529.

Examples of GFAT inhibitors that may be used in combination with ASK1 inhibitors of the invention include, but are not limited to those disclosed in Mol. Cell. Endocrinol. 1997, 135(1), 67-77.

Examples of G6Pase inhibitors that may be used in combination with ASK1 inhibitors of the invention include, but are not limited to those disclosed in PCT Publication Nos. WO 00/14090, WO 99/40062 and WO 98/40385, European Patent Publication No. EP682024 and Diabetes 1998, 47, 1630-1636.

Examples of F-1,6-BPase inhibitors that may be used in combination with ASK1 inhibitors of the invention include, but are not limited to those disclosed in PCT Publication Nos. WO 00/14095, WO 99/47549, WO 98/39344, WO 98/39343 and WO 98/39342.

Examples of GP inhibitors that may be used in combination with ASK1 inhibitors of the invention include, but are not limited to those disclosed in U.S. Pat. No. 5,998,463, PCT Publication Nos. WO 99/26659, WO 97/31901, WO 96/39384 and WO9639385 and European Patent Publication Nos. EP 978279 and EP 846464.

Examples of glucagon receptor antagonists that may be used in combination with ASK1 inhibitors of the invention include, but are not limited to those disclosed in U.S. Pat. Nos. 5,880,139 and 5,776,954, PCT Publication Nos. WO 99/01423, WO 98/22109, WO 98/22108, WO 98/21957, WO 97/16442 and WO 98/04528 and those described in *Bioorg Med. Chem. Lett* 1992, 2, 915-918, *J. Med. Chem.* 1998, 41, 5150-5157, and *J. Biol. Chem.* 1999, 274, 8694-8697.

Examples of PEPCK inhibitors that may be used in combination with ASK1 inhibitors of the invention include, but are not limited to those disclosed in U.S. Pat. No. 6,030,837 and *Mol. Biol. Diabetes* 1994, 2, 283-99.

Examples of PDHK inhibitors that may be used in combination with ASK1 inhibitors of the invention include, but are not limited to those disclosed in *J. Med. Chem.* 1999, 42, 2741-2746.

Examples of insulin sensitivity enhancers that may be used in combination with ASK1 inhibitors of the invention include, but are not limited to GSK-3 inhibitors, retinoid X receptor (RXR) agonists, Beta-3 AR agonists, UCP modulators, antidiabetic thiazolidinediones (glitazones), non-glitazone type PPAR gamma agonists, dual PPAR gamma/PPAR alpha agonists, antidiabetic vanadium containing compounds and biguanides such as metformin.

Examples of GSK-3 inhibitors include, but are not limited to those disclosed in PCT Publication Nos. WO 00/21927 and WO 97/41854.

Examples of RXR modulators include, but are not limited to those disclosed in U.S. Pat. Nos. 4,981,784, 5,071,773, 5,298,429 and 5,506,102 and PCT Publication Nos. WO89/05355, WO91/06677, WO92/05447, WO93/11235, WO95/18380, WO94/23068, and WO93/23431.

Examples of Beta-3 AR agonists include, but are not limited to CL-316,243 (Lederle Laboratories) and those disclosed in U.S. Pat. No. 5,705,515 and PCT Publication Nos. WO 99/29672, WO 98/32753, WO 98/20005, WO 98/09625, WO 97/46556, and WO 97/37646.

Examples of UCP modulators include agonists of UCP-1, UCP-2 and UCP-3. Examples of UCP modulators include, but are not limited to those disclosed in Vidal-Puig et al., *Biochem. Biophys. Res. Commun.,* 1997, 235(1), 79-82.

Examples of antidiabetic, PPAR modulating thiazolidinediones (glitazones) include, but are not limited to, (S)-((3,4-dihydro-2-(phenyl-methyl)-2H-1-benzopyran-6-yl) methyl-thiazolidine-2,4-dione (englitazone), 5-{[4-(3-(5-methyl-2-phenyl-4-oxazolyl)-1-oxo-propyl)-phenyl]-methyl}-thiazolidine-2,4-dione (darglitazone), 5-{[4-(1- methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazoly)-ethoxy)]benzyl}-thiazolidine-2,4-dione (BM-13.1246), 542-naphthylsulfonyl)-thiazolidine-2,4-dione (AY-31637), bis{4-[(2,4-dioxo-5-thiazolidinyl)-methyl]phenyl}methane (YM268), 5-{4-[2-(5-methyl-2-phenyl-4-oxazolyl)-2-hydroxyethoxy]-benzyl}-1-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenylmethyl)-thiazolidine-2,4-dione, 5-[3-(4-chloro-phenylp-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}-thiazolidine-2,4-dione (pioglitazone; marketed under the trademark ACTOS™), 5-[6-(2-fluoro-benzyloxy)-naphthalen-2-ylmethyl]-thiazolidine-2,4-dione (MCC555), 5-([2-(2-naphthyl)-benzoxazol-5-yl]-methyl}thiazolidine-2,4-dione (T-174), edaglitazone (BM-13-1258), rivoglitazone (CS-011), and 5-(2,4-dioxothiazolidin-5-ylmethyl)-2-meth-oxy-N-(4-trifluoromethyl-benzyl)benzamide (KRP297).

Examples of non-glitazone type PPAR gamma agonists include, but are not limited to N-(2-benzoylphenyl)-L-tyrosine analogues, such as GI-262570, reglixane (JTT501), and FK-614 and metaglidasen (MBX-102).

Examples of dual PPAR gamma/PPAR alpha agonists include, but are not limited to omega.-[(oxoquinazolinyla-lkoxy)phenyl]alkanoates and analogs thereof including those described in PCT Publication No. WO 99/08501 and *Diabetes* 2000, 49(5), 759-767; tesaglitazar, muraglitazar, and naveglitazar.

Examples of antidiabetic vanadium containing compounds include, but are not limited to those disclosed in the U.S. Pat. No. 5,866,563.

Metformin (dimethyldiguanide) and its hydrochloride salt is marketed under the trademark GLUCOPHAGE™.

Examples of insulin secretion enhancers include but are not limited to glucagon receptor antagonists (as described above), sulphonyl urea derivatives, incretin hormones or mimics thereof, especially glucagon-like peptide-1 (GLP-1) or GLP-1 agonists, beta-cell imidazoline receptor antagonists, and short-acting insulin secretagogues, like antidiabetic phenylacetic acid derivatives, antidiabetic D-phenylalanine derivatives, and mitiglinide and pharmaceutical acceptable salts thereof.

Examples of sulphonyl urea derivatives include, but are not limited to, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide; glimepiride and gliclazide. Tolbutamide, glibenclamide, gliclazide, glibornuride, gliquidone, glisoxepid and glimepiride can be administered in the form that they are marketed under the trademarks RASTINON HOECHST™, AZUGLUCON™, DIAMICRONT™, GLUBORID™, GLURENORM™, PRO-DIABAN™ and AMARYL™, respectively.

Examples of GLP-1 agonists include, but are not limited to those disclosed in U.S. Pat. Nos. 5,120,712, 5,118,666 and 5,512,549, and PCT Publication No. WO 91/11457. In particular, GLP-1 agonists include those compounds like GLP-1 (7-37) in which compound the carboxy-terminal amide functionality of Arg$^{36}$ is displaced with Gly at the 37$^{th}$ position of the GLP-1 (7-36)NH$_2$ molecule and variants and analogs thereof including GLN$^9$-GLP-1 (7-37), D-GLN$^9$-GLP-1 (7-37), acetyl LYS$^9$-GLP-1 (7-37), LYS$^{18}$-GLP-1 (7-37) and, in particular, GLP-1 (7-37)OH, VAL$^8$-GLP-1 (7-37), GLY$^8$-GLP-1(7-37), THR$^8$-GLP-1 (7-37), GLP-1 (7-37) and 4-imidazopropionyl-GLP-1.

One particular example of a GLP-1 agonist is Exendatide, a 39-amino acid peptide amide, which is marketed under the trademark BYETTA™. Extendatide has the empirical formula $C_{184}H_{282}N_{50}O_{60}S$ and molecular weight of 4186.6 Daltons. The amino acid sequence for Extendatide is as follows:
H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$.

Examples of glucagon-like peptide-2 (GLP-2) or GLP-2 agonists include, but are not limited to those disclosed in U.S. Pat. No. 7,056,886 and PCT Publication Nos. WO 00/53208, WO 01/49314 and WO 03/099854. One particular example of a GLP-2 agonist is TEDUGLUTIDE™, a 39-amino acid peptide amide (NPS Pharmaceuticals, Inc.).

Examples of beta-cell imidazoline receptor antagonists include, but are not limited to those described in PCT Publication No. WO 00/78726 and *J. Pharmacol. Exp. Ther.* 1996, 278, 82-89.

An example of an antidiabetic phenylacetic acid derivative is repaglinide and pharmaceutically acceptable salts thereof.

Examples of antidiabetic D-phenylalanine derivatives include, but are not limited to nateglinide (N-[(trans4-isopropylcyclohexyl)-carbonyl]-D-phenylalanine, EP 196222 and EP 526171) and repaglinide ((S)-2-ethoxy-4-{2-[[3-methyl-1-1-[2-(1-piperidinyl)phenyl]butyl]-amino]-2-oxoethyl}benzoic acid, EP 0 147 850 A2 and EP 0 207 331 A1). Nateglinide is intended to include the particular crystal forms (polymorphs) disclosed in U.S. Pat. No. 5,488,510 and European Patent Publication No. EP 0526171 B1. Repaglinide and nateglinide may be administered in the form as they are marketed under the trademarks NOVONORIVI™ and STARLIX™, respectively.

Examples of alpha-Glucosidase inhibitors include, but are not limited to, acarbose, N-(1,3-dihydroxy-2-propyl)valiolamine (voglibose) and the 1-deoxynojirimycin derivative miglitol. Acarbose is 4",6"-dideoxy-4'-[(1S)-(1,4,6/5)-4,5,6-trihydroxy-3-hydroxymethyl-2-cyclo-hexenylamino)maltotriose. The structure of acarbose can as well be described as O-4,6-dideoxy-4-{[1S,4R,5S,6S]-4,5,6-trihydroxy-3-(hydroxymethyl)-2-cyclohexen-1-yl]-amino)-alpha-D-glucopyranosyl-(1-4)-O— alpha-D-glucopyranosyl-(1-4)-D-glucopyranose. (U.S. Pat. No. 4,062,950 and European Patent Publication No. EP 0 226 121). Acarbose and miglitol may be administered in the forms that they are marketed under the trademarks GLUCOBAY™ and DIASTABOL 50™ respectively.

Examples of inhibitors of gastric emptying other than GLP-1 include, but are not limited to those disclosed in *J. Clin. Endocrinol. Metab.* 2000, 85(3), 1043-1048, and *Diabetes Care* 1998, 21, 897-893, especially Amylin and analogs thereof such as pramlintide. Amylin is described in *Diabetologia*, 1996, 39, 492-499.

Examples of $\alpha_2$-adrenergic antagonists include, but are not limited to midaglizole which is described in *Diabetes* 1987, 36, 216-220. The insulin that may be used in combination with ASK1 inhibitors of the invention include, but are not limited to animal insulin preparations extracted from the pancreas of bovine and pig; human insulin preparations genetically synthesized using *Escherichia coli* or yeast; zinc insulin; protamine zinc insulin; fragment or derivative of insulin (e.g., INS-1) and an oral insulin preparation.

In one particular embodiment, the antidiabetic compound administered in combination with ASK1 inhibitors of the invention is selected from the group consisting of nateglinide, mitiglinide, repaglinide, metformin, extendatide, rosiglitazone, tesaglitazar, pioglitazone, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide, including any pharmaceutically acceptable salts thereof.

Examples of the preparation and formulation of PTPase inhibitors, GSK-3 inhibitors, non-small molecule mimetic compounds, GFAT inhibitors, G6Pase inhibitors, glucagon receptor antagonists, PEPCK inhibitors, F-1,6-BPase inhibitors, GP inhibitors, RXR modulators, Beta-3 AR agonists, PDHK inhibitors, inhibitors of gastric emptying and UCP modulators are disclosed in the patents, applications and references provided herein.

In the case of combination therapy with Compound I, the other antidiabetic compound may be administered (e.g., route and dosage form) in a manner known per se for such compound. ASK1 inhibitors of the invention and the other antidiabetic compound may be administered sequentially (i.e., at separate times) or at the same time, either one after the other separately in two separate dose forms or in one combined, single dose form. In one particular embodiment, the other antidiabetic compound is administered with ASK1 inhibitors of the invention as a single, combined dosage form. The dose of the antidiabetic compound may be selected from the range known to be clinically employed for such compound. Any therapeutic compounds of diabetic complications, antihyperlipemic compounds, antiobestic compounds or antihypertensive compounds can be used in combination with ASK1 inhibitors of the invention in the same manner as the above antidiabetic compounds. Examples of therapeutic compounds of diabetic complications include, but are not limited to, aldose reductase inhibitors such as tolrestat, epalrestat, zenarestat, zopolrestat, minalrestat, fidarestat, CT-112 and ranirestat; neurotrophic factors and increasing compounds thereof such as NGF, NT-3, BDNF and neurotrophin production-secretion promoters described in WO01/14372 (e.g., 4-(4-chlorophenyl)-2-(2-methyl-1-imidazolyl)-5-[3-(2-methylphenoxy)propyl]oxazole); neuranagenesis stimulators such as Y-128; PKC inhibitors such as ruboxistaurin mesylate; AGE inhibitors such as ALT946, pimagedine, N-phenacylthiazolium bromide (ALT766), ALT-711, EXO-226, pyridorin and pyridoxamine; reactive oxygen scavengers such as thioctic acid; cerebral vasodilators such as tiapride and mexiletine; somatostatin receptor agonists such as BIM23190; and apoptosis signal regulating kinase-1 (ASK-1) inhibitors. Examples of antihyperlipemic compounds include, but are not limited to, HMG-CoA reductase inhibitors such as pravastatin, simvastatin, lovastatin, atorvastatin, fluvastatin, rosuvastatin and pitavastatin; squalene synthase inhibitors such as compounds described in WO97/10224 (e.g., N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid); fibrate compounds such as bezafibrate, clofibrate, simfibrate and clinofibrate; ACAT inhibitors such as avasimibe and eflucimibe; anion exchange resins such as colestyramine; probucol; nicotinic acid drugs such as nicomol and niceritrol; ethyl icosapentate; and plant sterols such as soysterol and γ-oryzanol. Examples of antiobestic compounds include, but are not limited to, dexfenfluramine, fenfluramine, phentermine, sibutramine, amfepramone, dexamphetamine, mazindol, phenylpropanolamine, clobenzorex; MCH receptor antagonists such as SB-568849 and SNAP-7941; neuropeptide Y antagonists such as CP-422935; cannabinoid receptor antagonists such as SR-141716 and SR-147778; ghrelin antagonist; 11β-hydroxysteroid dehydrogenase inhibitors such as BVT-3498; pancreatic lipase inhibitors such as orlistat and ATL-962; Beta-3 AR agonists such as AJ-9677; peptidic anorexiants such as leptin and CNTF (Ciliary Neurotropic Factor); cholecystokinin agonists such as lintitript and FPL-15849; and feeding deterrent such as P-57. Examples of the antihypertensive compounds include angiotensin converting enzyme inhibitors such as captopril, enalapril and delapril; angiotensin II antagonists such as candesartan cilexetil, losartan, eprosartan, valsartan, telmisartan, irbesartan, olmesartan medoxomil, tasosartan and 1-[[2'-(2,5-dihydro-5-oxo-4H-1,2,4-oxadiazol-3-yl)biphenyl-4-yl]methyl]-2-ethoxy-1H-benzimidazole-7-carboxylic acid; calcium channel blockers such as manidipine, nifedipine, nicardipine, amlodipine and efonidipine; potassium channel openers such as levcromakalim, L-27152, AL0671 and NIP-121; and clonidine.

The structure of the active agents identified herein by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

Compositions Comprising ASK1 Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The ASK1 inhibitors and compositions comprising them may be administered or coadministered in any conventional dosage form. Co-administration in the context of this invention is intended to mean the administration of more than one therapeutic agent, one of which includes a ASK1 inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington: The Science and Practices of Pharmacy, Lippincott Williams, and Wilkins Publisher, $21^{st}$ edition, 2005. The composition or formulation to be administered will, in any event, contain a sufficient quantity of an inhibitor of the present invention to reduce ASK1 activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more ASK1 inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the ASK1 inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The ASK1 inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a ASK1 inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

D. Formulation for Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The ASK1 inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the ASK1 inhibitor alone or in combination with other pharmaceutically acceptable excipients can also be administered.

E. Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

Oral Formulation

| | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of the Present Invention | 1% |
| Microcrystalline Cellulose | 73% |
| Stearic Acid | 25% |
| Colloidal Silica | 1%. |

Dosage, Host and Safety

The compounds of the present invention are stable and can be used safely. In particular, the compounds of the present invention are useful as ASK1 inhibitors for a variety of subjects (e.g., humans, non-human mammals and non-mammals).

The optimal dose may vary depending upon such conditions as, for example, the type of subject, the body weight of the subject, on the severity of the condition, the route of administration, and specific properties of the particular compound being used. Generally, acceptable and effective daily doses are amounts sufficient to effectively slow or eliminate the condition being treated. Typically, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Kits and Articles of Manufacture Comprising ASK1 Inhibitors

The invention is also directed to kits and other articles of manufacture for treating diseases associated with ASK1. It is noted that diseases are intended to cover all conditions for which the ASK1 possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Preparation of ASK1 Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see P. G. M. Wuts and T. W. Greene in "*Greene's Protective Groups in Organic Synthesis*" 4$^{th}$ edition, John Wiley and Sons, 2007.

Scheme A: General Synthetic Route I

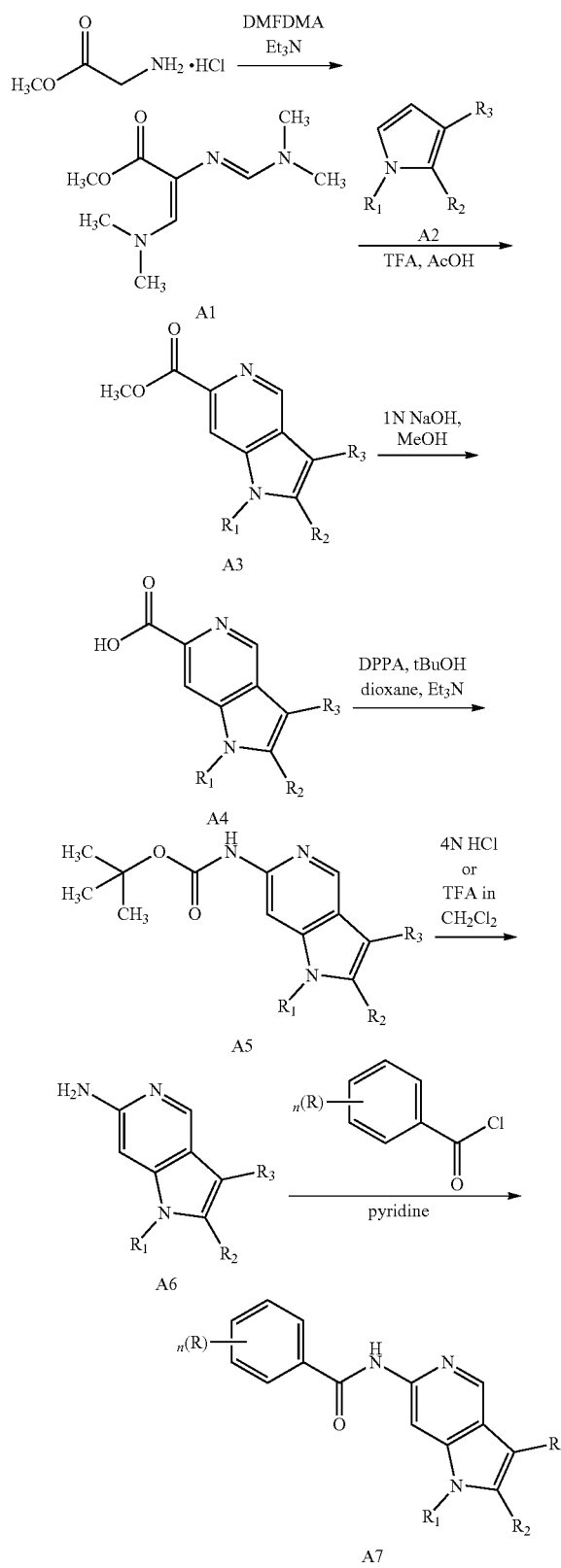

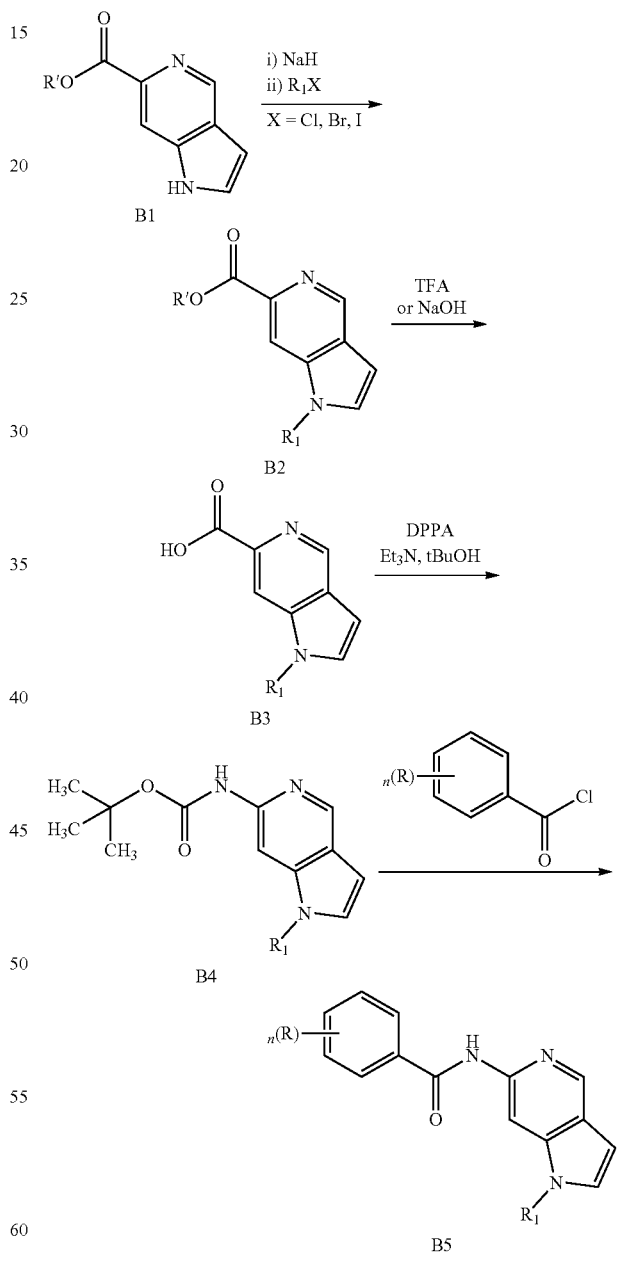

A general synthetic route for producing compounds of the present invention is shown in Scheme A. Reaction of commercially available glycine methyl ester HCl salt with DMFDMA in the presence of triethylamine affords aminoacrylate A1. Cycloaddition of A1 with properly substituted pyrrole A2 gives methylpyrrolo[3,2-c]pyridine-6-carboxylate A3. After the ester was hydrolyzed to give acid A4, the intermediate was subjected to Curtius rearrangement conditions to give Boc-protected amine A5. Alternatively, other alcohols (e.g., benzyl alcohol) could be used to provide different protecting groups (e.g., CBZ). Boc group of A5 can then be removed by either aqueous HCl, or TFA in $CH_2Cl_2$ to give the corresponding salt of amine A6. This intermediate can be acylated by benzoyl chloride, substituted or unsubstituted, in pyridine to give amide A7.

Another general synthetic route for producing compounds of the present invention is shown in Scheme B. 6-Carboxypyrrolo[3,2-c]pyridine B1 can be N-alkylated with an alkylhalide to give B2. After hydrolysis of ester B2 to form acid B3, the intermediate was subject to conditions of the Curtius rearrangement to give the Boc-protected B4. Alternatively, other alcohols (e.g., benzyl alcohol) could be used to provide different protecting groups (e.g., CBZ). Deprotection of the Boc group followed by acylation by substituted benzoyl chloride gives the desired amide B5.

Alternatively compounds of the present invention can be prepared as shown in Scheme C. Ester C1 is reacted with excess alkyl or alkenyl Grignard to give tertiary alcohol C2.

Alternatively compounds of the present invention can be prepared as shown in Scheme D. Ester D1 is reacted with either AD-mix beta or AD-mix alpha to give the corresponding diol D2 and D3, respectively.

Scheme D: General Synthetic Route IV

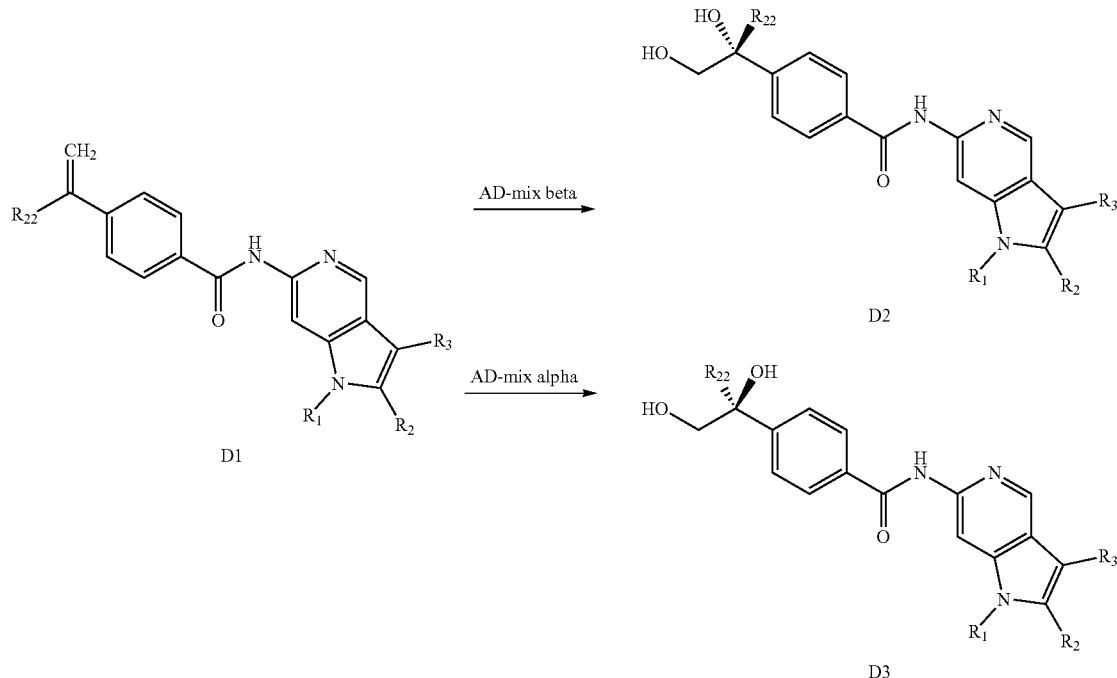

Scheme C: General Synthetic Route III

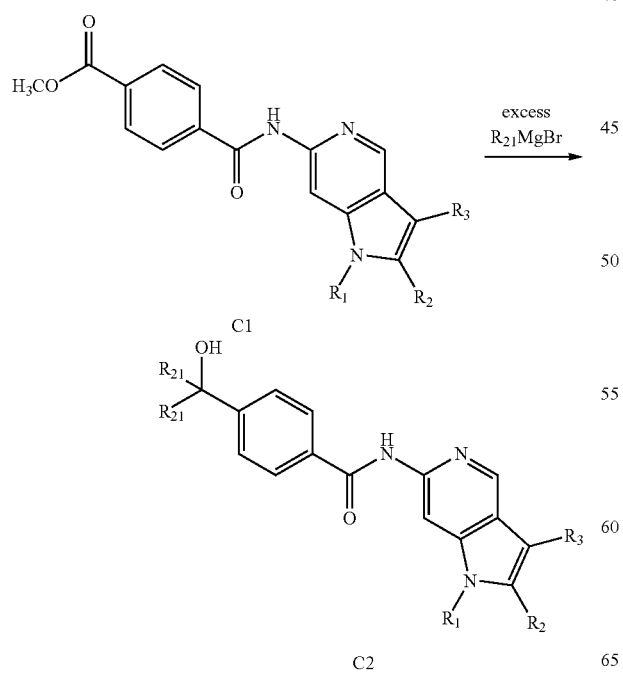

Scheme E: General Synthetic Route V

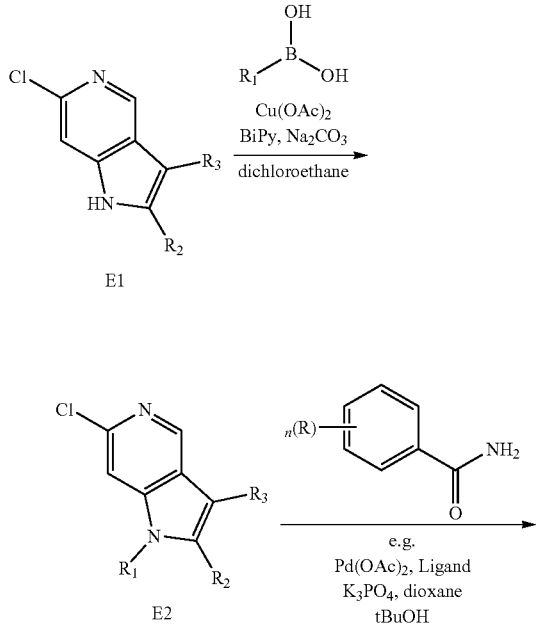

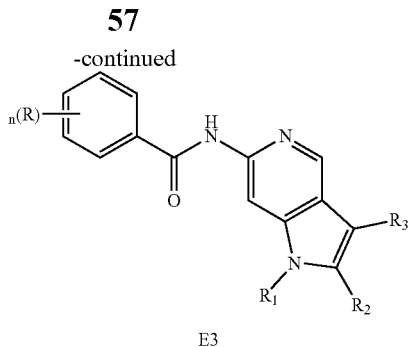

E3

Alternatively compounds of the present invention can be prepared as shown in Scheme E. 6-chloropyrrolo[3,2-c]pyridine E1 is N-alkylated by copper mediated coupling with a boronic acid or ester to give E2 (where $R_1$ is alkyl, cycloalkyl, alkenyl or alkynyl). The desired amide E3 is obtained by palladium-catalyzed coupling with substituted benzamide.

General Procedures

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in P. G. M. Wuts and T. W. Greene, "*Greene's Protecting Groups in Organic Synthesis*", 4$^{th}$ edition, John Wiley & Sons, Inc. 2007.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| μL (microliters) | Ac (acetyl) |
| atm (atmosphere) | ATP (Adenosine Triphosphatase) |
| BOC (tert-butyloxycarbonyl) | BOP (bis(2-oxo-3-oxazolidinyl)phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| Et$_2$O (diethyl ether) | EtOAc (ethyl acetate) |
| FMOC (9-fluorenylmethoxycarbonyl) | g (grams) |

| | |
|---|---|
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | r.t. (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | Brij35 (polyoxyethyleneglycol dodecyl ether) |

All references to ether or $Et_2O$ are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60E-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-23, John Wiley and Sons, New York, N.Y., 2006; Rodd's Chemistry of Carbon Compounds, vols. 1-5 and supps., Elsevier Science Publishers, 1998; Organic Reactions, vols. 1-68, John Wiley and Sons, New York, N.Y., 2007; March J.: Advanced Organic Chemistry, 5th ed., 2001, John Wiley and Sons, New York, N.Y.; and Larock: Comprehensive Organic Transformations, $2^{nd}$ edition, John Wiley and Sons, New York, 1999. The entire disclosures of all documents cited throughout this application are incorporated herein by reference.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques, Andre Collet, and Samuel H. Wilen, Enantiomers, Racemates and Resolutions, John Wiley & Sons, Inc. (1981).

Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, and Samuel H. Wilen, Enantiomers, Racemates and Resolutions, John Wiley & Sons, Inc. (1981).

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

Descriptions of the syntheses of particular compounds according to the present invention based on the above reaction schemes and variations thereof are set forth in the Example section.

Assaying the Biological Activity of the Compounds of the Invention

The inhibitory effect of the compound of the invention on ASK1 may be evaluated by a variety of binding assays and functional assays.

ASK1 protein for the assay may be prepared by standard PCR cloning and expression in a vector. Example A discloses such a method of preparing the enzyme. However, it should be noted that ASK1 is commercially available through Millipore (Cat. #14-606).

The inhibitory effect of the compound of the invention on ASK1 may be evaluated by evaluating the phosphorylating activity of the enzyme on a known substrate with or without the presence of the test compound. Example B provides such an assay where myelin basic protein (Wako) is used as substrate and detection is by scintillation counting. It should be understood other substrates and detection mechanism may be used. A commercially available kit, Cisbio's HTRF® Kin-EASE™ STK kit, has shown to be useful for evaluating ASK1 activity. The assay uses an anti-phosphoseric specific, $Eu^{3+}$-Cryptate labeled antibody to mark the phosphorylated product of ASK1 on a biotinylated kinase substrate, and detection is by time resolved fluorescence using XL665 labeled streptavidin. The fluorescence intensity is proportional to the amount of product formation. Example C provides the assay protocol.

$IC_{50}$ values of selected compounds of the invention were measured using the assay described in Example B. Some of the exemplified compounds were shown to have $IC_{50}$ of greater than 1 µM, some others less than about 1 µM, and most others of the compounds have an $IC_{50}$ value of less than about 0.1 µM. The $IC_{50}$ values of selected compounds of the present invention are given in Table 1.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

EXAMPLES

Example 1

Preparation of Intermediates 1I, 1M and 1Q

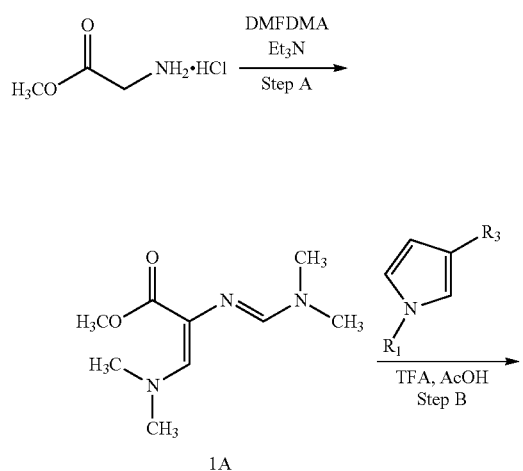

1A

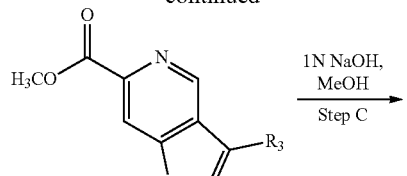

1B: $R_1$ = ——$CH_3$, $R_3$ = ——H
1F: $R_1$ = ——Et, $R_3$ = ——H
1J: $R_1$ = ——$CH_3$, $R_3$ = ——$CH_3$
1N: $R_1$ = ——Et, $R_3$ = ——$CH_3$

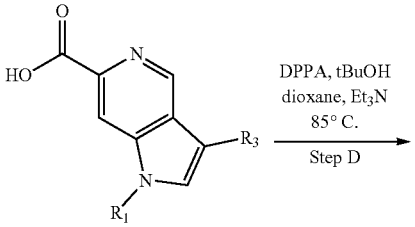

1C: $R_1$ = ——$CH_3$, $R_3$ = ——H
1G: $R_1$ = ——Et, $R_3$ = ——H
1K: $R_1$ = ——$CH_3$, $R_3$ = ——$CH_3$
1O: $R_1$ = ——Et, $R_3$ = ——$CH_3$

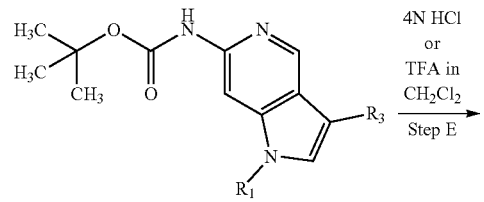

1D: $R_1$ = ——$CH_3$, $R_3$ = ——H
1H: $R_1$ = ——Et, $R_3$ = ——H
1L: $R_1$ = ——$CH_3$, $R_3$ = ——$CH_3$
1P: $R_1$ = ——Et, $R_3$ = ——$CH_3$

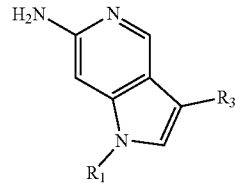

1I: $R_1$ = ——Et, $R_3$ = ——H; TFA salt
1M: $R_1$ = ——$CH_3$, $R_3$ = ——$CH_3$; HCl salt
1Q: $R_1$ = ——Et, $R_3$ = ——$CH_3$; HCl salt Step A:

In a round 200 ml sealed cap glass pressure vessel, methyl 2-aminoacetate hydrochloride (8.2 g, 80 mmol) and dimethylformamide dimethyl acetal (43 ml, 400 mmol) were combined, and then $Et_3N$ (18 ml, 160 mmol) was added. The mixture was heated to 135° C. overnight. After cooling and being transferred into a round bottom flask, volatiles were removed in vacuo from reaction mixture and diluted with dichloromethane (100 ml) and diethylether (50 ml). The precipitated salt, $Et_3N.HCl$, was filtered and washed with 50 ml dichloromethane. The filtrate was evaporated and the resulting crude product methyl 3-(dimethylamino)-2-((dimethylamino)methyleneamino)acrylate (1A) as a gummy dark liquid was used in the next step without further purification.

Step B: 1B:

In a 500 ml round bottom flask, methyl 3-(dimethylamino)-2-((dimethylamino)methyleneamino)acrylate (1A, 24 g, 120 mmol) was dissolved in acetic acid (60 ml) and TFA (20 ml). 1-Methyl-1H-pyrrole (10.56 ml, 119 mmol) was added. The mixture was stirred at room temperature for an hour and at 110° C. for 4 hours until completion of the reaction. Volatiles were then evaporated from the reaction mixture, the residue was cooled in an ice bath. Ice cold saturated $K_2CO_3$ solution (~200 ml) was slowly added to it. The mixture was extracted with EtOAc (3×250 ml). Combined organic layers were then washed with brine, dried over sodium sulfate, filtered and evaporated. The crude product was purified on silica column using hexane-EtOAc (0-100%). Desired product methyl 1-methyl-1H-pyrrolo[3,2-c]pyridine-6-carboxylate (1B, 8.5 g, 38%) was obtained as a thick brown oil.

1F:

In a 500 ml round bottom flask, methyl 3-(dimethylamino)-2-((dimethylamino)methyleneamino)acrylate (1A, 24 g, 120 mmol) was dissolved in acetic acid (60 ml) and TFA (20 ml). 1-Ethyl-1H-pyrrole (11 g, 120 mmol) was added. The mixture was stirred at room temperature for an hour and at 110° C. for 4 hours until completion of the reaction. Volatiles were then evaporated from the reaction mixture, the residue was cooled in an ice bath and ice cold saturated $K_2CO_3$ solution (~200 ml) was slowly added to it. The mixture was extracted with EtOAc (3×250 ml). Combined organic layers were then washed with brine, dried over sodium sulfate, filtered and evaporated. The crude product was purified on a silica column using hexane-EtOAc (0-100%). Desired product 1-ethyl-1H-pyrrolo[3,2-c]pyridine-6-carboxylate (1F, 8.6 g, 35%) was obtained. $^1$H NMR (400 MHz, CHLOROFORM-d) δ ppm 1.51 (t, J=7.33 Hz, 2H) 2.76 (s, 3H) 4.04 (s, 2H) 4.25 (q, J=7.33 Hz, 1H) 7.33 (s, 1H) 8.22 (s, 1H) 8.92 (s, 1H).

1J:

In a 500 ml round bottom flask, methyl 3-(dimethylamino)-2-((dimethylamino)methyleneamino)acrylate (1A, 12 g, 61 mmol) was dissolved in acetic acid (45 ml) and TFA (15 ml). 1,3-Dimethyl-1H-pyrrole (5.8 g, 61 mmol) was added and the mixture was stirred at room temperature for an hour and then at 110° C. for 4 hours. Volatiles were then evaporated from the reaction mixture, the residue was cooled in an ice bath and ice cold saturated $K_2CO_3$ solution (~200 ml) was slowly added to it. The mixture was extracted with EtOAc (3×250 ml). Combined organic layers were then washed with brine, dried over sodium sulfate, filtered and evaporated. The crude product was purified on a silica column using hexane-EtOAc (0-100%). Desired product methyl 1,3-dimethyl-1H-pyrrolo[3,2-c]pyridine-6-carboxylate (1J, 6.8 g, 55%) was obtained.

1N:

In a 500 ml round bottom flask, methyl 3-(dimethylamino)-2-((dimethylamino)methyleneamino)acrylate (1A, 12 g, 61 mmol) was dissolved in acetic acid (45 ml) and TFA (15 ml). 1-Ethyl-3-methyl-1H-pyrrole (6.7 g, 61 mmol) was added and the mixture was stirred at room temperature for an hour and then at 110° C. for 4 hours. Volatiles were then evaporated from the reaction mixture, the residue was cooled in an ice bath and ice cold saturated $K_2CO_3$ solution (~200 ml) was slowly added to it. The mixture was extracted with EtOAc (3×250 ml). Combined organic layers were then washed with brine, dried over sodium sulfate, filtered and evaporated. The crude product was purified on a silica column using hexane-EtOAc (0-100%). Pure fractions were combined and evaporated to give the product methyl 1-ethyl-3-methyl-1H-pyrrolo[3,2-c]pyridine-6-carboxylate (1N, 6.1 g, 46% yield). $^1$H NMR (400 MHz, DMSO-d6) d ppm 1.34 (t, J=7.20 Hz, 3H) 2.34 (d, J=1.01 Hz, 3H) 3.88 (s, 3H) 4.26 (q, J=7.24 Hz, 2H) 7.48 (d, J=1.01 Hz, 1H) 8.20 (d, J=1.01 Hz, 1H) 8.85 (d, J=1.01 Hz, 1H).

Step C: 1C:

In a 500 mL pear flask was added methyl 1-methyl-1H-pyrrolo[3,2-c]pyridine-6-carboxylate (1B, 14 g, 71 mmol) in methanol (71.0 ml). At 0° C. was added 1N sodium hydroxide solution (140 ml, 140 mmol). This was then stirred at 0° C. for 1 h, when the reaction was complete. Brine (25 ml) was added and methanol was removed in vacuo. The aqueous mixture was washed twice with EtOAc. The aqueous layer was then acidified to pH 4; the resulting precipitate was collected on a fritted glass funnel and dried overnight under a stream of nitrogen to give the desired product 1-methyl-1H-pyrrolo[3,2-c]pyridine-6-carboxylic acid (1C, 10 g, 83% yield) as an off white powder. This was used in next step without further purification.

1G: In a 1 L pear flask were added methyl 1-ethyl-1H-pyrrolo[3,2-c]pyridine-6-carboxylate (1F, 16 g, 79 mmol) in methanol (99 ml). At 0° C. was added 1N sodium hydroxide solution (200 ml, 200 mmol). This was then stirred at 0° C. for 1 h. Water was added, and methanol was removed in vacuo. The aqueous residue was washed twice with EtOAc and then acidified to pH 4. The mixture was extracted twice with EtOAc and the aqueous layer was then reduced to about 200 ml in vacuo before being freeze-dried for 4 days. The resulting powder containing the 1-ethyl-1H-pyrrolo[3,2-c]pyridine-6-carboxylic acid (1G) was used in the next step without further purification.

1K:

In a 200 ml round bottom flask, methyl 1,3-dimethyl-1H-pyrrolo[3,2-c]pyridine-6-carboxylate (1J, 1.9 g, 9.30 mmol) was dissolved in THF (20 mL) and to the mixture was added a 2M NaOH (9.30 mL, 18.61 mmol) solution. The reaction was stirred at room temperature for 3 hrs. After completion, volatiles were removed and the residue was cooled in an ice bath and neutralized with dilute HCl to pH=4.0-4.5. Precipitated product 1,3-dimethyl-1H-pyrrolo[3,2-c]pyridine-6-carboxylic acid (1K, 1.7 g, 97%) was collected by filtration, dried, and used in next step without further purification. $^1$H NMR (400 MHz, DMSO-d6) δ ppm 2.40 (s, 3H) 3.95 (s, 3H) 7.69 (d, J=1.01 Hz, 1H) 8.42 (s, 1H) 9.02 (s, 1H).

1O:

In a 200-ml round bottom flask, methyl 1-ethyl-3-methyl-1H-pyrrolo[3,2-c]pyridine-6-carboxylate (1N, 6.0 g, 28 mmol) was dissolved in THF (50 ml). To the mixture was added a 2M NaOH (28 ml, 55 mmol) solution. The reaction was stirred at room temperature for 3 hrs. After completion, volatiles were removed and the residue was cooled in an ice bath and neutralized with dilute HCl to pH=4.0-4.5. The aqueous mixture washed with ethyl acetate (2×100 ml) and then lyophilized to give the crude product 1-ethyl-3-methyl-1H-pyrrolo[3,2-c]pyridine-6-carboxylic acid (1O) which is used in the next step without further purification.

Step D: 1D:

In a 500 ml round bottom flask, 1-methyl-1H-pyrrolo[3,2-c]pyridine-6-carboxylic acid (1B, 10 g, 57 mmol), diphenylphosphoryl azide (16 ml, 74 mmol), and TEA (10 ml, 74 mmol) were dissolved in THF (60 ml) and added t-BuOH (60 ml) and heated on oil bath at 85° C. for 3 hours. Volatiles were removed in vacuo from the reaction mixture and the residue was further washed with water (150 ml) and extracted into ethyl acetate (3×150 ml). Combined organic layer were washed with brine (100 ml) dried over sodium sulfate and concentrated using rotavapor. The residue was purified using column chromatography with hexane-ethyl acetate (0-100%) mixtures. Pure product fractions were collected and concentrated to obtain the product (1D, 10.5 g, 74.8%) as a light yellow solid. $^1$H NMR (400 MHz, DMSO-$d_6$) δ ppm 1.49 (s, 9H) 3.73 (s, 3H) 6.48 (dd, J=3.16, 0.88 Hz, 1H) 7.29 (d, J=3.28 Hz, 2H) 7.78 (s, 1H) 8.49 (d, J=1.01 Hz, 1H) 9.44 (s, 1H)

1H:

In a 500 mL pear flask was added 1-ethyl-1H-pyrrolo[3,2-c]pyridine-6-carboxylic acid (1G, assumed 30.4 mmol) in dioxane (90 ml) and t-butanol (90 ml) to give a brown suspension. To this was then added triethylamine (5.5 ml, 40 mmol) and the mixture was then heated to 85° C. After 7 hours, the reaction did not change much from the 25% conversion achieved in the first two hours. An additional 4.3 ml of diphenylphosphoryl azide (0.65 eq.) was added the next morning and after 5 hours, the reaction has progressed significantly. Brine was added and the mixture was extracted twice with ethyl acetate. Combined organic layers were dried over MgSO$_4$, filtered and concentrated. Crude product was purified by column chromatography (SiO2, eluting with a gradient of 20-30% EtOAc/hexanes) to give tert-butyl 1-ethyl-1H-pyrrolo[3,2-c]pyridin-6-ylcarbamate (1H, 3.6 g, 45%).

1L:

In a 100 ml sealed cap glass pressure vessel, 1,3-dimethyl-1H-pyrrolo[3,2-c]pyridine-6-carboxylic acid (1K, 1.7 g, 9.0 mmol), diphenylphosphoryl azide (2.1 ml, 9.8 mmol), and TEA (2.5 ml, 18 mmol) were dissolved in THF (10 ml). To this mixture was added t-BuOH (10 ml) and with the cap sealed, the mixture was heated in an oil bath at 85° C. for 4 hrs. After cooling the mixture was transferred into a round bottom flask using THF, concentrated in vacuo and purified using column chromatography (hexanes-ethyl acetate (0-100%)). Pure product fractions were collected and solvents were evaporated to obtain the product tert-butyl 1,3-dimethyl-1H-pyrrolo[3,2-c]pyridin-6-ylcarbamate (1L, 1.3 g, 56%) as a fluffy white solid. $^1$H NMR (400 MHz, DMSO-d6) δ ppm 1.49 (s, 9H) 2.25 (d, J=1.01 Hz, 3H) 3.66 (s, 3H) 7.02 (d, J=1.01 Hz, 1H) 7.59-7.78 (m, 1H) 8.43 (d, J=1.01 Hz, 1H) 9.40 (s, 1H).

1P:

In a 50 ml sealed cap glass vessel, 1-ethyl-3-methyl-1H-pyrrolo[3,2-c]pyridine-6-carboxylic acid (1O, 1.75 g, 8.57 mmol), Diphenylphosphoryl azide (2.408 ml, 11.14 mmol), and TEA (2.389 ml, 17.14 mmol) were dissolved in THF (Ratio: 1.000, Volume: 6.00 ml) and added t-BuOH (Ratio: 1.000, Volume: 6 ml) and sealed the cap and heated on oil bath at 85° C. for 2 hrs. Then transferred into round bottom flask using THF, evaporated the reaction mixture and purified using column chromatography (Hexane-Ethyl acetate mixtures). Pure product fractions were collected and concentrated to obtain the product tert-butyl 1-ethyl-3-methyl-1H-pyrrolo[3,2-c]pyridin-6-ylcarbamate (1P, 0.9 g, 38% yield) as a fluffy white solid. $^1$H NMR (400 MHz, DMSO-d6) δ ppm 1.32 (t, J=7.20 Hz, 3H) 1.49 (s, 9H) 2.26 (d, J=1.26 Hz, 3H) 4.06 (q, J=7.24 Hz, 2H) 7.10 (d, J=1.01 Hz, 1H) 7.73 (s, 1H) 8.33-8.51 (m, 1H) 9.49 (br. s., 1H).

Step E: 1I:

In a 200 mL pear flask was added tert-butyl 1-ethyl-1H-pyrrolo[3,2-c]pyridin-6-ylcarbamate (1H, 1 g, 3.83 mmol) in dichloromethane (20 ml). At 0° C., TFA (5 ml) was added, and the mixture was stored in the refrigerator overnight, after which, the reaction was complete according to UPLC analysis. The mixture was then concentrated in vacuo. To the residue was added toluene, and the mixture was concentrated in vacuo once again; this procedure was repeated once more, before the residue was triturated with Et$_2$O to give the TFA salt of the desired product 1-ethyl-1H-pyrrolo[3,2-c]pyridin-6-amine 1I as a purplish red solid, which is then used in the next step without further purification.

1M:

In a 125 ml round bottom flask, tert-butyl 1,3-dimethyl-1H-pyrrolo[3,2-c]pyridin-6-ylcarbamate (1L, 0.7 g, 2.7 mmol) was dissolved in 4N HCl (15 ml) continued at room temperature for 3 h. After completion, the reaction mixture was concentrated to dryness and the residue containing the HCl salt of the desired product 1,3-dimethyl-1H-pyrrolo[3, 2-c]pyridin-6-amine 1M, which was used in the next step without further purification.

1Q:

In a 125 ml round bottom flask, tert-butyl 1-ethyl-3-methyl-1H-pyrrolo[3,2-c]pyridin-6-ylcarbamate (1P, 0.65 g, 2.4 mmol) was dissolved in 4N HCl (15 ml) continued at room temperature for 3 h. After completion, the reaction mixture was concentrated to dryness and the residue containing the HCl salt of the desired product 1-ethyl-3-methyl-1H-pyrrolo [3,2-c]pyridin-6-amine 1Q, which was used in the next step without further purification.

Example 2

Preparation of Intermediates 2C and 2D

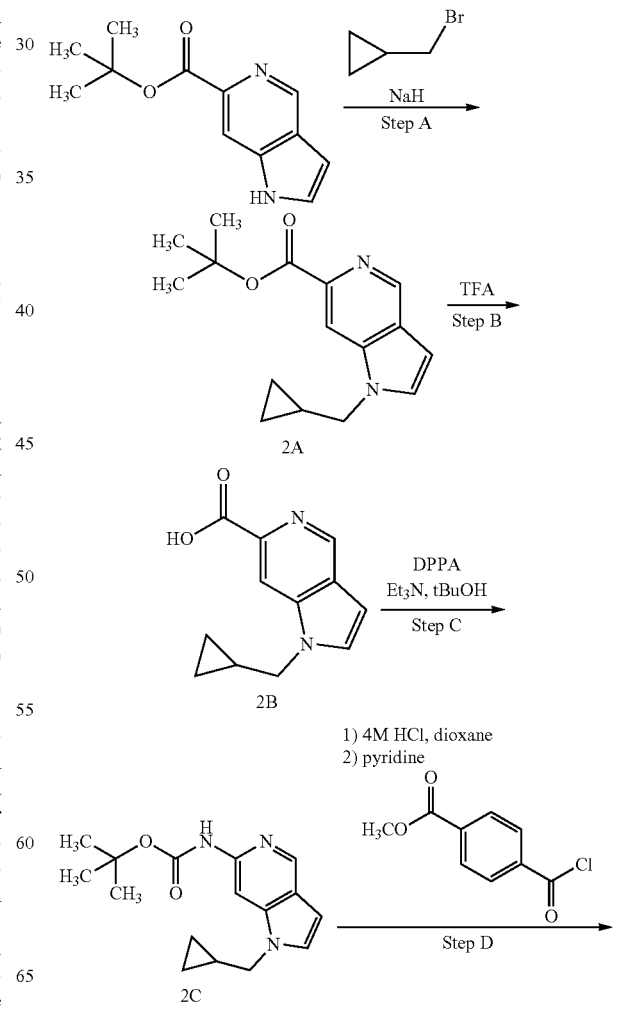

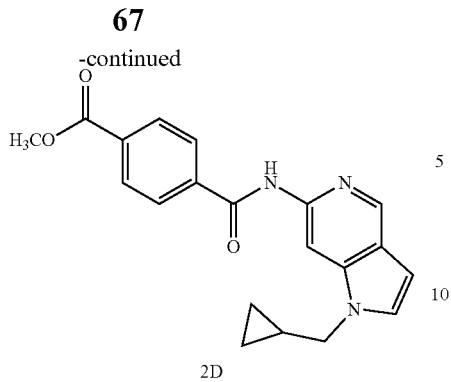

2D

Step A: 2A

To a mixture of tert-butyl 1H-pyrrolo[3,2-c]pyridine-6-carboxylate (1.0 g, 4.6 mmol) in DMF (20 ml) was added sodium hydride (60% in oil) (0.4 g, 10 mmol) and stirred at room temperature for 3 h. To the mixture, (bromomethyl)cyclopropane (1.2 g, 9.2 mmol) was added and stirred at room temperature. for 2 h. The reaction mixture was extracted with EtOAc/H$_2$O. The organic layer was washed with brine, dried over MgSO$_4$ and concentrated in vacuo. The crude mixture was purified by chromatography (SiO$_2$, hexanes:EtOAc=50:50) to give tert-butyl 1-(cyclopropylmethyl)-1H-pyrrolo[3,2-c]pyridine-6-carboxylate (2A, 1.1 g, 4.0 mmol, 88% yield) as a yellow oil. $^1$H NMR (400 MHz, CHLOROFORM-d) δ ppm 0.16-0.23 (m, 2H) 0.44-0.51 (m, 2H) 0.99-1.11 (m, 1H) 1.48 (s, 9H) 3.84 (d, J=7.07 Hz, 2H) 6.45-6.47 (m, 1H) 7.19 (d, J=3.03 Hz, 1H) 7.96 (s, 1H) 8.79 (s, 1H).

Step B: 2B

A mixture of tert-butyl 1-(cyclopropylmethyl)-1H-pyrrolo[3,2-c]pyridine-6-carboxylate (2A, 1.1 g, 4.0 mmol) in DCM (5 ml) and TFA (5 ml) was stirred at 50° C. for 15 h. The mixture was concentrated in vacuo to give 1-(cyclopropylmethyl)-1H-pyrrolo[3,2-c]pyridine-6-carboxylic acid (2B, 0.9 g, 4.0 mmol) as a brown oil. The material was used for next reaction without further purifications. ESI-MS: m/z 217.1 (M+H)$^+$.

Step C: 2C

A mixture of diphenylphosphoryl azide (1.7 g, 6.2 mmol), Et$_3$N (2.9 ml, 21 mmol) and 1-(cyclopropylmethyl)-1H-pyrrolo[3,2-c]pyridine-6-carboxylic acid (2B, 0.9 g, 4.0 mmol) in 2-methylpropan-2-ol (10 g, 140 mmol) was stirred at room temperature for 1 h and 80° C. for 3 h. The mixture was extracted with EtOAct/H2O. The organic layer was washed with brine, dried over MgSO$_4$ and concentrated in vacuo. The crude mixture was purified by chromatography (SiO$_2$, hexanes:EtOAc=50:50) to give tert-butyl 1-(cyclopropylmethyl)-1H-pyrrolo[3,2-c]pyridin-6-ylcarbamate (2C, 300 mg, 25% yield) as a white powder. $^1$H NMR (400 MHz, CHLOROFORM-d) δ ppm 0.35-0.44 (m, 2H) 0.57-0.70 (m, 2H) 1.19-1.33 (m, 1H) 1.57 (s, 9H) 3.97 (d, J=6.82 Hz, 2H) 6.52-6.54 (m, 1H) 7.19 (d, J=3.28 Hz, 1H) 7.59 (br. s., 1H) 7.93 (s, 1H) 8.56 (d, J=1.01 Hz, 1H).

Step D: 2D

A mixture of tert-butyl 1-(cyclopropylmethyl)-1H-pyrrolo[3,2-c]pyridin-6-ylcarbamate (2C, 260 mg, 0.91 mmol) in 4M HCl in dioxane (3 ml) was stirred at room temperature for 15 h. The mixture was concentrated in vacuo and dissolved in pyridine (3 ml, 37 mmol). To the mixture, methyl 4-(chlorocarbonyl)benzoate (270 mg, 1.4 mmol) was added and stirred at room temperature for 3 hours. The mixture was extracted with EtOAc. The organic layer was washed with brine, dried over MgSO$_4$ and concentrated in vacuo. The crude mixture was purified by chromatography (NH—SiO$_2$, EtOAc) to give methyl 4-(1-(cyclopropylmethyl)-1H-pyrrolo[3,2-c]pyridin-6-ylcarbamoyl)benzoate (2D, 270 mg, 0.77 mmol, 85% yield) as a white powder. $^1$H NMR (400 MHz, DMSO-d$_6$) δ ppm 0.39-0.47 (m, 2H) 0.50-0.59 (m, 2H) 1.17-1.33 (m, 1H) 3.89 (s, 3H) 4.06 (d, J=7.07 Hz, 2H) 6.57-6.59 (m, 1H) 7.52 (d, J=3.28 Hz, 1H) 8.03-8.09 (m, 2H) 8.14-8.19 (m, 2H) 8.34 (s, 1H) 8.65 (s, 1H) 10.86 (s, 1H). ESI-MS: m/z 350.0 (M+H)$^+$.

Example 3

Preparation of Intermediates 3D and 3H

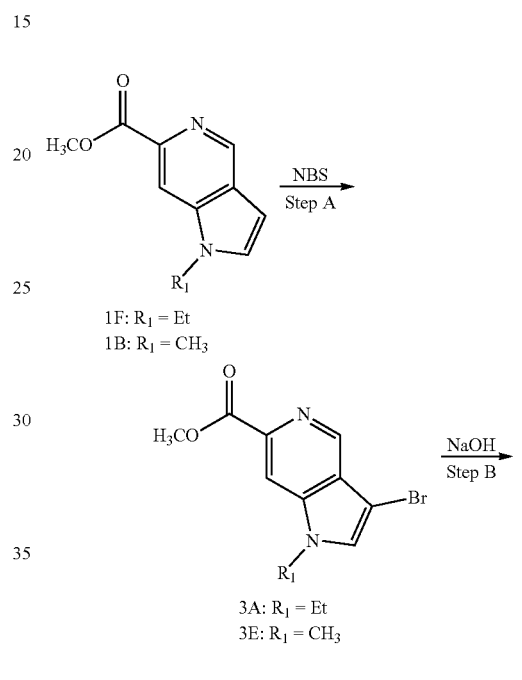

1F: R$_1$ = Et
1B: R$_1$ = CH$_3$

3A: R$_1$ = Et
3E: R$_1$ = CH$_3$

3B: R$_1$ = Et
3F: R$_1$ = CH$_3$

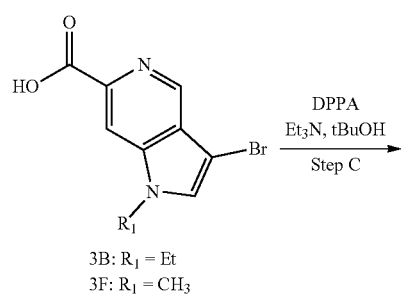

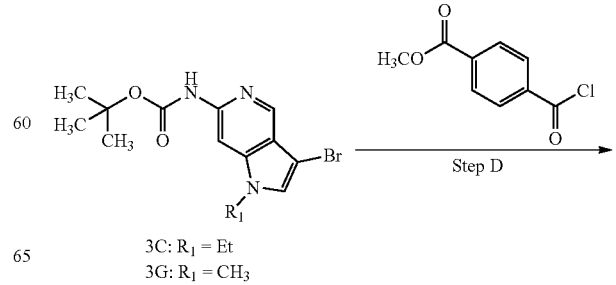

3C: R$_1$ = Et
3G: R$_1$ = CH$_3$

-continued

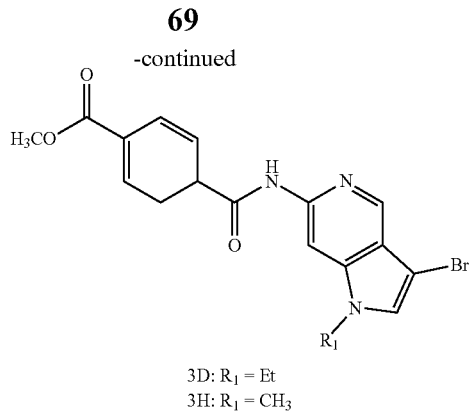

3D: R₁ = Et
3H: R₁ = CH₃

Step A: 3A

To an ice-cooled solution of methyl 1-ethyl-1H-pyrrolo[3,2-c]pyridine-6-carboxylate (1F, 700 mg, 3.43 mmol) in DCM (5 ml) was added NBS (610 mg, 3.43 mmol). The reaction mixture was stirred at room temperature for 10 min. The reaction mixture was concentrated in vacuo and purified by chromatography (SiO₂, EtOAc) to give methyl 3-bromo-1-ethyl-1H-pyrrolo[3,2-c]pyridine-6-carboxylate (3A, 950 mg, 3.36 mmol, 98% yield) as a white powder. ¹H NMR (400 MHz, CHLOROFORM-d) δ ppm 1.52 (t, J=7.33 Hz, 3H) 4.04 (s, 3H) 4.25 (q, J=7.33 Hz, 2H) 7.33 (s, 1H) 8.22 (d, J=0.76 Hz, 1H) 8.92 (d, J=1.01 Hz, 1H).

3E

In a 125 ml round bottom flask, methyl 1-methyl-1H-pyrrolo[3,2-c]pyridine-6-carboxylate (1B, 6.0 g, 31.5 mmol) was dissolved in CH₂Cl₂ (20 ml) and the mixture was cooled to 0° C. in an ice bath. Then N-bromosuccinimide (5.6 g, 32 mmol) was slowly added to this reaction mixture and stirring continued for 30 min to ensure the completion of the reaction. Then the solution was evaporated and the residue was extracted with dichloromethane (2×150 ml). Combined organic layers were dried over sodium sulfate and evaporated to give the product methyl 3-bromo-1-methyl-1H-pyrrolo[3,2-c]pyridine-6-carboxylate (3E, 8.4 g, 99%) as a brown solid.

Step B: 3B

A mixture of methyl 3-bromo-1-ethyl-1H-pyrrolo[3,2-c]pyridine-6-carboxylate (3A, 3.0 g, 11 mmol) in EtOH (10 ml) and 1N NaOH (10 ml) was stirred at 80° C. for 5 days. The reaction mixture was acidified with 1N HCl, concentrated in vacuo and dried to give 3-bromo-1-ethyl-1H-pyrrolo[3,2-c]pyridine-6-carboxylic acid (3B, 2.8 g, 10 mmol, 98% yield) as a pale brown powder. ¹H NMR (400 MHz, DMSO-d6) δ ppm 1.42 (t, J=7.20 Hz, 3H) 4.49 (q, J=7.33 Hz, 2H) 8.35 (s, 1H) 8.65 (s, 1H) 8.91 (s, 1H). 3F In a 200 ml round bottom flask, methyl 3-bromo-1-methyl-1H-pyrrolo[3,2-c]pyridine-6-carboxylate (3E, 8.5 g, 32 mmol) was dissolved THF (50 ml) NaOH (32 ml, 63 mmol) solution was added to the mixture and the stirring continued at room temperature overnight. Another equivalent of base was added and the mixture was warmed with water bath to complete the reaction. Volatiles were removed in vacuo and the residue was cooled in an ice bath and neutralized with dilute HCl to pH 4.0-4.5. The precipitated product was collected by filtration to give the product 3-bromo-1-methyl-1H-pyrrolo[3,2-c]pyridine-6-carboxylic acid (3F, 7.3 g, 91%).

Step C: 3C

A mixture of diphenylphosphoryl azide (4.3 g, 16 mmol), Et₃N (7.3 ml, 52 mmol) and 3-bromo-1-ethyl-1H-pyrrolo[3,2-c]pyridine-6-carboxylic acid (3B, 2.8 g, 10 mmol) in DMF (30 ml) was stirred at 0° C. for 1 h. The mixture was extracted with EtOAc/H₂O. The organic layer was washed with brine, dried over MgSO₄ and concentrated in vacuo. The crude mixture was dissolved in toluene (30 ml) and added 2-methylpropan-2-ol (3.9 g, 52 mmol). The mixture was stirred at 70° C. for 2 h. The mixture was concentrated in vacuo and purified by chromatography (SiO₂, hexanes:EtOAc=1:1) to give tert-butyl 3-bromo-1-ethyl-1H-pyrrolo[3,2-c]pyridin-6-ylcarbamate (3C, 340 mg, 0.99 mmol, 9.5% yield) as a white powder. ¹H NMR (400 MHz, DMSO-d6) δ ppm 1.35 (t, J=7.20 Hz, 3H) 1.49 (s, 9H) 4.14 (q, J=7.33 Hz, 2H) 7.60 (s, 1H) 7.83 (d, J=0.76 Hz, 1H) 8.36 (d, J=0.76 Hz, 1H) 9.59 (s, 1H).

3G

In a 50 ml sealed cap glass vessel, 3-bromo-1-methyl-1H-pyrrolo[3,2-c]pyridine-6-carboxylic acid (3F, 4.0 g, 15.68 mmol), diphenylphosphoryl azide (3.73 ml, 17.25 mmol), and TEA (4.37 ml, 31.4 mmol) were dissolved in THF (15 ml) and t-BuOH (15 ml). The vessel was sealed and heated in oil bath at 85° C. for 2 hrs. Transferred into a round bottom flask with THF, the mixture was concentrated and purified using column chromatography (hexanes/EtOAc mixtures). Pure product fractions were collected and concentrated in vacuo to obtain the product tert-butyl 3-bromo-1-methyl-1H-pyrrolo[3,2-c]pyridin-6-ylcarbamate (3G, 1.3 g, 24%) as a fluffy white solid.

Step D: 3D

A mixture of tert-butyl 3-bromo-1-ethyl-1H-pyrrolo[3,2-c]pyridin-6-ylcarbamate (3C, 340 mg, 0.99 mmol) in 4M HCl in dioxane (3 ml) was stirred at room temperature for 1 h and 70° C. for 2 h. The mixture was concentrated in vacuo and dissolved in pyridine (3 ml). To the mixture, methyl 4-(chlorocarbonyl)benzoate (220 mg, 1.1 mmol) was added and stirred at room temperature for 3 h. The mixture was extracted with EtOAc/H₂O. The organic layer was washed with brine, dried over MgSO4 and concentrated in vacuo. The crude mixture was purified by chromatography (basic-SiO2, hexanes:EtOAc=3:1) to give methyl 4-(3-bromo-1-ethyl-1H-pyrrolo[3,2-c]pyridin-6-ylcarbamoyl)benzoate (3D, 350 mg, 0.87 mmol, 87% yield) as a white powder. ¹H NMR (400 MHz, DMSO-d6) δ ppm 1.40 (t, J=1.00 Hz, 3H) 3.90 (s, 3H) 4.21 (q, J=7.16 Hz, 2H) 7.72 (s, 1H) 7.99-8.11 (m, 2H) 8.11-8.20 (m, 2H) 8.35 (d, J=0.76 Hz, 1H) 8.52 (d, J=1.01 Hz, 1H) 10.96 (s, 1H).

3H

In a 125 ml round bottom flask, tert-butyl 3-bromo-1-methyl-1H-pyrrolo[3,2-c]pyridin-6-ylcarbamate (3G, 0.6 g, 1.839 mmol) was dissolved in 4N HCl (15 ml) and the mixture was stirred at room temperature for 3 h. After completion, volatiles were evaporated and the mixture was re-dissolved in DMA (10 ml). To this was added methyl 4-(chlorocarbonyl)benzoate (0.44 g, 2.2 mmol) and the mixture was stirred at 50° C. for five hours. The reaction was poured into ice water. The precipitated product was collected and dried to obtain the product methyl 4-(3-bromo-1-methyl-1H-pyrrolo[3,2-c]pyridin-6-ylcarbamoyl)benzoate (3H, 0.6 g, 84%). Small amount of debrominated product was observed.

Example 4

Preparation of Intermediates 4A, 4B

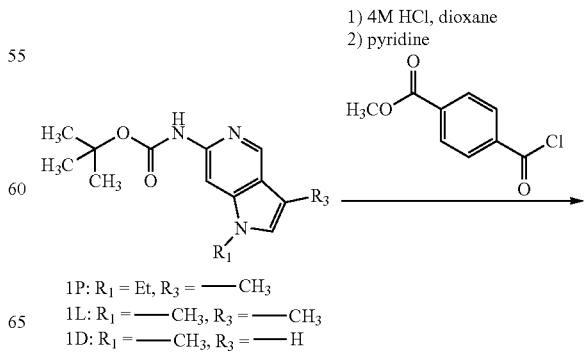

1P: R₁ = Et, R₃ = —CH₃
1L: R₁ = —CH₃, R₃ = —CH₃
1D: R₁ = —CH₃, R₃ = —H

-continued

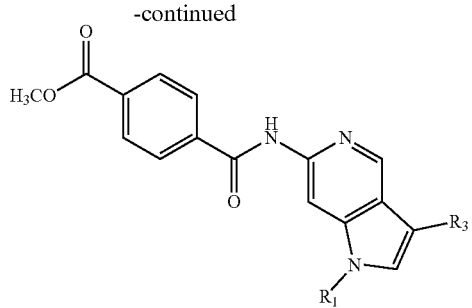

4A: R₁ = —Et, R₃ = —CH₃
4B: R₁ = —CH₃, R₃ = —CH₃
4C: R₁ = —CH₃, R₃ = —H

4A

In a 125 ml round bottom flask, tert-butyl 1-ethyl-3-methyl-1H-pyrrolo[3,2-c]pyridin-6-ylcarbamate (1P, 0.65 g, 2.4 mmol) was dissolved in 4N HCl (15 ml) and stirring continued at room temperature for 3 h. After completion, volatiles were evaporated from the reaction mixture. The residue was re-dissolved in DMA (10 ml) and methyl 4-(chlorocarbonyl) benzoate (0.56 g, 2.8 mmol) was added. The reaction continued at 50° C. for three hours, and then the reaction mixture was poured into ice water. The precipitated product methyl 4-(1-ethyl-3-methyl-1H-pyrrolo[3,2-c]pyridin-6-ylcarbamoyl)benzoate (4A, 630 mg, 78%) was collected, dried and used in the next step without further purification.

4B

In a 125 ml round bottom flask, tert-butyl 1,3-dimethyl-1H-pyrrolo[3,2-c]pyridin-6-ylcarbamate (1L, 0.7 g, 2.7 mmol) was dissolved in 4N HCl (15 ml) and stirring continued at room temperature for 3 h. After completion, volatiles were evaporated from the reaction mixture. The residue was re-dissolved in DMA (10 ml) and methyl 4-(chlorocarbonyl) benzoate (0.638 g, 3.21 mmol) was added. The reaction continued at 50° C. for three hours, and then the reaction mixture was poured into ice water. The precipitated product methyl 4-(1,3-dimethyl-1H-pyrrolo[3,2-c]pyridin-6-ylcarbamoyl) benzoate (4B, 800 mg, 92%) was collected, dried and used in the next step without further purification. ¹H NMR (400 MHz, DMSO-d6) δ ppm 2.35 (d, J=1.26 Hz, 1H) 3.88 (t, J=12.63 Hz, 7H) 8.05 (s, 4H) 8.08-8.20 (m, 2H) 8.29 (d, J=8.59 Hz, 1H)

4C

In a 500 ml round bottom flask, tert-butyl 1-methyl-1H-pyrrolo[3,2-c]pyridin-6-ylcarbamate (1D, 11 g, 43 mmol) was dissolved in 4N HCl (75 ml) and the mixture was stirred at room temperature for 3 h. After completion, volatiles were evaporated from the reaction mixture and the residue was redissolved in DMA (10 ml). To this was added methyl 4-(chlorocarbonyl)benzoate (10 g, 51 mmol) and the mixture was stirred at 50° C. for five hours. The reaction mixture was then poured into ice water, and the precipitate was collected by filtration and dried to obtain the product, which is used without further purification.

Example 5

Preparation of Intermediate 5A

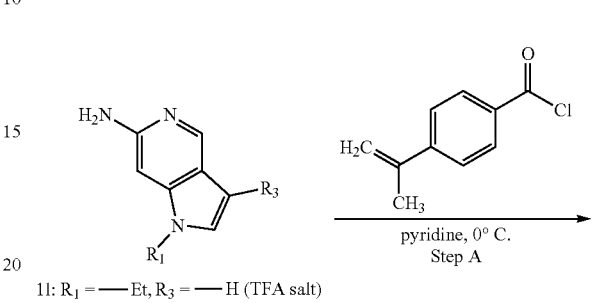

1I: R₁ = —Et, R₃ = —H (TFA salt)

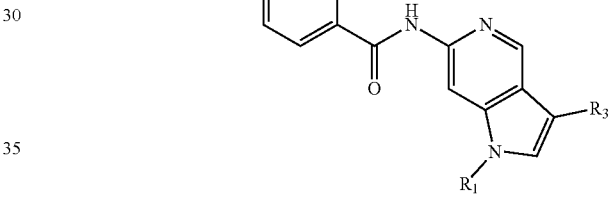

5A: R₁ = —Et, R₃ = —H

5A:

In a 50 mL pear flask were added 1-ethyl-1H-pyrrolo[3,2-c]pyridin-6-amine, TFA (1I, 5.2 g, 19 mmol) in pyridine (200 ml). At 0° C., 4-(prop-1-en-2-yl)benzoyl chloride (3.8 g, 21 mmol) was added. After 15 minutes, sodium hydride (0.53 g, 13 mmol) was added, and the reaction was stirred at room temperature for four hours. At 0° C., an additional 0.55 equivalent of 4-(prop-1-en-2-yl)benzoyl chloride was added and the reaction mixture was let stirred for another 15 hours at room temperature. The reaction was quenched by adding saturated NaHCO₃ at 0° C. and stirred for 30 minutes. Volatiles were removed in vacuo, and the residue was extracted with ethyl acetate twice. Combined organic layers were dried over MgSO₄, filtered and concentrated. The crude mixture was then purified by normal phase column chromatography (SiO₂, eluting 20-50% EtOAc) to give the desired product N-(1-ethyl-1H-pyrrolo[3,2-c]pyridin-6-yl)-4-(prop-1-en-2-yl)benzamide (5A, 4.7 g, 15 mmol, 81% yield). ¹H NMR (DMSO-d₆) δ: 10.61 (s, 4H), 8.64 (s, 4H), 8.32 (s, 4H), 8.04-8.10 (m, 9H), 7.62-7.67 (m, 9H), 7.47 (d, J=3.3 Hz, 4H), 6.57 (dd, J=3.2, 0.9 Hz, 5H), 5.58 (s, 4H), 5.23 (t, J=1.4 Hz, 4H), 4.21 (q, J=7.2 Hz, 9H), 2.16 (d, J=0.5 Hz, 13H), 1.39 (t, J=7.2 Hz, 3H); m.p. 125-8° C.

Example 6

Preparation of Intermediate 6A and 6B

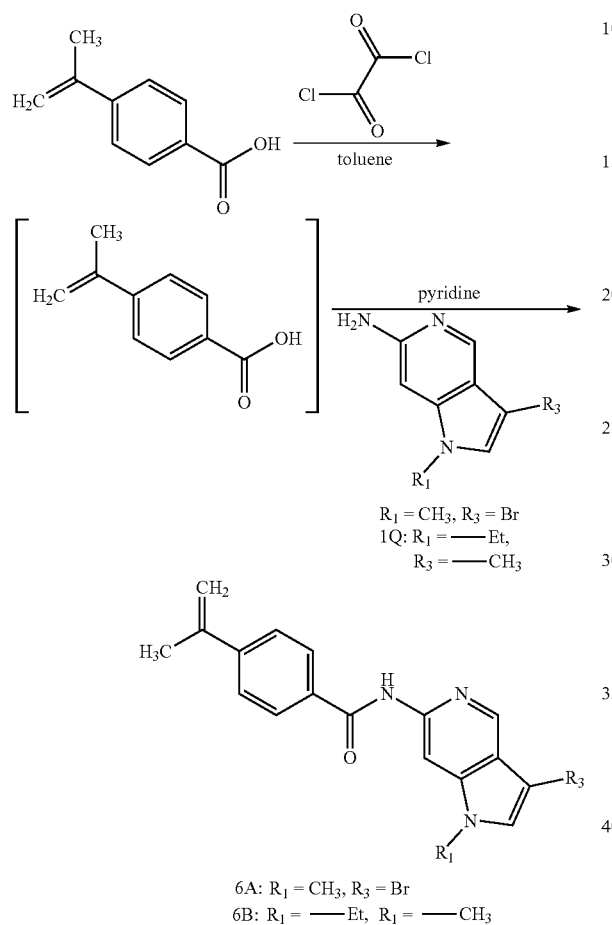

6A

In a 50 ml round bottom flask, 4-(prop-1-en-2-yl)benzoic acid (580 mg, 3.6 mmol) was dissolved in 15 ml toluene, and 2.0 M oxalyl chloride in dichloromethane (3.6 ml, 7.2 mmol) was added slowly. Stirring continued for 3 hours, and then volatiles were evaporated from the reaction mixture. To the residue was added 5 ml toluene and the mixture was concentrated in vacuo to azeotropically remove residual water. The residue was then dissolved in DMA (12 ml) and 3-bromo-1-methyl-1H-pyrrolo[3,2-c]pyridin-6-amine (400 mg, 1.8 mmol) was added. Stirring continued at 50° C. for another 3 hours. The mixture was then poured into ice water. The precipitate was collected and dried to obtain the product N-(3-bromo-1-methyl-1H-pyrrolo[3,2-c]pyridin-6-yl)-4-(prop-1-en-2-yl)benzamide (6A, 440 mg, 67%). This was used in the next step without further purification.

6B

In a 50 ml round bottom flask, 4-(prop-1-en-2-yl)benzoic acid (1.0 g, 6.3 mmol) was dissolved in 15 ml toluene and 2.0 M oxalyl dichloride (6.3 ml, 13 mmol) in dichloromethane was added slowly. Stirring continued for 3 hours, and then volatiles were evaporated from the reaction mixture. To the residue was added 5 ml toluene and the mixture was concentrated in vacuo to azeotropically remove residual water. The residue was then dissolved in DMA (10 ml) and 1-ethyl-3-methyl-1H-pyrrolo[3,2-c]pyridin-6-amine (1Q, 550 mg, 3.14 mmol) was added. Stirring continued at 50° C. overnight. The mixture was then poured into ice water. The precipitate was collected and dried to obtain the product N-(1-ethyl-3-methyl-1H-pyrrolo[3,2-c]pyridin-6-yl)-4-(prop-1-en-2-yl)benzamide (6B, 820 mg, 82%). This was used in the next step without further purification.

Example 7

Preparation of Intermediates 7

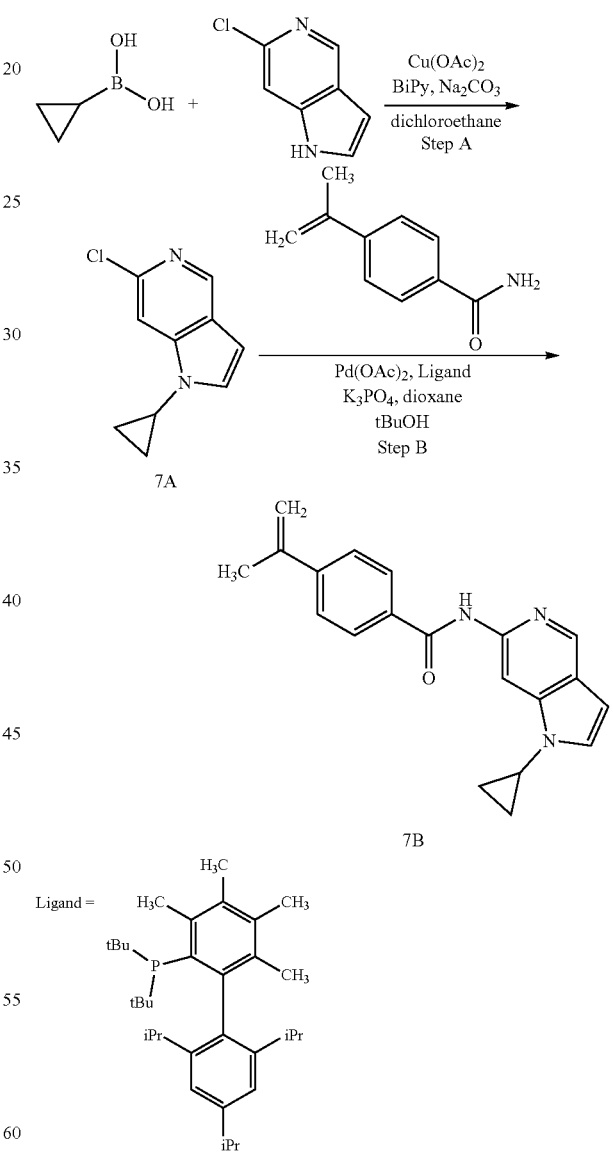

Step A: 7A

In a 2 L round bottom flask were added copper(II) acetate (8.9 g, 49 mmol) and 2,2'-bipyridine (7.8 g, 49 mmol) in 1,2-dichloroethane (240 ml). This was heated to 70° C. Separately were suspended 6-chloro-1H-pyrrolo[3,2-c]pyridine (15 g, 98 mmol) and cyclopropylboronic acid (17 g, 200 mmol) in 1,2-dichloroethane (240 ml). To the first heated mixture was added sodium carbonate (21 g, 200 mmol), followed by the second mixture, and the resulting mixture turned from green to dark red color. The mixture was heated to 70° C. overnight. Next day, conversion was ~50%, and another 0.25 equivalent of Cu(OAc)$_2$ (4.5 g), 0.25 equivalent of BiPy (3.9 g), and 1.0 equivalent of cyclopropylboronic acid (8.5 g) were added. The mixture was continued to stir at 70° C. for 12 hr. After cooling to room temperature, 250 ml brine and 250 ml EtOAc were added. The layers were separated, and the aqueous layer was extracted twice with EtOAc (2×150 ml). Copper salt was filtered from organic layers, which were then dried over sodium sulfate, filtered, and concentrated to obtain the crude product as a thick black oil. Dissolved in MeOH, the crude product was loaded onto silica before silica column chromatography. Collected fractions were pooled and concentrated to give a thick yellow oil containing bi-pyridine. To this oil were added 100 ml EtOAc and 100 ml saturated aqueous CuSO$_4$ solution. The layers were separated, and the aqueous layer was separated to remove blue copper salt. The filtrate was then extracted twice with EtOAc (2×50 ml). Combined organic layers were dried with sodium sulfate, filtered and concentrated to obtain the product 6-chloro-1-cyclopropyl-1H-pyrrolo[3,2-c]pyridine (7A, 11 g, 57%) as a light yellow solid.

Step B: 7B

In a 500 ml pressure vessel, 6-chloro-1-cyclopropyl-1H-pyrrolo[3,2-c]pyridine (7A, 6.2 g, 32 mmol), 4-(prop-1-en-2-yl)benzamide (6.2 g, 39 mmol), palladium(II)acetate (0.29 g, 1.3 mmol), and 2-di-tert-butylphosphino-3,4,5,6-tetramethyl-2',4',6'-triisopropyl-1,1'-biphenyl (2.2 g, 3.9 mmol) were added. Ground-up potassium phosphate tribasic (15 g, 45 mmol) was then added, followed by 1,4-dioxane (130 ml) and t-butanol (32 ml). The vessel was purged with nitrogen for 30 min, before being sealed and heated at 130° C. for 24 hr. After cooling, 250 ml of water and 250 ml EtOAc were successively added. The layers were separated, and the aqueous layer was extracted once more with 200 ml EtOAc. Combined organic layers were dried with Na$_2$SO$_4$, filtered, and concentrated. The crude product was purified by normal phase column chromatography eluting with EtOAc (10-40%) in hexanes. Product-containing fractions were combined and concentrated to obtain the product N-(1-cyclopropyl-1H-pyrrolo[3,2-c]pyridin-6-yl)-4-(prop-1-en-2-yl)benzamide (7B, ~4.2 g, 41%) as a yellow solid.

Example 8

Preparation of Intermediate 8

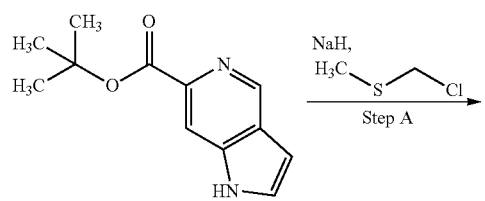

Step A: 8A

To a mixture of tert-butyl 1H-pyrrolo[3,2-c]pyridine-6-carboxylate (1.0 g, 4.6 mmol) in DMF (20 ml) was added sodium hydride (60% in oil) (0.41 g, 10 mmol) and stirred at room temperature for 3 h. To the mixture, (chloromethyl)(methyl)sulfane (0.89 g, 9.2 mmol) was added and stirred at room temperature for 2 h. The reaction mixture was extracted with EtOAc/H₂O. The organic layer was washed with brine, dried over MgSO₄ and concentrated in vacuo. The crude mixture was purified by chromatography (SiO₂, hexanes: EtOAc=50:50) to give tert-butyl 1-(methylthiomethyl)-1H-pyrrolo[3,2-c]pyridine-6-carboxylate (8A, 920 mg, 3.3 mmol, 72% yield) as a yellow oil. ¹H NMR (400 MHz, CHLOROFORM-d) δ ppm 1.61 (s, 9H) 1.94 (s, 3H) 5.15 (s, 2H) 6.64 (d, J=3.28 Hz, 1H) 7.34 (d, J=3.28 Hz, 1H) 8.15 (s, 1H) 8.93 (d, J=1.01 Hz, 1H).

Step B: 8B

A mixture of tert-butyl 1-(methylthiomethyl)-1H-pyrrolo[3,2-c]pyridine-6-carboxylate (8A, 920 mg, 3.3 mmol) and Oxone (4.2 g, 6.8 mmol) in MeOH:H₂O=1:1 (20 ml) was stirred at room temperature for 2 h. The mixture was extracted with EtOAc:H₂O. The organic layer was washed with brine, dried over MgSO₄ and concentrated in vacuo. The crude mixture was purified by chromatography (SiO₂, EtOAc) to give tert-butyl 1-(methylsulfonylmethyl)-1H-pyrrolo[3,2-c]pyridine-6-carboxylate (8B, 820 mg, 80% yield) as a colorless amorphous. ¹H NMR (400 MHz, CHLOROFORM-d) δ ppm 1.70 (s, 9H) 2.75 (s, 3H) 5.40 (s, 2H) 6.88 (dd, J=3.41, 0.88 Hz, 1H) 7.50 (d, J=3.54 Hz, 1H) 8.21 (s, 1H) 9.09 (d, J=1.01 Hz, 1H).

Step C: 8C

A mixture of tert-butyl 1-(methylsulfonylmethyl)-1H-pyrrolo[3,2-c]pyridine-6-carboxylate (8B, 820 mg, 2.7 mmol) in DCM (5 ml) and TFA (5 ml) was stirred at 50° C. for 15 h. The mixture was concentrated in vacuo to give 1-(methylsulfonylmethyl)-1H-pyrrolo[3,2-c]pyridine-6-carboxylic acid (8C, 650 mg, 2.6 mmol, 97% yield) as a brown oil. The material was used for next reaction without further purifications. ESI-MS: m/z 255.1 (M+H)⁺.

Step D: 8D

A mixture of diphenylphosphoryl azide (1.1 g, 3.8 mmol), Et₃N (1.8 ml, 13 mmol) and 1-(methylsulfonylmethyl)-1H-pyrrolo[3,2-c]pyridine-6-carboxylic acid (8C, 650 mg, 2.6 mmol) in 2-methylpropan-2-ol (10 g, 140 mmol) was stirred at room temperature for 1 h and then at 80° C. for 3 h. The mixture was extracted with EtOAc/H₂O. The organic layer was washed with brine, dried over MgSO₄ and concentrated in vacuo. The crude mixture was purified by chromatography (SiO₂, hexane:EtOAc=50:50) to give tert-butyl 1-(methylsulfonylmethyl)-1H-pyrrolo[3,2-c]pyridin-6-ylcarbamate (8D, 410 mg, 1.3 mmol, 50% yield) as a white powder. ¹H NMR (400 MHz, CHLOROFORM-d) δ ppm 0.35-0.44 (m, 2H) 0.57-0.70 (m, 2H) 1.19-1.33 (m, 1H) 1.57 (s, 9H) 3.97 (d, J=6.82 Hz, 2H) 6.52-6.54 (m, 1H) 7.19 (d, J=3.28 Hz, 1H) 7.59 (br. s., 1H) 7.93 (s, 1H) 8.56 (d, J=1.01 Hz, 1H).

Step E: 8E

A mixture of tert-butyl 1-(methylsulfonylmethyl)-1H-pyrrolo[3,2-c]pyridin-6-ylcarbamate (8D, 420 mg, 1.3 mmol) in 4M HCl in dioxane (3 ml) was stirred at 50° C. for 3 h. The mixture was concentrated in vacuo and the resulting residue was dissolved in pyridine (3 ml, 37.1 mmol). To the mixture, methyl 4-(chlorocarbonyl)benzoate (385 mg, 1.936 mmol) was added and stirred at room temperature for 3 h. The mixture was extracted with EtOAc/H₂O. The organic layer was washed with brine, dried over MgSO₄ and concentrated in vacuo. The crude mixture was purified by chromatography (NH—SiO₂, EtOAc) to give methyl 4-(1-(methylsulfonylmethyl)-1H-pyrrolo[3,2-c]pyridin-6-ylcarbamoyl)benzoate (8E, 160 mg, 0.40 mmol, 31% yield) as a white powder. ¹H NMR (400 MHz, DMSO-d₆) δ ppm 3.02 (s, 3H) 3.90 (s, 3H) 5.88 (s, 2H) 6.73 (d, J=2.78 Hz, 1H) 7.49 (d, J=3.28 Hz, 1H) 8.01-8.12 (m, 2H) 8.12-8.19 (m, 2H) 8.46 (s, 1H) 8.70 (s, 1H) 10.93 (s, 1H).

Example 9

N-(1-(cyclopropylmethyl)-1H-pyrrolo[3,2-c]pyridin-6-yl)-4-(2-hydroxypropan-2-yl)benzamide

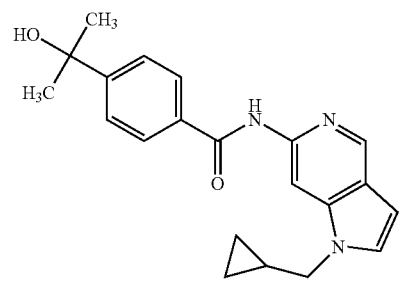 [SMILES: CC(C)(O)c1ccc(C(=O)Nc2cc3c(ccn3CC3CC3)cn2)cc1]

To an ice-cooled solution of methyl 4-(1-(cyclopropylmethyl)-1H-pyrrolo[3,2-c]pyridin-6-ylcarbamoyl)benzoate (2D, 270 mg, 0.773 mmol) in THF (5 ml) was added 3 M methylmagnesium bromide THF solution (1.288 ml, 3.86 mmol). The reaction mixture was stirred at 0° C. for 30 min. The mixture was extracted with EtOAc/H₂O, washed with brine, dried over MgSO₄ and concentrated in vacuo. The crude mixture was purified by chromatography (NH—SiO₂, EtOAc). The fractions were concentrated in vacuo to give the title compound N-(1-(cyclopropylmethyl)-1H-pyrrolo[3,2-c]pyridin-6-yl)-4-(2-hydroxypropan-2-yl)benzamide (110 mg, 0.32 mmol, 40% yield) as a white powder. ¹H NMR (400 MHz, DMSO-d₆) δ ppm 0.39-0.45 (m, 2H) 0.51-0.58 (m, 2H) 1.20-1.31 (m, 1H) 1.46 (s, 6H) 4.05 (d, J=7.07 Hz, 2H) 5.16 (s, 1H) 6.57 (d, J=3.03 Hz, 1H) 7.50 (d, J=3.28 Hz, 1H) 7.59 (d, J=8.59 Hz, 2H) 8.01 (d, J=8.59 Hz, 2H) 8.35 (s, 1H) 8.63 (d, J=1.01 Hz, 1H) 10.51 (s, 1H); m.p 156-157° C.

Example 10

N-(3-bromo-1-(cyclopropylmethyl)-1H-pyrrolo[3,2-c]pyridin-6-yl)-4-(2-hydroxypropan-2-yl)benzamide

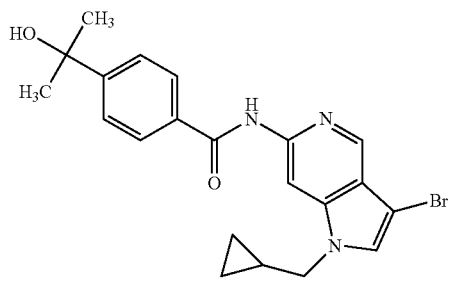 [SMILES: CC(C)(O)c1ccc(C(=O)Nc2cc3c(cn2)c(Br)cn3CC2CC2)cc1]

To an ice-cooled solution of N-(1-(cyclopropylmethyl)-1H-pyrrolo[3,2-c]pyridin-6-yl)-4-(2-hydroxypropan-2-yl)benzamide (Example 9, 75 mg, 0.215 mmol) in DCM (4 ml) was added NBS (38.2 mg, 0.215 mmol). The reaction mixture was stirred at 50° C. for 1 h, and then subjected to chromatography (NH—SiO2, EtOAc). The fractions were concentrated in vacuo and purified by preparatory HPLC to give the title compound N-(3-bromo-1-(cyclopropylmethyl)-1H-pyrrolo[3,2-c]pyridin-6-yl)-4-(2-hydroxypropan-2-yl)benzamide (60 mg, 0.14 mmol, 65% yield) as a white powder. ¹H NMR (400 MHz, DMSO-d₆) δ ppm 0.40-0.48 (m, 2H) 0.52-0.59 (m, 2H) 1.20-1.32 (m, 1H) 1.46 (s, 6H) 4.05 (d, J=7.07 Hz, 2H) 5.17 (s, 1H) 7.59 (d, J=8.59 Hz, 2H) 7.74 (s, 1H) 8.02 (d, J=8.59 Hz, 2H) 8.40 (s, 1H) 8.51 (s, 1H) 10.69 (s, 1H); m.p. 193-194° C.

Example 11

N-(3-bromo-1-ethyl-1H-pyrrolo[3,2-c]pyridin-6-yl)-4-(2-hydroxypropan-2-yl)benzamide

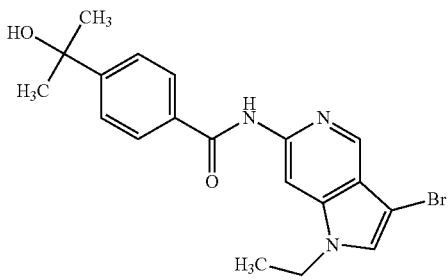 [SMILES: CCn1cc(Br)c2cnc(NC(=O)c3ccc(C(C)(C)O)cc3)cc21]

To an ice-cooled solution of methyl 4-(3-bromo-1-ethyl-1H-pyrrolo[3,2-c]pyridin-6-ylcarbamoyl)benzoate (3D, 300 mg, 0.75 mmol) in THF (5 ml) was added 3M MeMgBr solution in THF (2.5 ml, 7.5 mmol) at 0° C. The reaction mixture was stirred at 0° C. for 2 h. The mixture was quenched with saturated aqueous NH₄Cl and extracted with EtOAc. The organic layer was washed with brine, dried over MgSO₄ and concentrated in vacuo. The crude mixture was crystallized from EtOAc to give the title compound N-(3-bromo-1-ethyl-1H-pyrrolo[3,2-c]pyridin-6-yl)-4-(2-hydroxypropan-2-yl)benzamide (290 mg, 0.72 mmol, 97% yield) as a white powder. ¹H NMR (400 MHz, DMSO-d₆) δ ppm 1.40 (t, J=14.40 Hz, 3H) 1.47 (s, 6H) 4.22 (q, J=7.07 Hz, 2H) 5.13 (s, 1H) 7.60 (d, J=8.34 Hz, 2H) 7.71 (s, 1H) 8.02 (d, J=8.34 Hz, 2H) 8.37 (d, J=0.76 Hz, 1H) 8.51 (s, 1H) 10.63 (s, 1H); mp 209-210° C.

Example 12

N-(1-ethyl-3-methyl-1H-pyrrolo[3,2-c]pyridin-6-yl)-4-(2-hydroxypropan-2-yl)benzamide

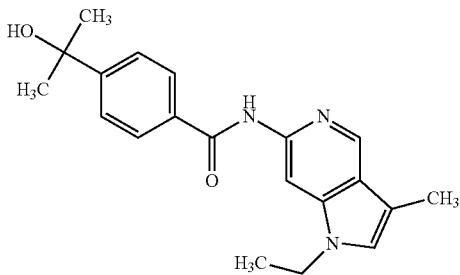 [SMILES: CCn1cc(C)c2cnc(NC(=O)c3ccc(C(C)(C)O)cc3)cc21]

In a 50 ml round bottom flask, methyl 4-(3-bromo-1-ethyl-1H-pyrrolo[3,2-c]pyridin-6-ylcarbamoyl)benzoate (4A, 530 mg, 1.571 mmol) was dissolved in THF (Volume: 12 ml) and the solution was cooled 0° C. in an ice bath. Methyl magnesium bromide (2.6 ml, 7.9 mmol, 3M solution in ether) was then added dropwise. The mixture was then allowed to warm to room temperature for one hour. The reaction was then quenched with saturated NH₄Cl solution at 0° C. and the mixture was extracted with EtOAc (3×50 mL). Combined organic layers were washed with water and brine, dried over sodium sulfate and concentrated. The crude product was purified by using preparatory HPLC (TFA mode, 20-55%). Pure fractions were evaporated to a minimal amount and basified with saturated NaHCO₃. The mixture was extracted with EtOAc (2×75 ml). The organic layers were washed with brine, dried over sodium sulfate and concentrated to obtain the title product (12, 160 mg, 30%) as a white solid. ¹H NMR (400 MHz, DMSO-d6) δ ppm 1.36 (t, J=7.20 Hz, 3H) 1.46 (s, 5H) 2.30 (d, J=0.76 Hz, 3H) 3.29 (s, 1H) 4.12 (q, J=7.24 Hz, 2H) 5.12 (s, 1H) 7.19 (d, J=1.01 Hz, 1H) 7.59 (m, J=8.59 Hz, 2H) 8.01 (m, J=8.34 Hz, 2H) 8.16-8.32 (m, 1H) 8.57 (s, 1H) 10.44 (s, 1H); m.p. 198-200° C.

Example 13

(R)-4-(1,2-dihydroxypropan-2-yl)-N-(1-ethyl-1H-pyrrolo[3,2-c]pyridin-6-yl)benzamide

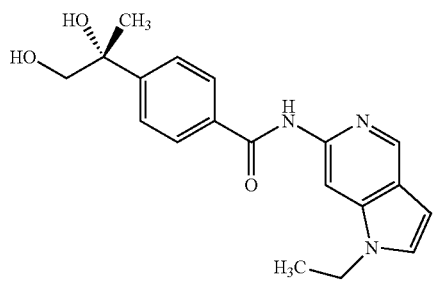 [SMILES: CCn1ccc2cnc(NC(=O)c3ccc([C@@](C)(O)CO)cc3)cc21]

In a 300 mL round-bottomed flask were added N-(1-ethyl-1H-pyrrolo[3,2-c]pyridin-6-yl)-4-(prop-1-en-2-yl)benzamide (4.7 g, 15 mmol) and methanesulfonamide (5A, 1.5 g, 15 mmol) in t-butanol (77 ml). To this at 0° C. was added water (77 ml) and AD-mix beta (27 g). This was vigorously stirred overnight in an ice bath with gradual warming. UPLC showed complete conversion to the desired product. To this mixture was added sodium sulfite (2.4 g, 19 mmol) and this was stirred at room temperature for 30 min. The reaction mixture was partitioned between brine and ethyl acetate, and the aqueous layer was extracted one more time with ethyl acetate. Combined organic layers were washed twice with 2N NaOH, dried over MgSO₄, filtered and concentrated. The crude product was recrystallized from EtOAc and ether to give the title product (R)-4-(1,2-dihydroxypropan-2-yl)-N-(1-ethyl-1H-pyrrolo[3,2-c]pyridin-6-yl)benzamide (13, 3.8 g, 11 mmol, 73% yield) as a light yellow solid. ¹H NMR (DMSO-d₆) δ: 10.52 (s, 1H), 8.63 (s, 1H), 8.32 (s, 1H), 8.02 (s, 2H), 7.58 (d, J=8.3 Hz, 2H), 7.47 (d, J=3.3 Hz, 1H), 6.57 (dd, J=3.3, 0.8 Hz, 1H), 5.05 (s, 1H), 4.77 (t, J=5.8 Hz, 1H), 4.21 (q, J=7.2 Hz, 2H), 3.46 (dd, J=5.7, 2.4 Hz, 2H), 1.43 (s, 4H), 1.36-1.42 (m, 3H); ESI-MS: m/z 340 (M+H)⁺.

Example 14

(R)—N-(3-chloro-1-ethyl-1H-pyrrolo[3,2-c]pyridin-6-yl)-4-(1,2-dihydroxypropan-2-yl)benzamide

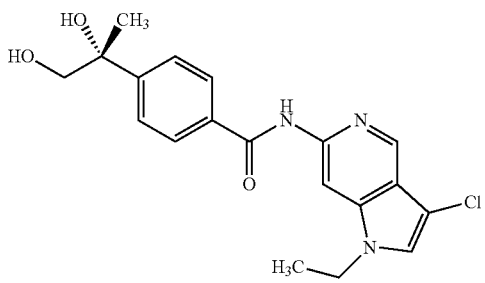 [SMILES: CCn1cc(Cl)c2cnc(NC(=O)c3ccc([C@@](C)(O)CO)cc3)cc21]

In a 200 mL pear flask was added (R)-4-(1,2-dihydroxypropan-2-yl)-N-(1-ethyl-1H-pyrrolo[3,2-c]pyridin-6-yl)benzamide (13, 3.2 g, 7.1 mmol) in anhydrous DMF (45 ml) to give a brown suspension. At room temperature, N-chlorosuccinimide (0.94 g, 7.1 mmol) was added, and the mixture was heated to 60° C. for 4 hours. An additional 0.2 equivalent of N-chlorosuccinimide was added at room temperature. After an additional 1.5 hours of heating at 60° C., the mixture was cooled to room temperature. Brine was added, and the mixture was extracted with ethyl acetate twice. Combined organic layers were washed with brine, dried over $MgSO_4$, filtered and concentrated until a precipitate was formed. Ether was added and the red solid was collected on a fritted filter, while the filtrate was concentrated. The oil was then purified by column chromatography ($SiO_2$, 75-100% EtOAc/hexanes+0.25% MeOH). The product-containing fractions were combined and concentrated. The residue was combined with the red solid collected earlier and the mixture was resuspended in hot EtOAc/methanol mixture. After cooling, the much lighter-colored solid was collected on a fritted-glass filter under nitrogen, and washed with $Et_2O$ to remove most of the colored impurities to give the title compound (R)—N-(3-chloro-1-ethyl-1H-pyrrolo[3,2-c]pyridin-6-yl)-4-(1,2-dihydroxypropan-2-yl)benzamide (14, 1.7 g, 64% yield) as a light-pink solid. $^1$H NMR (DMSO-d6) d: 10.68 (s, 1H), 8.60 (s, 1H), 8.38 (s, 1H), 8.01 (d, J=8.3 Hz, 2H), 7.69 (s, 1H), 7.58 (d, J=8.6 Hz, 2H), 5.05 (s, 1H), 4.76 (t, J=5.8 Hz, 1H), 4.19 (q, J=7.2 Hz, 2H), 3.40-3.50 (m, 2H), 1.42 (s, 3H), 1.38 (t, J=7.3 Hz, 3H); ESI-MS: m/z 374 (M+H)$^+$; m.p. 224.4-225.1° C.

Example 15

N-(3-bromo-1-methyl-1H-pyrrolo[3,2-c]pyridin-6-yl)-4-(2-hydroxypropan-2-yl)benzamide

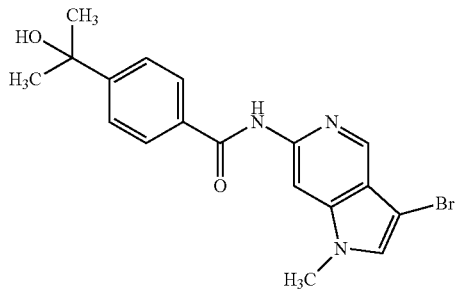 [SMILES: Cn1cc(Br)c2cnc(NC(=O)c3ccc(C(C)(C)O)cc3)cc21]

In a 125 ml round bottom flask, methyl 4-(3-bromo-1-methyl-1H-pyrrolo[3,2-c]pyridin-6-ylcarbamoyl)benzoate (3H, 400 mg, 1.0 mmol) was dissolved in THF (Volume: 20 ml) and the mixture was cooled to 0° C. in an ice bath. Methyl magnesium bromide (1.7 ml, 5.2 mmol) 3M solution in ether was added dropwise. The mixture was allowed to room temperature and stirring continued for 2 hrs. The reaction was quenched with saturated $NH_4Cl$ solution at 0° C. and the mixture was extracted with EtOAc (3×50 mL). Combined organic layers were washed with brine, dried over sodium sulfate and concentrated in vacuo. The product was purified using preparatory HPLC (eluting with TFA-15-65%). Pure fractions were concentrated to a minimal amount and basified with saturated $NaHCO_3$. The aqueous mixture was extracted with EtOAc (2×75 ml), washed with brine, dried over sodium sulfate and concentrated to give the title compound (15, 80%, 320 mg) as a white solid. $^1$H NMR (400 MHz, DMSO-d6) d ppm 1.46 (s, 6H) 3.80 (s, 3H) 5.13 (s, 1H) 7.51-7.69 (m, 3H) 8.02 (d, J=8.08 Hz, 2H) 8.34 (s, 1H) 8.50 (s, 1H) 10.62 (br. s., 1H).

Example 16

(R)—N-(3-bromo-1-methyl-1H-pyrrolo[3,2-c]pyridin-6-yl)-4-(1,2-dihydroxypropan-2-yl)benzamide

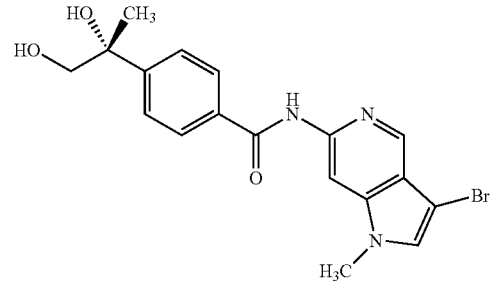 [SMILES: Cn1cc(Br)c2cnc(NC(=O)c3ccc([C@@](C)(O)CO)cc3)cc21]

In a 50 ml pear flask were added N-(3-bromo-1-methyl-1H-pyrrolo[3,2-c]pyridin-6-yl)-4-(prop-1-en-2-yl)benzamide (6A, 400 mg, 1.1 mmol) and methanesulfonamide (100 mg, 1.1 mmol) in t-butanol (5 ml) to give a yellow solution. After water (5 ml) was added, the mixture was cooled to 0° C., and AD-mix beta (1.9 g) was then added. The orange biphasic mixture was kept in ice-bath with gradual warming overnight. Then the reaction was quenched with sodium sulfite (180 mg, 1.4 mmol) at 0° C. After 15 minutes, brine and EtOAc were added and the layers were separated; aqueous layer was extracted with EtOAc once more. Combined organics were washed with 2N KOH solution and then brine, before being dried over $MgSO_4$, filtered and concentrated. The crude product was purified by preparatory HPLC (TFA-15-65%) method. Pure fractions were collected and concentrated to a minimal amount. The residue was lyophilized to give the titled compound (R)—N-(3-bromo-1-methyl-1H-pyrrolo[3,2-c]pyridin-6-yl)-4-(1,2-dihydroxypropan-2-yl)benzamide (16, 52 mg, 11.3% yield) and registered as a TFA salt. $^1$H NMR (400 MHz, DMSO-d6) δ ppm 1.43 (s, 3H) 3.46 (d, J=2.78 Hz, 2H) 3.83 (s, 3H) 4.06 (d, J=8.84 Hz, 1H) 4.23 (d, J=8.84 Hz, 1H) 7.62 (d, J=8.59 Hz, 2H) 7.77 (s, 1H) 8.01 (d, J=8.59 Hz, 2H) 8.23 (s, 1H) 8.62 (s, 1H) 10.92 (s, 1H); ESI-MS: m/z 406 (M+H)$^+$.

Example 17

(R)—N-(1-cyclopropyl-1H-pyrrolo[3,2-c]pyridin-6-yl)-4-(1,2-dihydroxypropan-2-yl)benzamide

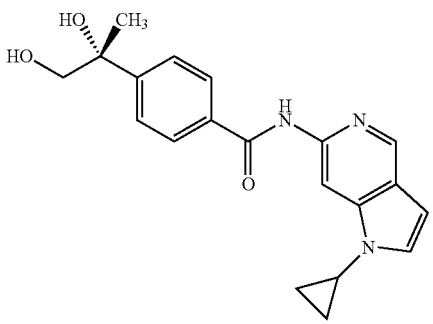 [SMILES: C[C@](O)(CO)c1ccc(C(=O)Nc2cc3c(ccn3C3CC3)cn2)cc1]

In a 1-liter round bottom flask, N-(1-cyclopropyl-1H-pyrrolo[3,2-c]pyridin-6-yl)-4-(prop-1-en-2-yl)benzamide (7B, 8.3 g, 26 mmol) and methanesulfonamide (2.5 g, 26 mmol) were added t-BuOH (130 ml), and the mixture was cooled in ice bath. Water (130 ml) and AD-mix-beta (46 g) were added, and a bi-phase orange solution resulted. Reaction was stirred in ice bath for 3.5 h, when the reaction was completed and quenched with sodium sulfite (4.29 g, 34.0 mmol) in ice bath for 30 min. Brine (200 ml) was added and the mixture was extracted with EtOAc (2×200 ml). Combined organic layers were washed once with 2N KOH (100 ml), followed by brine (100 ml). Organic layers were dried with Na2SO4, filtered, and concentrated to obtained a semi-solid. Crude product was loaded onto a silica gel column eluted with 10-40% EtOAc in hexanes. However, product was not very soluble and most was recovered from the top of the column. The recovered solid was washed with EtOAc and collected by filtration to obtain the product (R)—N-(1-cyclopropyl-1H-pyrrolo[3,2-c]pyridin-6-yl)-4-(1,2-dihydroxypropan-2-yl)benzamide (17) as an off-white solid. The filtrate was concentrated and the solid residue was washed with EtOAc and collected on a filter to obtain an additional 0.91 g of 17 as an off-white solid. The solids were combined (4.9 g, 53%) and used in the next step. $^1$H NMR (400 MHz, DMSO-d$_6$) δ ppm 0.94-1.02 (m, 2H) 1.07-1.14 (m, 2H) 1.43 (s, 3H) 3.42-3.51 (m, 3H) 4.71 (t, J=5.81 Hz, 1H) 4.99 (s, 1H) 6.51 (dd, J=3.28, 1.01 Hz, 1H) 7.37 (d, J=3.28 Hz, 1H) 7.55-7.62 (m, 2H) 8.01 (d, J=8.59 Hz, 2H) 8.46 (t, J=1.01 Hz, 1H) 8.60 (d, J=1.01 Hz, 1H) 10.45 (s, 1H); ESI-MS: m/z 352 (M+H)$^+$; 90.8% ee.

Example 18

(R)-4-(1,2-dihydroxypropan-2-yl)-N-(1-ethyl-3-methyl-1H-pyrrolo[3,2-c]pyridin-6-yl)benzamide

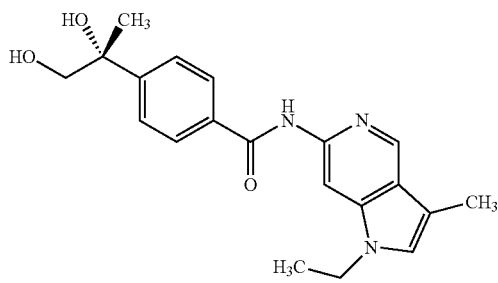 [SMILES: CCn1cc(C)c2cnc(NC(=O)c3ccc([C@@](C)(O)CO)cc3)cc21]

In a 50 mL pear flask were added N-(1-ethyl-3-methyl-1H-pyrrolo[3,2-c]pyridin-6-yl)-4-(prop-1-en-2-yl)benzamide (6B, 640 mg, 2.0 mmol) and methanesulfonamide (190 mg, 2.0 mmol) in t-butanol (12 ml) to give a yellow solution. After water (12 ml) was added, the mixture was cooled to 0° C., and AD-mix beta (3.5 g) was then added. The orange bi-phasic mixture was kept in ice-bath with gradual warming overnight. To quench the reaction, sodium sulfite (330 mg, 2.6 mmol) was added at 0° C. After 15 minutes, brine and EtOAc were added and the layers were separated; aqueous layer was extracted with EtOAc once more. Combined organics were washed with 2N KOH solution and then brine, before being dried over Na$_2$SO$_4$, filtered and concentrated. The crude product was purified by using preparatory reverse phase HPLC (TFA mode, 10-45% ACN in water). Pure fractions were combined, concentrated to a minimal amount and freeze-dried to give the title compound (R)-4-(1,2-dihydroxypropan-2-yl)-N-(1-ethyl-3-methyl-1H-pyrrolo[3,2-c]pyridin-6-yl)benzamide (18, 58 mg, 8.2% yield) as a TFA salt. $^1$H NMR (400 MHz, DMSO-d6) δ ppm 1.33-1.46 (m, 5H) 2.27-2.43 (m, 3H) 3.34-3.57 (m, 2H) 4.11-4.36 (m, 2H) 7.53-7.77 (m, 3H) 7.85-8.07 (m, 3H) 8.92 (br. s., 1H) 11.37 (br. s., 1H); ESI-MS: m/z 354 (M+H)$^+$.

Example 19

N-(1,3-dimethyl-1H-pyrrolo[3,2-c]pyridin-6-yl)-4-(2-hydroxypropan-2-yl)benzamide

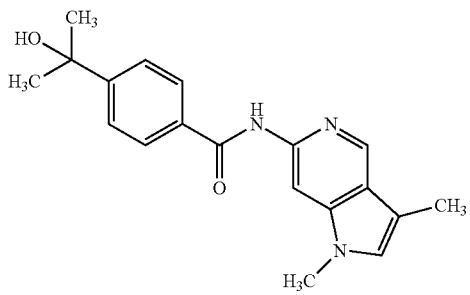 [SMILES: Cc1cn(C)c2cc(NC(=O)c3ccc(C(C)(C)O)cc3)ncc12]

In a 50 ml round bottom flask, methyl 4-(1,3-dimethyl-1H-pyrrolo[3,2-c]pyridin-6-ylcarbamoyl)benzoate (4B, 530 mg, 1.571 mmol) was dissolved in THF (12 ml) and the mixture was to cooled 0° C. in an ice bath. Methyl magnesium bromide (2.6 ml, 7.9 mmol) 3M solution in ether was then added dropwise. The mixture was then allowed to warm to room temperature and stirring continued for 2 hrs. The reaction was then quenched with saturated NH$_4$Cl solution at 0° C. and the aqueous was extracted with EtOAc (3×50 mL). The combined organic layers were dried over sodium sulfate and concentrated. The crude product was purified by preparatory HPLC (TFA mode, 20-55% ACN/H$_2$O). Pure fractions were concentrated to a minimal amount and basified with saturated NaHCO$_3$ solution. The aqueous mixture was extracted with EtOAc (2×75 ml). Combined organic layers were washed with brine, dried over sodium sulfate and concentrated to obtain the title product (19, 160 mg, 20%) as a white solid. $^1$H NMR (400 MHz, DMSO-d6) δ ppm 1.46 (s, 6H) 2.30 (s, 3H)

3.72 (s, 3H) 5.12 (s, 1H) 7.11 (s, 1H) 7.59 (m, J=8.34 Hz, 2H) 8.01 (m, J=8.34 Hz, 2H) 8.22 (s, 1H) 8.57 (s, 1H) 10.44 (s, 1H); m.p. 196-197° C.

Example 20

(R)—N-(3-bromo-1-ethyl-1H-pyrrolo[3,2-c]pyridin-6-yl)-4-(1,2-dihydroxypropan-2-yl)benzamide

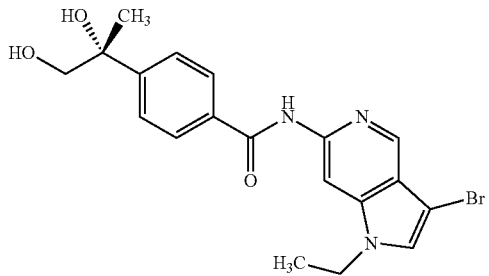 [SMILES: CCn1cc(Br)c2cnc(NC(=O)c3ccc([C@@](C)(O)CO)cc3)cc21]

In a 50 mL pear flask was added (R)-4-(1,2-dihydroxypropan-2-yl)-N-(1-ethyl-1H-pyrrolo[3,2-c]pyridin-6-yl)benzamide (13, 125 mg, 0.368 mmol) in dichloromethane (3.7 ml). At 0° C., 1-bromopyrrolidine-2,5-dione (66 mg, 0.37 mmol) was added to the mixture, and the mixture was kept in the refrigerator over the weekend. After concentration in vacuo, the crude product was purified by preparatory HPLC (TFA mode, 15-65% ACN/water). Combined fractions were neutralized by NaHCO$_3$, concentrated and extracted into EtOAc. Combined organic layers were dried over MgSO$_4$, filtered and concentrated. The residue was then re-suspended in ACN and water, and then freeze dried to give the desired product (R)—N-(3-bromo-1-ethyl-1H-pyrrolo[3,2-c]pyridin-6-yl)-4-(1,2-dihydroxypropan-2-yl)benzamide (20, 10 mg, 7%) as a light orange powder. $^1$H NMR (DMSO-d6) δ 10.62 (s, 1H), 8.50 (s, 1H), 8.36 (s, 1H), 7.97-8.05 (m, 2H), 7.70 (s, 1H), 7.54-7.61 (m, 2H), 5.00 (s, 1H), 4.71 (t, J=5.8 Hz, 1H), 4.21 (d, J=7.1 Hz, 2H), 3.46 (dd, J=5.8, 2.3 Hz, 2H), 1.42 (s, 4H), 1.39 (t, J=7.2 Hz, 3H); ESI-MS: m/z 418 (M+H)$^+$.

Example 21

4-(2-hydroxypropan-2-yl)-N-(1-(methylsulfonylmethyl)-1H-pyrrolo[3,2-c]pyridin-6-yl)benzamide

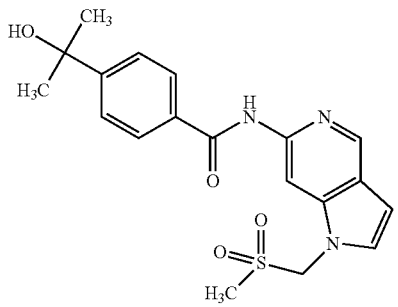 [SMILES: CC(C)(O)c1ccc(C(=O)Nc2cc3c(ccn3CS(C)(=O)=O)cn2)cc1]

To an ice-cooled solution of methyl 4-(1-(methylsulfonylmethyl)-1H-pyrrolo[3,2-c]pyridin-6-ylcarbamoyl)benzoate (8E, 160 mg, 0.40 mmol) in THF (20 ml) was added 3M methylmagnesium bromide THF solution (0.67 ml, 2.0 mmol). The reaction mixture was stirred at 0° C. for 30 min. The mixture was extracted with EtOAc/H$_2$O, washed with brine, dried over MgSO$_4$ and concentrated in vacuo. The crude mixture was subjected to chromatography (NH—SiO$_2$, EtOAc). The fractions were concentrated in vacuo and purified preparatory HPLC to give 4-(2-hydroxypropan-2-yl)-N-(1-(methylsulfonylmethyl)-1H-pyrrolo[3,2-c]pyridin-6-yl)benzamide (21, 1.1 mg, 3.9 μmol, 0.96% yield) as a white powder. $^1$H NMR (400 MHz, DMSO-d$_6$) δ ppm 1.28 (s, 6H) 2.85 (s, 3H) 4.99 (s, 1H) 5.69 (s, 2H) 6.54 (s, 1H) 7.29 (s, 1H) 7.42 (d, J=7.58 Hz, 2H) 7.84 (d, J=7.07 Hz, 2H) 8.30 (s, 1H) 8.51 (s, 1H) 10.41 (br. s., 1H); ESI-MS: m/z 387 (M+H)$^+$.

Example 22

(R)—N-(3-bromo-1-cyclopropyl-1H-pyrrolo[3,2-c]pyridin-6-yl)-4-(1,2-dihydroxypropan-2-yl)benzamide

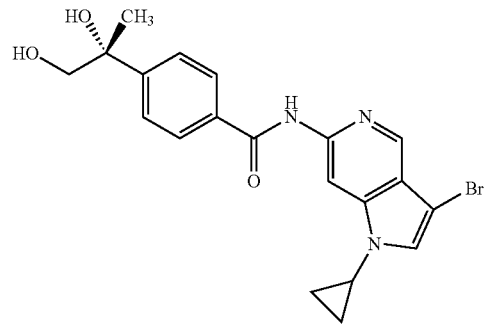

In a 250 ml round bottom flask was added (R)—N-(1-cyclopropyl-1H-pyrrolo[3,2-c]pyridin-6-yl)-4-(1,2-dihydroxypropan-2-yl)benzamide (17, 3.2 g, 9.2 mmol) in N,N-dimethylformamide (31 ml). The mixture was cooled in ice bath, followed by addition of N-bromosuccinimide (1.477 g, 8.30 mmol) in portions. The mixture was stirred in ice bath for 30 min, at which point about ~10% starting material remained. Another 0.1 equivalence (160 mg) of N-bromosuccinimide was added to the reaction mixture, which was stirred in an ice bath for another 30 min. Brine (200 ml) was added, followed by extraction with EtOAc (2×200 mL). Organic layers were combined. After drying and filtering, a suspension was obtained upon concentration. The solid was collected on a filtered, and then washed with 10 ml EtOAc. The resulting 2 g of filtrated solid was purified by silica gel column chromatography, eluting with 5-10% MeOH in EtOAc. Product-containing fractions were combined and concentrated to yield a solid which was washed twice with EtOAc (2×10 ml). The title compound (22, 0.62 g, 16%) was obtained as a pink solid. $^1$H NMR (400 MHz, DMSO-d6) δ ppm 0.98-1.04 (m, 2H) 1.05-1.13 (m, 2H) 1.42 (s, 3H) 3.42-3.54 (m, 3 H) 4.71 (t, J=5.81 Hz, 1H) 4.99 (s, 1H) 7.58 (d, J=8.59 Hz, 2H) 7.62 (s, 1H) 8.01 (d, J=8.59 Hz, 2H) 8.48 (d, J=0.76 Hz, 2H) 8.51 (d, J=0.76 Hz, 2H) 10.63 (s, 1H); ESI-MS: m/z 432 (M+H)$^+$. Additional amounts of the title compound were obtained by combining filtrates and re-purifying them by silica gel column chromatography.

Example 23

(R)—N-(3-chloro-1-cyclopropyl-1H-pyrrolo[3,2-c]pyridin-6-yl)-4-(1,2-dihydroxypropan-2-yl)benzamide

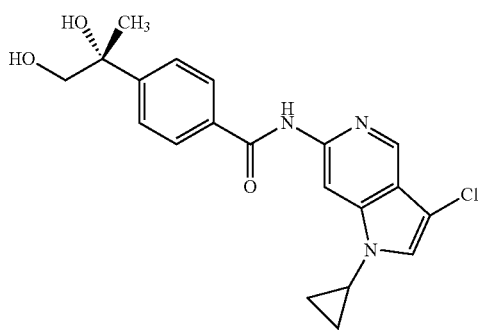 [SMILES: C[C@](O)(CO)c1ccc(C(=O)Nc2cc3c(cn2)c(Cl)cn3C2CC2)cc1]

In a 100 mL round bottom flask was added (R)—N-(1-cyclopropyl-1H-pyrrolo[3,2-c]pyridin-6-yl)-4-(1,2-dihydroxypropan-2-yl)benzamide (200 mg, 0.57 mmol) in N,N-dimethylformamide (2.8 mL) to give a light yellow solution. This was followed by addition of N-chlorosuccinimide (76 mg, 0.57 mmol) at room temperature and the mixture was heated to 60° C. After 4 h, another 0.1 eq of N-chlorosuccinimide was added and the mixture was heated for another hour. The mixture was directly loaded onto a silica gel column, eluting with 20-70% EtOAc in hexanes for purification. Product-containing fractions were combined and a pinkish solid was formed upon evaporation of solvents. The solid was collected and washed with 5 ml EtOAc to give the title compound (23, 71 mg, 32%) as a light pink product. $^1$H NMR (400 MHz, DMSO-d6) δ ppm 0.99-1.06 (m, 2H) 1.10 (dd, J=7.07, 4.55 Hz, 2H) 1.43 (s, 3H) 3.42-3.54 (m, 3H) 4.72 (br. s., 1H) 5.00 (s, 1H) 7.56-7.62 (m, 3H) 8.02 (d, J=8.59 Hz, 2H) 8.52 (d, J=0.76 Hz, 1H) 8.56-8.60 (m, 1H) 10.64 (s, 1H); ESI-MS: m/z 386 (M+H)$^+$.

Example 24

N-(3-chloro-1-methyl-1H-pyrrolo[3,2-c]pyridin-6-yl)-4-(2-hydroxypropan-2-yl)benzamide

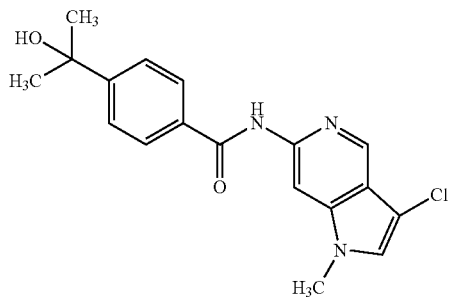 [SMILES: Cn1cc(Cl)c2cnc(NC(=O)c3ccc(C(C)(C)O)cc3)cc21]

Step A:
In a 250 ml round bottom flask, methyl 4-(1-methyl-1H-pyrrolo[3,2-c]pyridin-6-ylcarbamoyl)benzoate (4C, 4.5 g, 15 mmol) was dissolved in THF (30 ml) and the mixture was cooled 0° C. in an ice bath. To this was added dropwise methylmagnesium bromide (24 ml, 73 mmol) as a 3M solution in ether. The mixture was allowed to room temperature and stirring continued for 1.5 hrs. The mixture was cooled down to 0° C. and quenched with saturate NH$_4$Cl solution. The aqueous mixture was extracted with EtOAc (3×250 mL), and the combined organic layers were washed with brine. The combined organic layer was dried over sodium sulfate, filtered and concentrated. The resulting solid was triturated with diethyl ether and collected by filtration to obtain the desired product 4-(2-hydroxypropan-2-yl)-N-(1-methyl-1H-pyrrolo[3,2-c]pyridin-6-yl)benzamide (2.2 g, 49%); m.p. 173-175° C. The solid was used in the next step without further purification.

Step B:
In a 125 ml round bottom flask, 4-(2-hydroxypropan-2-yl)-N-(1-methyl-1H-pyrrolo[3,2-c]pyridin-6-yl)benzamide (2.8 g, 9.05 mmol) was dissolved in DMF (25 ml). To this was added N-chlorosuccinimide (1.5 g, 11 mmol) and the mixture was stirred at 50° C. for 3 hours. The mixture was then poured into 50 ml water and then extracted with ethyl acetate (3×100 ml). Combined organic layers were dried over sodium sulfate and concentrated. The residue was purified by preparatory HPLC (RFA-mode: eluting with 25-55% ACN in water). Fractions containing the desired mono chlorinated product were combined and concentrated. To the residue was added saturated NaHCO$_3$ and the aqueous mixture was extracted with ethyl acetate (2×100 ml). Combined organic layers were dried over sodium sulfate, filtered and concentrated to obtain the title compound (840 mg, 27% yield) as a tan solid. $^1$H NMR (400 MHz, DMSO-d6) δ ppm 1.25-1.26 (m, 1H) 1.46 (s, 139H) 3.66-3.86 (m, 3H) 5.17 (s, 1H) 7.40-7.69 (m, 3H) 8.01 (d, J=8.59 Hz, 2H) 8.34 (s, 1H) 8.59 (s, 1H) 10.68 (s, 1H)

Example 25

N-(2,3-dichloro-1-methyl-1H-pyrrolo[3,2-c]pyridin-6-yl)-4-(2-hydroxypropan-2-yl)benzamide

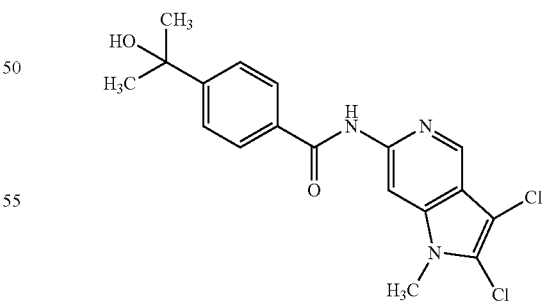

The title compound was obtained as a side-product in the synthesis of Example 24. $^1$H NMR (400 MHz, DMSO-d6) δ ppm 1.46 (s, 5H) 3.76 (s, 3H) 5.17 (s, 1H) 7.59 (m, J=8.34 Hz, 2H) 8.01 (m, J=8.34 Hz, 2H) 8.37 (s, 1H) 8.58 (br. s., 1H) 10.74 (s, 1H)

Example 26

(S)—N-(3-chloro-1-ethyl-1H-pyrrolo[3,2-c]pyridin-6-yl)-4-(1,2-dihydroxypropan-2-yl)benzamide

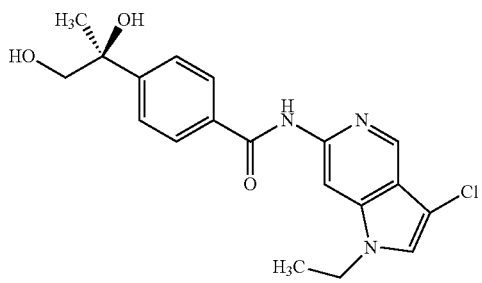 [SMILES: CCn1cc(Cl)c2cnc(NC(=O)c3ccc([C@](C)(O)CO)cc3)cc21]

In a 50 mL pear flask was added (S)-4-(1,2-dihydroxypropan-2-yl)-N-(1-ethyl-1H-pyrrolo[3,2-c]pyridin-6-yl)benzamide (92 mg, 0.27 mmol) in DMF (2 ml) to give a solution. At room temperature 1-chloropyrrolidine-2,5-dione (36 mg, 0.27 mmol) was added, and the mixture was heated to 60° C. for 4 hours, at which point the reaction seemed to have stalled. An additional 0.2 equivalence of 1-chloropyrrolidine-2,5-dione was added, and the mixture was heated to 60° C. for another hour. The mixture was then cooled, and partitioned between brine and EtOAc. The aqueous layer was further extracted with EtOAc, and the organic layers were combined, washed with brine, dried, filtered and concentrated in vacuo. The residue was then triturated with hot EtOAc, and the resulting precipitate was collected on a fritted-glass funnel. The collected solid was then recrystallized from EtOH to give the product (S)—N-(3-chloro-1-ethyl-1H-pyrrolo[3,2-c]pyridin-6-yl)-4-(1,2-dihydroxypropan-2-yl)benzamide (23 mg, 0.062 mmol, 22% yield) as a pink solid. $^1$H NMR (DMSO-d6) δ 10.68 (s, 1H), 8.60 (s, 1H), 8.37 (s, 1H), 8.02 (s, 2H), 7.69 (s, 1H), 7.59 (s, 2H), 5.05 (s, 1H), 4.76 (t, J=5.8 Hz, 1H), 4.19 (q, J=7.1 Hz, 2H), 3.40-3.50 (m, 2H), 1.34-1.45 (m, 6H); m.p. 223.0-223.9° C.

Example 27

(R)-4-(1,2-dihydroxypropan-2-yl)-N-(1-ethyl-1H-pyrrolo[3,2-c]pyridin-6-yl)-3-methylbenzamide

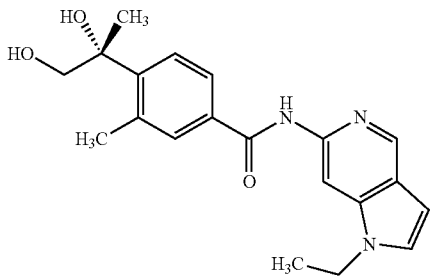 [SMILES: CCn1ccc2cnc(NC(=O)c3ccc([C@@](C)(O)CO)c(C)c3)cc21]

To N-(1-ethyl-1H-pyrrolo[3,2-c]pyridin-6-yl)-3-methyl-4-(prop-1-en-2-yl)benzamide (100 mg, 0.31 mmol) and methanesulfonamide (30 mg, 0.31 mmol) were added t-BuOH (1.6 mL). The mixture was cooled in ice bath, and then water (1.6 mL) and AD-mix-beta (550 mg, 0.39 mmol) were added to give a bi-phase orange solution. The reaction was stirred at 0° C. with slow warming to room temperature overnight. The mixture was again cooled in ice bath the next day, and a total of 500 mg of AD-mix-beta was added. No further conversion was observed after 6 hours. To the reaction mixture cooled in ice bath was added 120 mg of sodium sulfite. After being stirred for 20 min, the mixture was charged with brine (5 ml) and the mixture was extracted with EtOAc (2×5 ml). Combined organic layers were washed once with 2N KOH (5 ml) and then once with brine (5 ml). The organic layers were dried over Na$_2$SO$_4$, filtered, and concentrated. $^1$H NMR (DMSO-d6) δ: 10.47 (br. s., 1H), 8.65 (br. s., 1H), 8.29 (br. s., 1H), 7.81 (d, J=8.3 Hz, 2H), 7.56 (d, J=8.1 Hz, 1H), 7.48 (d, J=3.3 Hz, 1H), 6.58 (d, J=3.0 Hz, 1H), 4.91 (s, 1H), 4.76 (br. s., 1H), 4.16-4.28 (m, 2H), 3.60 (br. s., 2H), 2.59 (s, 3H), 1.48 (s, 3H), 1.39 (t, J=7.2 Hz, 3H); ESI-MS: m/z 354 (M+H)$^+$.

Example 28

N-(3-chloro-1-cyclopropyl-1H-pyrrolo[3,2-c]pyridin-6-yl)-4-(1-hydroxy-2-methylpropan-2-yl)benzamide

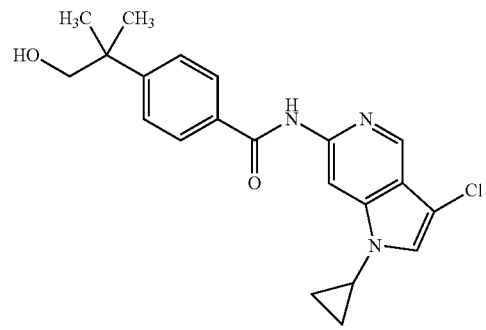 [SMILES: CC(C)(CO)c1ccc(C(=O)Nc2cc3c(cn2)c(Cl)cn3C2CC2)cc1]

Step A:

In a microwave vial were added 6-chloro-1-cyclopropyl-1H-pyrrolo[3,2-c]pyridine (250 mg, 1.3 mmol), 4-(1-(tert-butyldimethylsilyloxy)-2-methylpropan-2-yl)benzamide (400 mg, 1.3 mmol), palladium(II)acetate (44 mg, 0.20 mmol), and 2-di-tert-butylphosphino-3,4,5,6-tetramethyl-2',4',6'-triisopropyl-1,1'-biphenyl (90 mg, 0.156 mmol). To this mixture was then added ground potassium phosphate (590 mg, 1.8 mmol), followed by 1,4-dioxane (4.3 mL) and t-butanol (1.1 mL). An additional 50 mg of Pd(OAc)$_2$ was added to the solution. After purging the vial with N$_2$, the mixture was then heated in an oil bath at 140° C. overnight. To the dark mixture at room temperature, EtOAc and water were added. The mixture was filtered to remove Pd. The bi-phase filtrate was then partitioned, and the aqueous phase was further extracted with 10 ml EtOAc. Combined organic layers were dried over Na$_2$SO$_4$, filtered, and concentrated in vacuo. The crude product was purified by column chromatography (SiO$_2$, 20-60% EtOAc/hexanes) to give the desired product 4-(1-(tert-butyldimethylsilyloxy)-2-methylpropan-2-yl)-N-(1-cyclopropyl-1H-pyrrolo[3,2-c]pyridin-6-yl)benzamide as an yellow oil (40 mg).

Step B:

To 4-(1-(tert-butyldimethylsilyloxy)-2-methylpropan-2-yl)-N-(1-cyclopropyl-1H-pyrrolo[3,2-c]pyridin-6-yl)benzamide (40 mg, 0.086 mmol) was added N,N-dimethylformamide (0.43 mL) to give a light yellow solution. To this was added NCS (10 mg, 0.078 mmol) and the mixture was heated at 60° C. for 3 hr. Water (5 ml) was added and the mixture was extracted with EtOAc (2×5 ml). Combined organic layers were dried over Na$_2$SO$_4$, filtered, and concentrated in vacuo. The crude product 4-(1-(tert-butyldimethylsilyloxy)-2-methylpropan-2-yl)-N-(3-chloro-1-cyclopropyl-1H-pyrrolo[3,2-c]pyridin-6-yl)benzamide was used in the next step without further purification.

Step C:

To 4-(1-(tert-butyldimethylsilyloxy)-2-methylpropan-2-yl)-N-(3-chloro-1-cyclopropyl-1H-pyrrolo[3,2-c]pyridin-6-yl)benzamide (20 mg, 0.040 mmol) was added THF (800 µA). At room temperature, TBAF (1.0M solution in THF, 50 µl) was added. The mixture was heated to 60° C. for 1 hr. After reaction was completed, 2 ml saturated NH$_4$Cl was added and the mixture was extracted with EtOAc (3×2 ml). Organic layers were combined, dried, filtered and concentrated. The crude product was purified by preparatory HPLC (TFA mode, 20-45% ACN in water). Product containing fractions were combined, and then extracted with EtOAc to remove residual TBAF to give the title compound as a white solid (13 mg, 84%). $^1$H NMR (400 MHz, DMSO-d$_6$) δ ppm 0.98-1.05 (m, 1H) 1.05-1.12 (m, 1H) 1.26 (d, J=1.52 Hz, 7H) 3.44-3.55 (m, 3H) 4.77 (br. s., 1H) 7.50 (dd, J=8.59, 2.27 Hz, 2H) 7.62 (d, J=6.06 Hz, 1H) 7.96-8.05 (m, 2H) 8.34 (d, J=1.01 Hz, 1H) 8.51 (d, J=1.01 Hz, 1H) 8.61 (d, J=1.01 Hz, 1H) 8.57 (d, J=0.76 Hz, 1H) 10.64 (d, J=9.09 Hz, 1H); ESI-MS: m/z 384 (M+H)$^+$.

Example 29

(S)—N-(3-chloro-1-methyl-1H-pyrrolo[3,2-c]pyridin-6-yl)-4-(1,2-dihydroxypropan-2-yl)benzamide

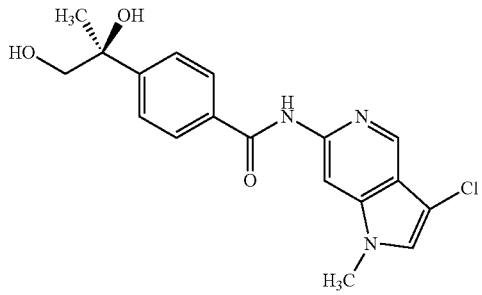 [SMILES: Cn1cc(Cl)c2cnc(NC(=O)c3ccc([C@](C)(O)CO)cc3)cc21]

Step A:

N-(1-methyl-1H-pyrrolo[3,2-c]pyridin-6-yl)-4-(prop-1-en-2-yl)benzamide (900 mg, 3.1 mmol) and methanesulfonamide (290 mg, 3.1 mmol) were suspended in t-butanol (10 ml). After water (10 ml) was added, the mixture was cooled to 0° C., and AD-mix alpha (5.4 g, 3.9 mmol) was then added. The orange bi-phasic mixture was kept in ice-bath with gradual warming overnight. The reaction was quenched with sodium sulfite (510 mg, 4.0 mmol) at 0° C. After 15 minutes, brine and EtOAc were added and the layers were separated; aqueous layer was extracted with EtOAc once more. Combined organic layers were washed with 2N KOH solution and then brine, before being dried over MgSO$_4$, filtered and concentrated. The crude product was purified by preparatory HPLC (TFA mode, 15-65% ACN in water). Pure compound fractions were combined and concentrated to a minimal amount, then added sat. NaHCO$_3$ solution and extracted into EtOAc (2×100 ml). Combined organic layer was dried over sodium sulfate and evaporated to give the desired product (S)-4-(1,2-dihydroxypropan-2-yl)-N-(1-methyl-1H-pyrrolo[3,2-c]pyridin-6-yl)benzamide.

Step B:

(S)-4-(1,2-dihydroxypropan-2-yl)-N-(1-methyl-1H-pyrrolo[3,2-c]pyridin-6-yl)benzamide (650 mg, 2.0 mmol) was dissolved in DMF (25 ml) and NCS (270 mg, 2.0 mmol) was added to the mixture, which was stirred at 50° C. for 16 hours. The mixture was then poured into 50 ml ice water and was extracted into ethyl acetate (3×100 ml). Combined organic layers were dried over sodium sulfate and concentrated in vacuo. The crude product was purified by preparatory HPLC (TFA mode, 15-50% ACN in water). Fractions containing the desired mono chlorinated product were combined, concentrated, washed with saturated NaHCO$_3$ and brine, and then extracted into ethyl acetate (2×100 ml). Combined organic layers were dried over sodium sulfate, filtered and concentrated in vacuo to obtain the title compound (S)—N-(3-chloro-1-methyl-1H-pyrrolo[3,2-c]pyridin-6-yl)-4-(1,2-dihydroxypropan-2-yl)benzamide (120 mg, 0.32 mmol, 16%) as a brown solid. $^1$H NMR (400 MHz, DMSO-d$_6$) δ ppm 1.43 (s, 2H) 2.43-2.64 (m, 1H) 3.46 (dd, J=5.56, 2.53 Hz, 2H) 3.69-3.84 (m, 2H) 4.76 (t, J=5.81 Hz, 1H) 5.04 (s, 1H) 7.40-7.67 (m, 2H) 8.02 (d, J=8.59 Hz, 1H) 8.21-8.40 (m, 1H) 8.59 (s, 1H) 10.65 (s, 1H); ESI-MS: m/z 360 (M+H)$^+$; m.p. 210-212° C.

Example 30

(S)—N-(2,3-dichloro-1-methyl-1H-pyrrolo[3,2-c]pyridin-6-yl)-4-(1,2-dihydroxypropan-2-yl)benzamide

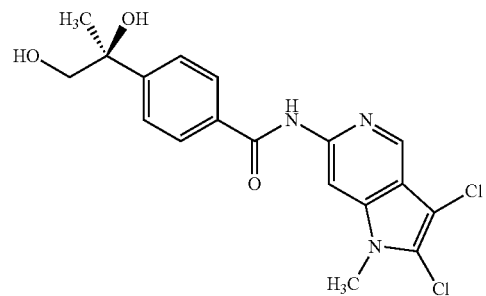 [SMILES: Cn1c(Cl)c(Cl)c2cnc(NC(=O)c3ccc([C@](C)(O)CO)cc3)cc21]

The title compound was obtained as a side-product in the synthesis of Example 29. $^1$H NMR (400 MHz, DMSO-d$_6$) δ ppm 1.43 (s, 2H) 1.44-1.45 (m, 1H) 3.46 (d, J=2.53 Hz, 1H) 3.79 (s, 2H) 4.06 (d, J=8.84 Hz, 2H) 4.23 (d, J=8.84 Hz, 3H) 7.60 (d, J=8.59 Hz, 1H) 7.87-8.12 (m, 1H) 8.63 (s, 1H); ESI-MS: m/z 394 (M+H)$^+$; m.p. 205-208° C.

Example 31

(R)—N-(3-chloro-1-methyl-1H-pyrrolo[3,2-c]pyridin-6-yl)-4-(1,2-dihydroxypropan-2-yl)benzamide

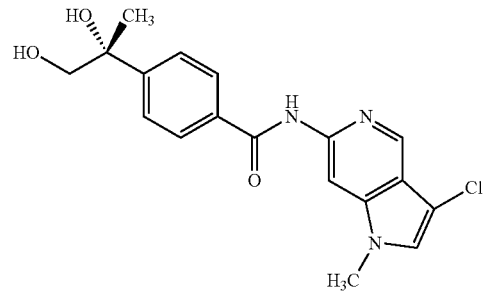 [SMILES: Cn1cc(Cl)c2cnc(NC(=O)c3ccc([C@@](C)(O)CO)cc3)cc21]

Step A:

N-(1-methyl-1H-pyrrolo[3,2-c]pyridin-6-yl)-4-(prop-1-en-2-yl)benzamide (900 mg, 3.1 mmol) and methanesulfonamide (290 mg, 3.1 mmol) were suspended in t-butanol (10 ml). After water (10 ml) was added, the mixture was cooled to 0° C., and AD-mix beta (5.4 g, 3.9 mmol) was then added. The orange bi-phasic mixture was kept in ice-bath with gradual warming overnight. The reaction was quenched with sodium sulfite (510 mg, 4.0 mmol) at 0° C. After 15 minutes, brine and EtOAc were added and the layers were separated; aqueous layer was extracted with EtOAc once more. Combined organic layers were washed with 2N KOH solution and then brine, before being dried over $MgSO_4$, filtered and concentrated. The crude product was purified by preparatory HPLC (TFA mode, 15-65% ACN in water). Pure compound fractions were combined and concentrated to a minimal amount, then added sat. $NaHCO_3$ solution and extracted into EtOAc (2×100 ml). Combined organic layer was dried over sodium sulfate and evaporated to give the desired product (R)-4-(1,2-dihydroxypropan-2-yl)-N-(1-methyl-1H-pyrrolo[3,2-c]pyridin-6-yl)benzamide.

Step B:

(R)-4-(1,2-dihydroxypropan-2-yl)-N-(1-methyl-1H-pyrrolo[3,2-c]pyridin-6-yl)benzamide (750 mg, 2.3 mmol) was dissolved in DMF (20 ml) and NCS (310 mg, 2.3 mmol) was added to it. Stirring continued at 50° C. for 3 hours. The mixture was poured into 50 ml ice water and was extracted into ethyl acetate (3×100 ml). Combined organic layers were dried over sodium sulfate and concentrated in vacuo. The crude product was purified by preparatory HPLC (TFA mode, 15-50% ACN in water). Fractions containing the desired mono chlorinated product were combined, concentrated, washed with saturated $NaHCO_3$ and brine, and then extracted into ethyl acetate (2×100 ml). Combined organic layers were dried over sodium sulfate, filtered and concentrated in vacuo to obtain the title compound (R)—N-(3-chloro-1-methyl-1H-pyrrolo[3,2-c]pyridin-6-yl)-4-(1,2-dihydroxypropan-2-yl)benzamide (18 mg, 0.49 mmol, 21%) as a light yellow solid. $^1$H NMR (400 MHz, DMSO-$d_6$) δ ppm 1.42 (s, 3H) 3.45 (dd, J=5.81, 2.53 Hz, 2H) 3.78 (s, 2H) 4.74 (t, J=5.81 Hz, 1H) 5.03 (s, 1H) 7.46-7.69 (m, 2H) 8.01 (d, J=8.59 Hz, 2H) 8.34 (d, J=0.76 Hz, 1H) 8.59 (d, J=0.76 Hz, 1H) 10.64 (s, 1H); ESI-MS: m/z 360 (M+H)$^+$; m.p. 210-212° C.

Example 32

(R)—N-(2,3-dichloro-1-methyl-1H-pyrrolo[3,2-c]pyridin-6-yl)-4-(1,2-dihydroxypropan-2-yl)benzamide

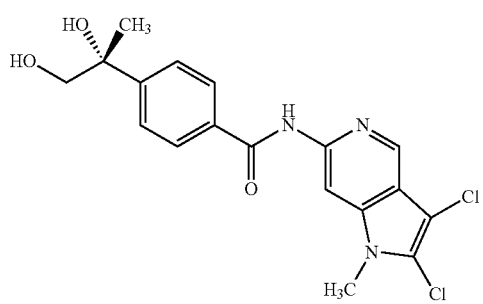 [SMILES: Cn1c(Cl)c(Cl)c2cnc(NC(=O)c3ccc([C@@](C)(O)CO)cc3)cc21]

The title compound was obtained as a side-product in the synthesis of Example 31. $^1$H NMR (400 MHz, DMSO-$d_6$) δ ppm 1.43 (s, 2H) 1.44-1.45 (m, 1H) 3.46 (d, J=2.53 Hz, 1H) 3.79 (s, 2H) 4.06 (d, J=8.84 Hz, 2H) 4.23 (d, J=8.84 Hz, 3H) 7.60 (d, J=8.59 Hz, 1H) 7.87-8.12 (m, 1H) 8.63 (s, 1H); ESI-MS: m/z 394 (M+H)$^+$.

Example 33

(R)—N-(3-chloro-1-ethyl-1H-pyrrolo[3,2-c]pyridin-6-yl)-4-(1,2-dihydroxypropan-2-yl)-3-methylbenzamide

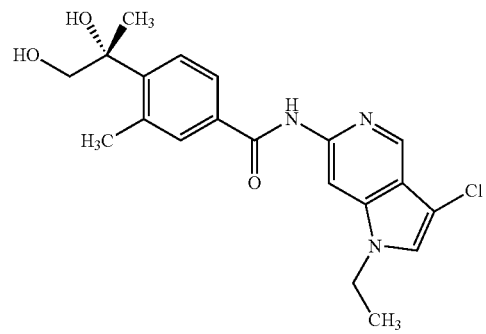 [SMILES: CCn1cc(Cl)c2cnc(NC(=O)c3ccc([C@@](C)(O)CO)c(C)c3)cc21]

(R)-4-(1,2-dihydroxypropan-2-yl)-N-(1-ethyl-1H-pyrrolo[3,2-c]pyridin-6-yl)-3-methylbenzamide (40 mg, 0.11 mmol) was dissolved in N,N-dimethylformamide (0.57 mL) to give a light yellow solution. NCS (14 mg, 0.10 mmol) was then added at room temperature. The mixture was heated mixture at 60° C.; after 3 hr, another 15 mg of NCS was added, and the reaction completed after 1 hr. The mixture was diluted with MeOH (1 ml) and then purified by preparatory HPLC (basic mode, 20-70% ACN in water). Product-containing fractions were combined, concentrated and freeze-dried to obtain the title compound as a tan colored solid (10 mg, 23%). $^1$H NMR (400 MHz, DMSO-$d_6$) δ ppm 1.38 (t, J=7.20 Hz, 3H) 1.48 (s, 3H) 2.58 (s, 3H) 3.58-3.64 (m, 2H) 4.19 (q, J=7.24 Hz, 2H) 4.77 (br. s., 1H) 4.92 (br. s., 1H) 7.55 (d, J=8.34 Hz, 1H) 7.68 (s, 1H) 7.76-7.88 (m, 2H) 8.36 (d, J=0.76 Hz, 1H) 8.59 (d, J=1.01 Hz, 1H) 10.58 (s, 1H); ESI-MS: m/z 388 (M+H)$^+$.

Example A

Preparation of ASK1 Protein

Cloning of cDNA encoding human ASK1 was conducted by PCR using primers, 5'-AAAAGTCGACATGGACTACAAGGACGACGATGACAAGGTGAACAC CATTACCGAAGAGAAGGGGA-3' (SEQ ID NO: 1) and 5'-AAAGCGGCCGCTCAA GTCTGTTTGTTTCGAAAGTCAATG-3' (SEQ ID NO: 2), from human heart cDNA library (Becton, Dickinson and Company). The PCR product was subjected to agarose gel (1%) electrophoresis, a 2.2 kb DNA fragment containing an ASK1 gene was recovered from the gel, and then digested with restriction enzymes, NotI and SalI, and inserted into a plasmid pFASTBAC1 (Invitrogen) to prepare a plasmid pFB-ASK1. The insert was verified by sequencing. Recombinant baculovirus was prepared according to the procedure of the Bac-to-Bac baculovirus expression system (Invitrogen).

Sf-21 cells were seeded to achieve $1×10^6$ cells/mL in 100 mL of Sf-900 II SFM medium (Invitrogen) which contains 10% fetal calf serum and then cultured at 27° C. for 24 hrs. To express ASK1 in cells, 0.15 mL of the recombinant baculovirus virus stock was added to cells, and the then cultured for 60 hrs. The cells were separated from the culture solution by centrifugation at 3000 rpm for 10 min and washed once with PBS. The cells were suspended in 10 mL of lysis buffer (25 mM HEPES (pH 7.5), 1% Triton X, 130 mM NaCl, 1 mM EDTA, 1 mM DTT, 25 mM (3-glycerophosphate, Protease inhibitor complete (Roche), 1 mM sodium orthovanadate) and ruptured by four times of treatment with a homogenizer (POLYTRON) at 20000 rpm for 30 seconds. Active ASK1 protein was purified from a supernatant obtained by centrifugal separation at 40000 rpm for 45 min using anti-FLAG M2 Affinity Gel (Sigma).

Example B

Scintillation Assay for Measuring the Inhibitory Effect of Exemplified Compounds of the Invention Against ASK1

The test compounds (2.5 μL) dissolved in DMSO were added to wells containing 37.5 μL of the reaction solution (25 mM HEPES (pH 7.5), 10 mM magnesium acetate, 1 mM DTT) including 30 ng of active ASK1 protein and 1 μg of myelin basic protein (Wako), and incubated at room temperature for 5 min. To start the reaction, 10 μL of ATP solution (2.5 μM ATP, 0.1 μCi [γ-$^{32}$P]ATP) was added to wells. After incubating at room temperature for 30 min, the reaction was terminated by adding 50 μL of 20% TCA solution. The reaction solution was incubated at 4° C. for 30 min and an acid-insoluble fraction was transferred onto a GF/C filter (Packard) with Cell Harvester (Packard), and washed with 250 mM phosphoric acid. After drying at 45° C. for 60 min., 40 μL of Microscint 0 (Packard) was added and the radioactivity was measured with TopCount (Packard). The concentrations ($IC_{50}$ value) of the test compounds necessary for 50% inhibition of kinase activity were calculated by PRISM 3.0 (Graphpad Software).

Example C

Homogeneous Time-Resolved Fluorescence (HTRF) Assay for Measuring the Inhibitory Effect of Exemplified Compounds of the Invention Against ASK1

Recombinant human ASK1 is purchased from Millipore (Cat #14-606). The enzymatic assay of ASK1 is set up by using HTRF® KinEASE™ STK S3 kit, the Universal Assay for Serine/Threonine Kinases kit from CisBio.

The inhibitory properties of compounds to ASK1 may be determined using a white 384-well-plate format under the following reaction conditions: 25 nM ASK1, 1 μM CisBio STK S3-biotion peptide, 100 μM ATP, and 1%-2% DMSO in kinase assay buffer of 50 mM HEPES, pH 7.3, 10 mM NaCl, 10 mM $MgCl_2$, 0.01% Brij35, 0.2 mM EDTA, and 1 mM DTT. Reaction product is determined quantitatively by HTRF after the addition of detection reagent SA-XL665 and STK-antibody-cryptate.

The assay reaction may be initiated as follows: 2 μl of the mixture of 3 μM CisBio STK S3-biotion peptide and 300 μM ATP with 2 μl of test compound (2 fold serial dilutions for 11 data points for each inhibitor) containing 3%-6% DMSO are added to each well of the plate, followed by the addition of 2 μL of 75 nM ASK1 to initiate the reaction (final enzyme concentration was 25 nM for ASK1). The reaction mixture may then be incubated at room temperature for 1 hour, and quenched and developed by the addition of 6 μL of 100-fold diluted STK-antibody-Cryptate and 250 nM SA-XL665 in Cisbio HTRF detection buffer (50 mM HEPES, pH7.0, 0.1% BSA, 0.8 M KF, and 20 mM EDTA). The fluorescence intensity is measured at 620 nm (Cryptate) and 665 nm (XL665) after a 1-2 hour incubation at room temperature. A ratio is calculated (665/620) for each well and is fitted to the standard $IC_{50}$ curve to determine inhibition constants ($IC_{50}$).

Example D

In Vitro $IC_{50}$ Values of Compounds of the Invention Against ASK1

The enzyme activities of the compounds of the present invention against ASK1 were determined using the assay disclosed in Examples B and C. The resulted $IC_{50}$ values are reported in Table 1.

TABLE 1

| $IC_{50}$ of Exemplified Compounds Against ASK1 | | |
|---|---|---|
| Compound No | Enzyme Activity B $IC_{50}$ (nM) | Enzyme Activity C $IC_{50}$ (nM) |
| 9 | 81 | 237 |
| 10 | 3 | 62 |
| 11 | 3 | 8 |
| 12 | 7 | 20 |
| 13 | 55 | 64 |
| 14 | 6 | 16 |
| 15 | 5 | 10 |
| 16 | 7 | 20 |
| 17 | 69 | 214 |
| 18 | 14 | 17 |
| 19 | 19 | 29 |
| 20 | 2 | 10 |
| 21 | — | 12446 |
| 22 | 2 | 7 |
| 23 | 4 | 6 |
| 24 | 11 | 18 |
| 25 | 60 | 146 |
| 26 | 9 | 12 |
| 27 | — | 528 |
| 28 | — | 16 |
| 29 | — | 38 |
| 30 | — | 19 |
| 31 | — | 19 |
| 32 | — | 122 |
| 33 | — | 41 |

What is claimed is:

1. A compound of the formula:

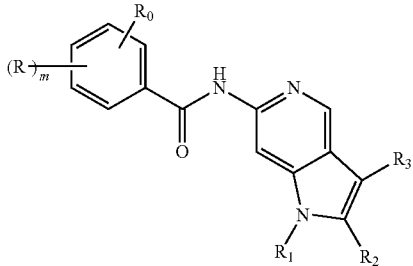

a stereoisomer thereof or a pharmaceutically acceptable salt of the compound or stereoisomer, wherein m is 0, 1, or 2;

$R_0$ is selected from the group consisting of

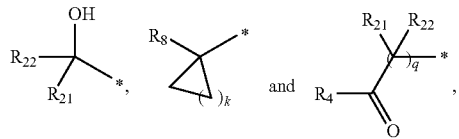

in which * represents a point of attachment;

each R is independently selected from the group consisting of hydroxy, nitro, halo, cyano, hetero($C_{1-5}$)aryloxy, ($C_{1-6}$)alkyl, amino($C_{1-6}$)alkyl, and halo($C_{1-6}$)alkyl, each unsubstituted or substituted with 1-3 substituents independently selected from the group consisting of hydroxy, halo, ($C_{1-6}$)alkoxy, halo($C_{1-6}$)alkoxy, amino, ($C_{1-6}$)alkyl, hydroxy($C_{1-6}$)alkyl, halo($C_{1-6}$)alkyl, perhalo($C_{1-6}$)alkyl, amino($C_{1-6}$)alkyl, hydroxy($C_{1-6}$)alkoxy, halo($C_{1-6}$)alkoxy, perhalo($C_{1-6}$)alkoxy, $R_9$-carbonyl($C_{1-6}$)alkyl, $R_9$-sulfonyl($C_{1-6}$)alkyl, $R_9$-carbonyl, and $R_9$-sulfonyl;

$R_1$ is selected from the group consisting of cyano, ($C_{1-6}$)alkyl, ($C_{2-6}$)alkenyl, ($C_{3-6}$)cycloalkyl, and sulfonyl, each unsubstituted or substituted with 1-3 substituents independently selected from the group consisting of hydroxy, halo, cyano, amino, carbonylamino, sulfonylamino, ($C_{3-6}$)cycloalkyl, oxycarbonyl, hydroxycarbonyl, aminocarbonyl, sulfonyl, aminosulfonyl, wherein the amino, carbonylamino, sulfonylamino, oxycarbonyl, aminocarbonyl, sulfonyl, and aminosulfonyl are each unsubstituted or further substituted with 1-2 substituents independently selected from the group consisting of ($C_{1-6}$)alkyl, halo($C_{1-6}$)alkyl, perhalo($C_{1-6}$)alkyl, and ($C_{3-6}$)cycloalkyl;

$R_2$ is selected from the group consisting of hydrogen, halo, nitro, cyano, thio, oxy, hydroxy, carbonyloxy, ($C_{1-6}$)alkoxy, carbonyl, oxycarbonyl, aminocarbonyl, sulfonyl, sulfinyl, ($C_{1-6}$)alkyl, halo($C_{1-6}$)alkyl, hydroxy($C_{1-6}$)alkyl, carbonyl($C_{1-6}$)alkyl, thiocarbonyl($C_{1-6}$)alkyl, sulfonyl($C_{1-6}$)alkyl, and sulfinyl($C_{1-6}$)alkyl, each unsubstituted or substituted with 1-3 substituents each of which is independently selected from the group consisting of hydroxy, unsubstituted amino, mono-substituted amino, di-substituted amino, ($C_{1-6}$)alkyl, and halo ($C_{1-6}$)alkyl;

$R_3$ is selected from the group consisting of hydrogen, halo, nitro, cyano, thio, oxy, hydroxy, carbonyloxy, ($C_{1-6}$)alkoxy, carbonyl, oxycarbonyl, aminocarbonyl, sulfonyl, sulfinyl, ($C_{1-6}$)alkyl, halo($C_{1-6}$)alkyl, hydroxy($C_{1-6}$)alkyl, carbonyl($C_{1-6}$)alkyl, thiocarbonyl($C_{1-6}$)alkyl, sulfonyl($C_{1-6}$)alkyl, and sulfinyl($C_{1-6}$)alkyl, each unsubstituted or substituted with 1-3 substituents each of which is independently selected from the group consisting of hydroxy, halo, ($C_{1-6}$)alkyl, halo($C_{1-6}$)alkyl, and perhalo($C_{1-6}$)alkyl;

$R_4$ is selected from the group consisting of hydroxy, unsubstituted amino, ($C_{1-6}$)alkylamino, (di-($C_{1-6}$)alkyl) amino, ($C_{1-6}$)alkoxy, and ($C_{1-6}$)alkyl;

$R_8$ is —$(CR_{23}R_{23'})_p$OH;

$R_9$ is selected from the group consisting of hydroxy, unsubstituted amino, ($C_{1-6}$)alkylamino, (di-($C_{1-6}$)alkyl) amino, ($C_{1-6}$)alkoxy, and ($C_{1-6}$)alkyl;

$R_{10}$ is selected from the group consisting of hydroxy, unsubstituted amino, ($C_{1-6}$)alkylamino, (di-($C_{1-6}$)alkyl) amino, ($C_{1-6}$)alkoxy, and ($C_{1-6}$)alkyl;

$R_{21}$ is selected from the group consisting of —$C(R_{23})_3$, —$(CR_{23}R_{23'})_p$—$C(R_{23})_3$, —$(CR_{23}R_{23'})_p$OH, —$(CR_{23}R_{23'})_p$C(O)R_{10}$, —$(CR_{23}R_{23'})_p$S(O)_2R_{10}$, and —$O(CR_{23}R_{23'})_p$OH, $R_{22}$ is selected from the group consisting of hydrogen, ($C_{1-6}$)alkyl, hydroxy($C_{1-6}$)alkyl and halo($C_{1-6}$)alkyl;

$R_{23}$ and $R_{23'}$ are each independently selected from the group consisting of hydrogen, halo, hydroxy, and ($C_{1-6}$) alkyl;

k is 1, 2, 3, or 4;

p is 1, 2, 3, or 4; and q is 1, 2, 3 or 4.

2. The compound according to claim 1, having the formula:

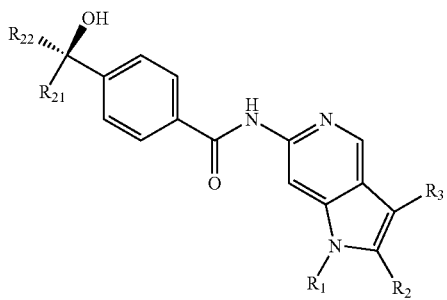

a stereoisomer thereof or a pharmaceutically acceptable salt of the compound or stereoisomer.

3. The compound or pharmaceutically acceptable salt according to claim 1, wherein
each R is independently selected from the group consisting of hydroxy, nitro, halo, cyano, $(C_{1-6})$alkoxy, —OCHF$_2$, —OCF$_3$, $(C_{1-6})$alkyl, hydroxy$(C_{1-6})$alkyl, —CHF$_2$, —CF$_3$, —C(CH$_3$)(OH)CF$_3$, —CH$_2$OCH$_2$CF$_3$, —C(O)OCH$_3$, —OCH(CH$_3$)$_2$, amino$(C_{1-6})$alkyl, hydroxycarbonylamino$(C_{1-6})$alkyl, $(C_{1-6})$alkoxycarbonylamino$(C_{1-6})$alkyl, and $(C_{1-6})$alkylcarbonylamino$(C_{1-6})$alkyl.

4. The compound or pharmaceutically acceptable salt according to claim 1, wherein R$_1$ is selected from the group consisting of $(C_{1-6})$alkyl, $(C_{3-6})$cycloalkyl, $(C_{3-6})$cycloalkyl$(C_{1-6})$alkyl, and $(C_{1-6})$alkylsulfonyl$(C_{1-6})$alkyl, each unsubstituted or mono- or di-$(C_{1-6})$alkyl substituted.

5. The compound or pharmaceutically acceptable salt according to claim 1, wherein R$_1$ is selected from the group consisting of methyl, ethyl, cyclopropyl, cyclopropylmethyl, and methylsulfonylmethyl.

6. The compound or pharmaceutically acceptable salt according to claim 1, wherein R$_2$ is selected from the group consisting of hydrogen, hydroxy, halo, cyano, $(C_{1-6})$alkyl, $(C_{2-6})$alkenyl, hydroxy$(C_{1-6})$alkyl, hydroxy$(C_{2-6})$alkenyl, dihydroxy$(C_{1-6})$alkyl, $(C_{1-6})$alkylsulfonyl, hydroxycarbonyl$(C_{1-6})$alkyl, aminocarbonyl$(C_{1-6})$alkyl, hydroxysulfonyl$(C_{1-6})$alkyl, and aminosulfonyl$(C_{1-6})$alkyl, wherein the amino of aminocarbonyl$(C_{1-6})$alkyl and aminosulfonyl$(C_{1-6})$alkyl are each unsubstituted, or mono- or di-$(C_{1-6})$alkyl substituted.

7. The compound or pharmaceutically acceptable salt according to claim 1, wherein R$_2$ is halo or hydrogen.

8. The compound or pharmaceutically acceptable salt according to claim 1, wherein R$_3$ is selected from the group consisting of hydrogen, halo, and $(C_{1-6})$alkyl.

9. The compound or pharmaceutically acceptable salt according to claim 1, wherein R$_3$ is selected from the group consisting of chloro, bromo, and methyl.

10. The compound or pharmaceutically acceptable salt according to claim 1, wherein R$_4$ is selected from the group consisting of hydroxy, $(C_{1-6})$alkyl, unsubstituted amino, $(C_{1-6})$alkylamino, and (di-$(C_{1-6})$alkyl)amino.

11. The compound or pharmaceutically acceptable salt according to claim 1, wherein R$_{21}$ is selected from the group consisting of $(C_{1-6})$alkyl and hydroxy$(C_{1-6})$alkyl.

12. The compound or pharmaceutically acceptable salt according to claim 1, wherein R$_{21}$ is selected from methyl, —CH$_2$OH, and —CH$_2$CH$_2$OH.

13. The compound or pharmaceutically acceptable salt according to claim 1, wherein R$_{21}$ is hydroxymethyl.

14. The compound or pharmaceutically acceptable salt according to claim 1, wherein R$_{22}$ is selected from the group consisting of $(C_{1-3})$alkyl and hydroxy$(C_{1-3})$alkyl.

15. The compound or pharmaceutically acceptable salt according to claim 1, wherein R$_{22}$ is selected from hydrogen, methyl, and CF$_3$.

16. The compound or pharmaceutically acceptable salt according to claim 1, wherein R$_{21}$ is selected from methyl, —CH$_2$OH, and —CH$_2$CH$_2$OH, and R$_{22}$ is selected from hydrogen, methyl, and CF$_3$.

17. The compound according to claim 1, which is selected from the group of compounds consisting of:
N-(1-(cyclopropylmethyl)-1H-pyrrolo[3,2-c]pyridin-6-yl)-4-(2-hydroxypropan-2-yl)benzamide;
N-(3-bromo-1-(cyclopropylmethyl)-1H-pyrrolo[3,2-c]pyridin-6-yl)-4-(2-hydroxypropan-2-yl)benzamide;
N-(3-bromo-1-ethyl-1H-pyrrolo[3,2-c]pyridin-6-yl)-4-(2-hydroxypropan-2-yl)benzamide;
N-(1-ethyl-3-methyl-1H-pyrrolo[3,2-c]pyridin-6-yl)-4-(2-hydroxypropan-2-yl)benzamide;
(R)-4-(1,2-dihydroxypropan-2-yl)-N-(1-ethyl-1H-pyrrolo[3,2-c]pyridin-6-yl)benzamide;
(R)—N-(3-chloro-1-ethyl-1H-pyrrolo[3,2-c]pyridin-6-yl)-4-(1,2-dihydroxypropan-2-yl)benzamide;
N-(3-bromo-1-methyl-1H-pyrrolo[3,2-c]pyridin-6-yl)-4-(2-hydroxypropan-2-yl)benzamide;
(R)—N-(3-bromo-1-methyl-1H-pyrrolo[3,2-c]pyridin-6-yl)-4-(1,2-dihydroxypropan-2-yl)benzamide;
(R)—N-(1-cyclopropyl-1H-pyrrolo[3,2-c]pyridin-6-yl)-4-(1,2-dihydroxypropan-2-yl)benzamide;
(R)-4-(1,2-dihydroxypropan-2-yl)-N-(1-ethyl-3-methyl-1H-pyrrolo[3,2-c]pyridin-6-yl)benzamide;
N-(1,3-dimethyl-1H-pyrrolo[3,2-c]pyridin-6-yl)-4-(2-hydroxypropan-2-yl)benzamide;
(R)—N-(3-bromo-1-ethyl-1H-pyrrolo[3,2-c]pyridin-6-yl)-4-(1,2-dihydroxypropan-2-yl)benzamide;
4-(2-hydroxypropan-2-yl)-N-(1-(methylsulfonylmethyl)-1H-pyrrolo[3,2-c]pyridin-6-yl)benzamide;
(R)—N-(3-bromo-1-cyclopropyl-1H-pyrrolo[3,2-c]pyridin-6-yl)-4-(1,2-dihydroxypropan-2-yl)benzamide;
(R)—N-(3-chloro-1-cyclopropyl-1H-pyrrolo[3,2-c]pyridin-6-yl)-4-(1,2-dihydroxypropan-2-yl)benzamide;
N-(3-chloro-1-methyl-1H-pyrrolo[3,2-c]pyridin-6-yl)-4-(2-hydroxypropan-2-yl)benzamide;
N-(2,3-dichloro-1-methyl-1H-pyrrolo[3,2-c]pyridin-6-yl)-4-(2-hydroxypropan-2-yl)benzamide;
(S)—N-(3-chloro-1-ethyl-1H-pyrrolo[3,2-c]pyridin-6-yl)-4-(1,2-dihydroxypropan-2-yl)benzamide;
(R)-4-(1,2-dihydroxypropan-2-yl)-N-(1-ethyl-1H-pyrrolo[3,2-c]pyridin-6-yl)-3-methylbenzamide;
N-(3-chloro-1-cyclopropyl-1H-pyrrolo[3,2-c]pyridin-6-yl)-4-(1-hydroxy-2-methylpropan-2-yl)benzamide;
(S)—N-(3-chloro-1-methyl-1H-pyrrolo[3,2-c]pyridin-6-yl)-4-(1,2-dihydroxypropan-2-yl)benzamide;
(S)—N-(2,3-dichloro-1-methyl-1H-pyrrolo[3,2-c]pyridin-6-yl)-4-(1,2-dihydroxypropan-2-yl)benzamide;
(R)—N-(3-chloro-1-methyl-1H-pyrrolo[3,2-c]pyridin-6-yl)-4-(1,2-dihydroxypropan-2-yl)benzamide;
(R)—N-(2,3-dichloro-1-methyl-1H-pyrrolo[3,2-c]pyridin-6-yl)-4-(1,2-dihydroxypropan-2-yl)benzamide;
(R)—N-(3-chloro-1-ethyl-1H-pyrrolo[3,2-c]pyridin-6-yl)-4-(1,2-dihydroxypropan-2-yl)-3-methylbenzamide;
a stereoisomer of any one of the aforementioned compounds; and
a pharmaceutically acceptable salt of any one of the aforementioned compounds or stereoisomer.

18. The compound or pharmaceutically acceptable salt according to claim 1, wherein the compound is a single stereoisomer.

19. The compound according to claim 1, which is N-(3-bromo-1-(cyclopropylmethyl)-1H-pyrrolo[3,2-c]pyridin-6-yl)-4-(2-hydroxypropan-2-yl)benzamide or a pharmaceutically acceptable salt thereof.

20. The compound according to claim 1, which is N-(1-ethyl-3-methyl-1H-pyrrolo[3,2-c]pyridin-6-yl)-4-(2-hydroxypropan-2-yl)benzamide or a pharmaceutically acceptable salt thereof.

21. The compound according to claim 1, which is (R)-N-(3-chloro-1-ethyl-1H-pyrrolo[3,2-c]pyridin-6-yl)-4-(1,2-dihydroxypropan-2-yl)benzamide or a pharmaceutically acceptable salt thereof.

22. The compound according to claim 1, which is (R)-N-(3-chloro-1-cyclopropyl-1H-pyrrolo[3,2-c]pyridin-6-yl)-4-(1,2-dihydroxypropan-2-yl)benzamide or a pharmaceutically acceptable salt thereof.

23. The compound according to claim 1, which is (S)-N-(3-chloro-1-ethyl-1H-pyrrolo[3,2-c]pyridin-6-yl)-4-(1,2-dihydroxypropan-2-yl)benzamide or a pharmaceutically acceptable salt thereof.

24. The compound according to claim 1, which is N-(3-chloro-1-cyclopropyl-1H-pyrrolo[3,2-c]pyridin-6-yl)-4-(1-hydroxy-2-methylpropan-2-yl)benzamide or a pharmaceutically acceptable salt thereof.

25. A pharmaceutical composition comprising a compound or pharmaceutically acceptable salt as defined in claim 1, and a pharmaceutically acceptable excipient.

26. A method for modulating the activity of ASK1 in a subject, the method comprising administering a compound or pharmaceutically acceptable salt as defined in claim 1 to the subject.

* * * * *

SEQUENCE LISTING

<160> NUMBER OF SEQ ID NOS: 2

<210> SEQ ID NO 1
<211> LENGTH: 65
<212> TYPE: DNA
<213> ORGANISM: Artificial Sequence
<220> FEATURE:
<223> OTHER INFORMATION: Synthetic Primers

```
<400> SEQUENCE: 1
aaaagtcgac atggactaca aggacgacga tgacaaggtg aacaccatta ccgaagagaa        60
gggga                                                                   65

<210> SEQ ID NO 2
<211> LENGTH: 39
<212> TYPE: DNA
<213> ORGANISM: Artificial Sequence
<220> FEATURE:
<223> OTHER INFORMATION: Synthetic Primers

<400> SEQUENCE: 2
aaagcggccg ctcaagtctg tttgtttcga aagtcaatg                              39
```